United States Patent
Shelton, IV et al.

(10) Patent No.: US 12,082,885 B2
(45) Date of Patent: Sep. 10, 2024

(54) METHODS AND SYSTEMS FOR CONTROLLING COOPERATIVE SURGICAL INSTRUMENTS

(71) Applicant: Cilag GmbH International, Zug (CH)

(72) Inventors: Frederick E. Shelton, IV, Hillsboro, OH (US); Charles J. Scheib, Loveland, OH (US); Jason L. Harris, Lebanon, OH (US)

(73) Assignee: Cilag GmbH International, Zug (CH)

( * ) Notice: Subject to any disclaimer, the term of this patent is extended or adjusted under 35 U.S.C. 154(b) by 0 days.

(21) Appl. No.: 17/451,949

(22) Filed: Oct. 22, 2021

(65) Prior Publication Data

US 2023/0093972 A1    Mar. 30, 2023

Related U.S. Application Data

(60) Provisional application No. 63/249,870, filed on Sep. 29, 2021.

(51) Int. Cl.
*A61B 34/20* (2016.01)
*A61B 1/00* (2006.01)
(Continued)

(52) U.S. Cl.
CPC .......... *A61B 34/20* (2016.02); *A61B 1/00006* (2013.01); *A61B 1/000095* (2022.02);
(Continued)

(58) Field of Classification Search
CPC ...... A61B 2034/302; A61B 2034/2065; A61B 34/20; A61B 1/000095; A61B 1/005;
(Continued)

(56) References Cited

U.S. PATENT DOCUMENTS 5,188,104 A    2/1993    Wernicke et al.
5,231,988 A    8/1993    Wernicke et al.
(Continued)

FOREIGN PATENT DOCUMENTS

EP    3005993 A2    4/2016
EP    1886711 B1    4/2018
(Continued)

OTHER PUBLICATIONS

U.S. Appl. No. 17/450,020, filed Oct. 5, 2021, Frederick E. Shelton, IV et al.
(Continued)

*Primary Examiner* — Anh Tuan T Nguyen
*Assistant Examiner* — Shankar Raj Ghimire

(57) ABSTRACT

Systems, devices, and methods for controlling cooperative surgical instruments are provided. Various aspects of the present disclosure provide for coordinated operation of surgical instruments accessing a common body cavity of a patient from different approaches to achieve a common surgical purpose. For example, various methods, devices, and systems disclosed herein can enable the coordinated treatment of surgical tissue by disparate minimally invasive surgical systems that approach the tissue from varying anatomical spaces and operate in concert with one another to effect a desired surgical treatment.

20 Claims, 20 Drawing Sheets

(51) Int. Cl.

| | | |
|---|---|---|
| *A61B 1/005* | (2006.01) | |
| *A61B 1/04* | (2006.01) | |
| *A61B 1/313* | (2006.01) | |
| *A61B 5/00* | (2006.01) | |
| *A61B 5/06* | (2006.01) | |
| *A61B 17/00* | (2006.01) | |
| *A61B 17/11* | (2006.01) | |
| *G16H 20/40* | (2018.01) | |
| *G16H 40/63* | (2018.01) | |
| *A61B 17/115* | (2006.01) | |
| *A61B 34/30* | (2016.01) | |

(52) U.S. Cl.
CPC .............. *A61B 1/005* (2013.01); *A61B 1/044* (2022.02); *A61B 1/3132* (2013.01); *A61B 5/0075* (2013.01); *A61B 5/0084* (2013.01); *A61B 5/065* (2013.01); *A61B 5/6835* (2013.01); *A61B 17/1114* (2013.01); *G16H 20/40* (2018.01); *G16H 40/63* (2018.01); *A61B 2017/00876* (2013.01); *A61B 2017/1139* (2013.01); *A61B 17/115* (2013.01); *A61B 2034/2051* (2016.02); *A61B 2034/2055* (2016.02); *A61B 2034/2057* (2016.02); *A61B 2034/2065* (2016.02); *A61B 2034/302* (2016.02)

(58) Field of Classification Search
CPC ... A61B 1/044; A61B 17/1114; A61B 1/3132; A61B 17/115; A61B 2034/2055; G16H 40/63; G16H 20/40
See application file for complete search history.

(56) References Cited

U.S. PATENT DOCUMENTS

| | | | |
|---|---|---|---|
| 5,256,149 A | 10/1993 | Banik et al. | |
| 5,263,480 A | 11/1993 | Wernicke et al. | |
| 5,540,730 A | 7/1996 | Terry, Jr. et al. | |
| 5,558,671 A | 9/1996 | Yates | |
| 5,954,731 A * | 9/1999 | Yoon | A61B 17/062 606/147 |
| 6,086,528 A | 7/2000 | Adair | |
| 7,143,925 B2 | 12/2006 | Shelton, IV et al. | |
| 7,387,606 B2 * | 6/2008 | Weinberg | A61B 1/31 600/156 |
| 7,585,290 B2 | 9/2009 | Kathrani et al. | |
| 7,601,118 B2 | 10/2009 | Smith et al. | |
| 8,068,649 B2 * | 11/2011 | Green | H04N 13/398 348/45 |
| 8,317,070 B2 | 11/2012 | Hueil et al. | |
| 8,330,811 B2 * | 12/2012 | Macguire, Jr. | H04N 7/18 348/121 |
| 8,352,026 B2 | 1/2013 | DiUbaldi | |
| 8,393,514 B2 | 3/2013 | Shelton, IV et al. | |
| 8,517,933 B2 | 8/2013 | Mohr | |
| 8,545,515 B2 | 10/2013 | Prisco et al. | |
| 8,551,115 B2 | 10/2013 | Steger et al. | |
| 8,623,028 B2 | 1/2014 | Rogers et al. | |
| 8,632,462 B2 | 1/2014 | Yoo et al. | |
| 8,636,751 B2 | 1/2014 | Albrecht et al. | |
| 8,734,478 B2 | 5/2014 | Widenhouse et al. | |
| 8,753,338 B2 | 6/2014 | Widenhouse et al. | |
| 8,771,180 B2 | 7/2014 | Mohr | |
| 8,812,100 B2 | 8/2014 | Voegele et al. | |
| 8,831,782 B2 | 9/2014 | Itkowitz | |
| 8,888,789 B2 | 11/2014 | Prisco et al. | |
| 8,919,348 B2 | 12/2014 | Williams et al. | |
| 8,961,406 B2 | 2/2015 | Ortiz et al. | |
| 9,044,606 B2 | 6/2015 | Harris et al. | |
| 9,072,535 B2 | 7/2015 | Shelton, IV et al. | |
| 9,072,536 B2 | 7/2015 | Shelton, IV et al. | |
| 9,204,879 B2 | 12/2015 | Shelton, IV | |
| 9,216,062 B2 | 12/2015 | Duque et al. | |
| 9,254,178 B2 | 2/2016 | Prisco et al. | |
| 9,274,047 B2 | 3/2016 | Velten et al. | |
| 9,283,050 B2 | 3/2016 | Prisco et al. | |
| 9,320,416 B2 | 4/2016 | Cooper et al. | |
| 9,339,341 B2 | 5/2016 | Cooper | |
| 9,358,074 B2 | 6/2016 | Schena et al. | |
| 9,393,017 B2 | 7/2016 | Flanagan et al. | |
| 9,561,038 B2 | 2/2017 | Shelton, IV et al. | |
| 9,572,481 B2 | 2/2017 | Duindam et al. | |
| 9,636,186 B2 | 5/2017 | Kumar et al. | |
| 9,757,128 B2 | 9/2017 | Baber et al. | |
| 9,861,271 B2 * | 1/2018 | Liu | A61B 5/06 |
| 9,962,161 B2 | 5/2018 | Scheib et al. | |
| 10,092,738 B2 * | 10/2018 | Harris | A61N 5/0622 |
| 10,179,024 B2 | 1/2019 | Yeung | |
| 10,206,682 B2 | 2/2019 | Bakos et al. | |
| 10,245,069 B2 | 4/2019 | Rogers et al. | |
| 10,383,765 B2 * | 8/2019 | Alvarez | A61B 34/30 |
| 10,492,788 B2 | 12/2019 | Swayze et al. | |
| 10,517,600 B2 | 12/2019 | Beisel et al. | |
| 10,569,071 B2 | 2/2020 | Harris et al. | |
| 10,716,564 B2 | 7/2020 | Shelton, IV et al. | |
| 10,751,117 B2 | 8/2020 | Witt et al. | |
| 10,779,831 B2 * | 9/2020 | Lukin | A61B 17/1114 |
| 10,792,034 B2 | 10/2020 | Scheib et al. | |
| 10,856,928 B2 | 12/2020 | Shelton, IV et al. | |
| 10,925,598 B2 | 2/2021 | Scheib et al. | |
| 11,033,272 B2 | 6/2021 | Fegelman et al. | |
| 11,051,876 B2 | 7/2021 | Shelton, IV et al. | |
| 11,957,421 B2 | 4/2024 | Shelton, IV et al. | |
| 2002/0049378 A1 * | 4/2002 | Grzeszczuk | A61B 6/12 378/20 |
| 2002/0133173 A1 * | 9/2002 | Brock | A61B 34/20 606/130 |
| 2003/0013949 A1 | 1/2003 | Moll et al. | |
| 2004/0204645 A1 | 10/2004 | Saadat et al. | |
| 2005/0267529 A1 * | 12/2005 | Crockett | A61B 17/0643 606/215 |
| 2005/0277998 A1 | 12/2005 | Tracey et al. | |
| 2006/0195146 A1 | 8/2006 | Tracey et al. | |
| 2006/0195153 A1 | 8/2006 | DiUbaldi et al. | |
| 2006/0258938 A1 * | 11/2006 | Hoffman | A61B 34/20 600/424 |
| 2007/0135803 A1 | 6/2007 | Belson | |
| 2007/0185541 A1 | 8/2007 | DiUbaldi et al. | |
| 2007/0198074 A1 | 8/2007 | Dann et al. | |
| 2007/0244387 A1 * | 10/2007 | Rodriguez Ponce | G16Z 99/00 600/411 |
| 2008/0004603 A1 | 1/2008 | Larkin et al. | |
| 2008/0065110 A1 * | 3/2008 | Duval | A61B 1/00154 606/130 |
| 2008/0071141 A1 | 3/2008 | Gattani et al. | |
| 2008/0082114 A1 | 4/2008 | McKenna et al. | |
| 2008/0132962 A1 | 6/2008 | DiUbaldi et al. | |
| 2008/0147146 A1 | 6/2008 | Wahlgren et al. | |
| 2009/0062792 A1 | 3/2009 | Vakharia et al. | |
| 2009/0132962 A1 | 5/2009 | DiUbaldi et al. | |
| 2009/0149918 A1 | 6/2009 | Krulevitch et al. | |
| 2009/0157149 A1 | 6/2009 | Wahlgren et al. | |
| 2009/0171196 A1 | 7/2009 | Olson et al. | |
| 2010/0161001 A1 | 6/2010 | DiUbaldi et al. | |
| 2010/0161005 A1 | 6/2010 | Wahlgren et al. | |
| 2010/0191267 A1 | 7/2010 | Fox | |
| 2010/0239648 A1 | 9/2010 | Smith et al. | |
| 2010/0318099 A1 * | 12/2010 | Itkowitz | A61B 34/30 606/130 |
| 2011/0009886 A1 | 1/2011 | Gagner et al. | |
| 2011/0054253 A1 * | 3/2011 | Jorda Albinana | A61B 1/00156 600/118 |
| 2011/0058033 A1 * | 3/2011 | Baker | G01C 11/02 348/139 |
| 2011/0094773 A1 | 4/2011 | Bare et al. | |
| 2011/0118708 A1 | 5/2011 | Burbank et al. | |
| 2011/0144560 A1 | 6/2011 | Gagner et al. | |
| 2012/0150192 A1 | 6/2012 | Dachs, II et al. | |
| 2012/0209314 A1 | 8/2012 | Weir et al. | |

(56) References Cited

U.S. PATENT DOCUMENTS

| | | |
|---|---|---|
| 2012/0232339 A1* | 9/2012 | Csiky ................. A61B 1/00128 604/95.04 |
| 2013/0105545 A1 | 5/2013 | Burbank |
| 2013/0105552 A1 | 5/2013 | Weir et al. |
| 2013/0146643 A1 | 6/2013 | Schmid et al. |
| 2013/0221065 A1 | 8/2013 | Aronhalt et al. |
| 2013/0226285 A1 | 8/2013 | Strommer |
| 2013/0253550 A1* | 9/2013 | Beisel .................... A61B 17/11 606/153 |
| 2013/0256377 A1 | 10/2013 | Schmid et al. |
| 2014/0005684 A1 | 1/2014 | Kim et al. |
| 2014/0066717 A1 | 3/2014 | Rogers et al. |
| 2014/0121678 A1 | 5/2014 | Trusty et al. |
| 2014/0194732 A1* | 7/2014 | Nakaguchi ........... A61B 90/361 600/424 |
| 2014/0228636 A1 | 8/2014 | Nimkar et al. |
| 2014/0303491 A1 | 10/2014 | Shekhar et al. |
| 2015/0129634 A1 | 5/2015 | Shelton, IV et al. |
| 2015/0133995 A1 | 5/2015 | Shelton, IV et al. |
| 2015/0133996 A1 | 5/2015 | Shelton, IV et al. |
| 2015/0134076 A1 | 5/2015 | Shelton, IV et al. |
| 2015/0134077 A1 | 5/2015 | Shelton, IV et al. |
| 2015/0145953 A1* | 5/2015 | Fujie ..................... A61B 90/37 348/45 |
| 2015/0238268 A1 | 8/2015 | Weir et al. |
| 2015/0238276 A1* | 8/2015 | Atarot ................ A61B 1/00064 606/130 |
| 2015/0257841 A1 | 9/2015 | Dachs, II |
| 2015/0257842 A1 | 9/2015 | Dachs, II |
| 2015/0272575 A1 | 10/2015 | Leimbach et al. |
| 2015/0320514 A1* | 11/2015 | Ahn ....................... A61B 34/30 606/130 |
| 2015/0351758 A1 | 12/2015 | Shelton, IV et al. |
| 2016/0007827 A1* | 1/2016 | Frimer ................... G05B 15/02 700/275 |
| 2016/0022125 A1 | 1/2016 | Nicolau et al. |
| 2016/0022266 A1 | 1/2016 | Lukin et al. |
| 2016/0203282 A1* | 7/2016 | Azizian ................ G16H 40/63 700/275 |
| 2016/0256071 A1 | 9/2016 | Shelton, IV et al. |
| 2016/0262761 A1 | 9/2016 | Beisel et al. |
| 2016/0303743 A1 | 10/2016 | Rockrohr |
| 2016/0324523 A1* | 11/2016 | Lukin ................. A61B 17/1114 |
| 2016/0354152 A1* | 12/2016 | Beck ...................... A61B 34/10 |
| 2017/0035425 A1 | 2/2017 | Fegelman et al. |
| 2017/0055819 A1 | 3/2017 | Hansen et al. |
| 2017/0071693 A1 | 3/2017 | Taylor et al. |
| 2017/0128041 A1 | 5/2017 | Hasser et al. |
| 2017/0128144 A1 | 5/2017 | Hasser et al. |
| 2017/0128145 A1 | 5/2017 | Hasser et al. |
| 2017/0156732 A1* | 6/2017 | Lehrberg ................ A61B 90/96 |
| 2017/0164869 A1 | 6/2017 | Lee et al. |
| 2017/0172662 A1* | 6/2017 | Panescu ................. A61B 34/00 |
| 2017/0202591 A1 | 7/2017 | Shelton, IV et al. |
| 2017/0202624 A1* | 7/2017 | Atarot ................... A61B 90/03 |
| 2017/0212723 A1* | 7/2017 | Atarot ................... G10L 15/28 |
| 2017/0215969 A1* | 8/2017 | Zhai ....................... A61B 5/08 |
| 2017/0251900 A1* | 9/2017 | Hansen ................ A61B 1/3132 |
| 2017/0265866 A1* | 9/2017 | Ryou ................... A61B 17/3478 |
| 2017/0360513 A1* | 12/2017 | Amiot ..................... A61B 34/10 |
| 2018/0049820 A1 | 2/2018 | Widenhouse et al. |
| 2018/0049821 A1* | 2/2018 | Shelton, IV ... A61B 17/320068 |
| 2018/0117343 A1 | 5/2018 | Zhu et al. |
| 2018/0177556 A1 | 6/2018 | Noonan |
| 2018/0214149 A1 | 8/2018 | Hunt et al. |
| 2018/0296280 A1 | 10/2018 | Kurihara et al. |
| 2018/0325604 A1* | 11/2018 | Atarot ................... A61B 5/0035 |
| 2018/0353174 A1 | 12/2018 | Widenhouse et al. |
| 2019/0008367 A1 | 1/2019 | Ishikawa et al. |
| 2019/0099209 A1 | 4/2019 | Witt et al. |
| 2019/0125431 A1 | 5/2019 | Shelton, IV et al. |
| 2019/0125454 A1 | 5/2019 | Stokes et al. |
| 2019/0125457 A1* | 5/2019 | Parihar .................. A61B 34/10 |
| 2019/0200844 A1 | 7/2019 | Shelton, IV et al. |
| 2019/0200905 A1 | 7/2019 | Shelton, IV et al. |
| 2019/0200981 A1* | 7/2019 | Harris ................ A61B 18/1445 |
| 2019/0201046 A1 | 7/2019 | Shelton, IV et al. |
| 2019/0201088 A1 | 7/2019 | Shelton, IV et al. |
| 2019/0201114 A1 | 7/2019 | Shelton, IV et al. |
| 2019/0201136 A1 | 7/2019 | Shelton, IV et al. |
| 2019/0201140 A1 | 7/2019 | Yates et al. |
| 2019/0204201 A1 | 7/2019 | Shelton, IV et al. |
| 2019/0206004 A1 | 7/2019 | Shelton, IV et al. |
| 2019/0206050 A1 | 7/2019 | Yates et al. |
| 2019/0206555 A1 | 7/2019 | Morgan et al. |
| 2019/0207857 A1* | 7/2019 | Shelton, IV ......... A61B 5/0002 |
| 2019/0239972 A1* | 8/2019 | Chassot ................ B25J 9/1682 |
| 2019/0246883 A1* | 8/2019 | Bashour .............. A61B 1/00082 |
| 2020/0000530 A1 | 1/2020 | DeFonzo et al. |
| 2020/0015668 A1 | 1/2020 | Scheib |
| 2020/0015897 A1 | 1/2020 | Scheib et al. |
| 2020/0015898 A1 | 1/2020 | Scheib et al. |
| 2020/0015899 A1 | 1/2020 | Scheib et al. |
| 2020/0015900 A1 | 1/2020 | Scheib et al. |
| 2020/0015901 A1 | 1/2020 | Scheib et al. |
| 2020/0015902 A1* | 1/2020 | Scheib ................. A61B 5/0036 |
| 2020/0015903 A1 | 1/2020 | Scheib et al. |
| 2020/0015906 A1* | 1/2020 | Scheib ................ G01N 21/4795 |
| 2020/0015907 A1 | 1/2020 | Scheib |
| 2020/0015914 A1 | 1/2020 | Scheib et al. |
| 2020/0015923 A1 | 1/2020 | Scheib et al. |
| 2020/0015924 A1 | 1/2020 | Scheib et al. |
| 2020/0015925 A1* | 1/2020 | Scheib ................. A61B 1/0638 |
| 2020/0078109 A1 | 3/2020 | Steger et al. |
| 2020/0085516 A1 | 3/2020 | DeFonzo et al. |
| 2020/0100855 A1 | 4/2020 | Leparmentier et al. |
| 2020/0170720 A1 | 6/2020 | Ummalaneni |
| 2020/0187946 A1 | 6/2020 | Baron et al. |
| 2020/0188043 A1 | 6/2020 | Yu et al. |
| 2020/0253669 A1* | 8/2020 | Diolaiti ................. A61B 34/76 |
| 2020/0289205 A1* | 9/2020 | Scheib ................ A61B 1/00042 |
| 2020/0315723 A1 | 10/2020 | Hassan et al. |
| 2020/0337706 A1 | 10/2020 | Truckai et al. |
| 2021/0085410 A1 | 3/2021 | Hassan |
| 2021/0186615 A1* | 6/2021 | Shmayahu ............. A61B 90/03 |
| 2021/0196098 A1* | 7/2021 | Shelton, IV .......... G16H 20/40 |
| 2021/0196108 A1* | 7/2021 | Shelton, IV .......... A61B 1/046 |
| 2021/0196109 A1* | 7/2021 | Shelton, IV ........... A61B 1/05 |
| 2021/0196381 A1* | 7/2021 | Eckert ................. A61B 1/0638 |
| 2021/0196382 A1* | 7/2021 | Mumaw ................ A61B 5/1076 |
| 2021/0196383 A1* | 7/2021 | Shelton, IV .......... A61B 34/70 |
| 2021/0196384 A1* | 7/2021 | Shelton, IV .......... G16H 30/40 |
| 2021/0196385 A1* | 7/2021 | Shelton, IV .......... A61B 1/0638 |
| 2021/0196386 A1* | 7/2021 | Shelton, IV .......... G16H 30/40 |
| 2021/0196399 A1* | 7/2021 | Ayvali ..................... A61B 34/20 |
| 2021/0196423 A1* | 7/2021 | Shelton, IV ............ A61B 1/05 |
| 2021/0196424 A1* | 7/2021 | Shelton, IV ........... G06T 7/521 |
| 2021/0196425 A1* | 7/2021 | Shelton, IV .......... A61B 90/30 |
| 2021/0199557 A1* | 7/2021 | Shelton, IV .......... G16H 40/63 |
| 2021/0315636 A1* | 10/2021 | Akbarian ............... A61B 34/20 |
| 2021/0345856 A1* | 11/2021 | Uyama ................. H04N 13/271 |
| 2021/0386491 A1* | 12/2021 | Shmayahu ............. A61M 5/178 |
| 2021/0393338 A1* | 12/2021 | Graetzel ................ A61B 34/74 |
| 2021/0393344 A1* | 12/2021 | Graetzel ................ A61B 34/70 |
| 2022/0323076 A1 | 10/2022 | Brahmstedt et al. |
| 2023/0096691 A1 | 3/2023 | Shelton, IV et al. |
| 2023/0100698 A1 | 3/2023 | Shelton, IV et al. |
| 2023/0101714 A1 | 3/2023 | Shelton, IV et al. |

FOREIGN PATENT DOCUMENTS

| | | |
|---|---|---|
| EP | 3643265 A1 | 4/2020 |
| EP | 3673854 A1 | 7/2020 |
| WO | 2011100625 A2 | 8/2011 |
| WO | WO-2012007052 A1 | 1/2012 |
| WO | WO-2014151621 A1 | 9/2014 |
| WO | WO-2015142814 A1 | 9/2015 |
| WO | WO-2015153636 A1 | 10/2015 |
| WO | WO-2015153642 A1 | 10/2015 |
| WO | WO-2016144937 A1 | 9/2016 |
| WO | WO-2016144998 A1 | 9/2016 |
| WO | WO-2016183054 A1 | 11/2016 |
| WO | WO-2016205266 A1 | 12/2016 |

(56) References Cited

FOREIGN PATENT DOCUMENTS

| WO | WO-2016205452 A1 | 12/2016 |
|---|---|---|
| WO | WO-2016209769 A1 | 12/2016 |
| WO | WO-2017044406 A1 | 3/2017 |
| WO | WO-2017053358 A1 | 3/2017 |
| WO | WO-2017053363 A1 | 3/2017 |
| WO | WO-2017053507 A1 | 3/2017 |
| WO | WO-2017053698 A1 | 3/2017 |
| WO | WO-2017075121 A1 | 5/2017 |
| WO | WO-2017116793 A1 | 7/2017 |

OTHER PUBLICATIONS

U.S. Appl. No. 17/451,948, filed Oct. 22, 2021, Frederick E. Shelton, IV et al.
U.S. Appl. No. 17/451,950, filed Oct. 22, 2021, Frederick E. Shelton, IV et al.
International Search Report and Written Opinion for International Application No. PCT/IB2022/059084, dated Dec. 7, 2022, 17 pages.
"Fiber Bragg Gatings," RP Photonics Encyclopedia, available at <https://www.rp-photonics.com/fiber_bragg_gratings.html>, dated no later than Apr. 5, 2021 (12 pages).
"Ion by Intuitive," available at <https://www.intuitive.com/en-us/products-and-services/ion>, dated no later than Apr. 5, 2021 (5 pages).
Aisu et al., Laparoscopic and endoscopic cooperative surgery for gastric tumors: Perspective for actual practice and oncological benefits,: World J Gastroint Oncol, Nov. 15, 2018, 10(11): 381-397.
Akirov, "Duodenal Mucosal Resurfacing May Safely Improve Glycemic Control in T2D," Aug. 19, 2019, Haymarket Media, Inc., 14 pages.
Brace et al., "Thermal Tumor Ablation in Clinical Use," IEEE Pulse, 2011, 2(5):28-38.
Carlota V., "4D printing reconfigurable materials for use in aerospace, medical and robotics fields," Apr. 3, 2019, available at <https://www.3dnatices.com/en/4d-printing-materials-030420195/> (7 pages).
Chauhan etal, "Enteroscopy," Gastrointestinal Endoscopy, 2015, vol. 82, No. 6, 975-990.
Conway et al., "Endoscopic hemostatic devices," Gastrointestinal Endoscopy, 2009, vol. 69, No. 6, 987-996.
Dunkin et al., "Thin-layer ablation of human esophageal epithelium using a bipolar radiofrequency balloon device," Surg Endosc (2006) 20: 125-130.
Ethlcon, "Laparoscopic Sizing Tool: LINX® Reflux Management System," 2019 (6 pages).
Fried et al., "A novel approach to glycemic control in type 2 diabetes mellius, partial jejunal diversion: pre-clinical to clinical pathway," BMJ Open Diab Res Care 2017; 5:e000431.doi:10.1136*BMJdrc-2017000431.
Garvey, "Ablation of the Duodenal Mucosa as a Strategy for Glycemic Control in Diabetes: Role of Nutrient Signaling or Simple Weight Loss," Diabetes Care 2016; 39:2108-2110.
Gioux et al., "Image-Guided Surgery using Invisible Near-Infrared Light: Fundamental of Clinical Translation," Mol Imaging, Oct. 2010, 9)5): 237-255.
Gupta, "Understanding Image Recognition and its Uses," elnfochips, available at <http://www.einfochips.com/blog/understanding-image-recognition-and-its-uses/>, Dec. 11, 2019.
Hiki et al., "Laparoscopic and endoscopic cooperative surgery for gastrointestinal stromal tumor dissection," Surg Endosc (2008) 22:1729-1735.
Intuitive Surgical, "Da Vinci Xi Single-Site Technology: Solutions For Single-Incision Surgery," 2016 (10 pages).
Kurata et al., "Time-Of-Flight Near-Infrared Spectroscopy For Nondestructive Measurement of Internal Quality in Grapefruit," Journal of the American Society for Horticultural Science, May 2013 vol. 138 No. 3 225-228.
Machytka et al., "Partial jejunal diversion using an incisionless magnetic anastomosis system: 1-year interim results in patients with obesity and diabetes," Gastrointestinal Endoscopy, 2017, vol. 86, No. 5, 904-912.
Matsuda et al., "Laparoscopic endoscopic cooperative surgery (LECS) for the upper gastrointestinal tract," Transl Gastroenterol Hepatol 2017, 2:40 (6 pages).
Miklavčič et al., "Electric Properties of Tissues," Wiley Encyclopedia of Biomedical Engineering, 2006, 1-12.
Sculpteo, "4D Printing: A technology coming from the future," 3D Learning Hub, dated no later than Aug. 26, 2021 (12 pages).
Seeley et al., "The Role of Gut Adaptation in the Potent Effects of Multiple Bariatric Surgeries on Obesity and Diabetes," Cell Metabolism 21, Mar. 3, 2015, 369-378.
Tamegai et al., "Laparoscopic and endoscopic cooperative surgery (LECS) to overcome the limitations of endoscopic resection for colorectal tumors," Endosc Int Open, Dec. 2018, 6(12): E1477-E1485.
Tokar et al., "Electrosurgical generators," Gastrointestinal Endoscopy, 2013, vol. 78, No. 2, 197-208.
Tomie et al., "Blue Laser Imaging-Bright Improves Endoscopic Recognition of Superficial Esophageal Squamous Cell Carcinoma," Gastroenterology Research and Practice, vol. 2016, Article ID 6140854, 7 pages.
Toposens, "Advanced Ultrasonic Sensors: What Makes Them Different?" available at <https://toposens.com/technology/>, 2020.
Toposens, "Beacon Based 3D Tracking System," available at <https://toposens.com/beacon-based-3d-ttracking-system/>, 2020.
U.S. Appl. No. 17/449,765 entitled "Cooperative Access Hybrid Procedures", filed Oct. 1, 2021.
U.S. Appl. No. 17/493,904 entitled "Surgical Methods Using Multi-Source Imaging", filed Oct. 5, 2021.
U.S. Appl. No. 17/450,025 entitled "Methods for Controlling Cooperative Surgical Instruments", filed Oct. 5, 2021.
U.S. Appl. No. 17/450,027 entitled "Methods for Controlling Cooperative Surgical Instruments", filed Oct. 5, 2021.
U.S. Appl. No. 17/493,913 entitled "Surgical Methods Using Fiducial Identification and Tracking", filed Oct. 5, 2021.
U.S. Appl. No. 17/494,364 entitled "Surgical Methods for Control of One Visualization With Another ", filed Oct. 5, 2021.
U.S. Appl. No. 17/068,857 entitled "Adaptive Responses From Smart Packaging of Drug Delivery Absorbable Adjuncts", filed Oct. 13, 2020.
U.S. Appl. No. 17/068,858 entitled "Drug Administration Devices That Communicate With Surgical Hubs", filed Oct. 13, 2020.
U.S. Appl. No. 17/068,859 entitled "Controlling Operation of Drug Administration Devices Using Surgical Hubs", filed Oct. 13, 2020.
U.S. Appl. No. 17/068,863 entitled "Patient Monitoring Using Drug Administration Devices", filed Oct. 13, 2020.
U.S. Appl. No. 17/068,865 entitled "Monitoring and Communicating Information Using Drug Administration Devices", filed Oct. 13, 2020.
U.S. Appl. No. 17/068,867 entitled "Aggregating and Analyzing Drug Administration Data", filed Oct. 13, 2020.
Van Baar et al., "Endoscopic duodenal mucosal resurfacing for the treatment of type 2 Diabetes mellitus: one year results from the first international, open label, prospective, multicentre study," Gut 2020, 69:295-303.
Yang et al., "4d printing reconfigurable, deployable and mechanically tunable materials," Material Science, 2019 (33 pages).
Zuo et al., "Pulmonary Intersegmental Places: Imaging Appearance and Possible Reasons Leading to Their Visualization," Radiology, vol. 267, No. 1, Apr. 2013, 267-275.
International Search Report and Written Opinion for International Application No. PCT/IB2022/059088, dated Dec. 8, 2022, 17 pages.
International Search Report and Written Opinion for International Application No. PCT/IB2022/059113 dated Feb. 14, 2023, 18 pages.

* cited by examiner

METHODS AND SYSTEMS FOR CONTROLLING COOPERATIVE SURGICAL INSTRUMENTS

CROSS-REFERENCE TO RELATED APPLICATIONS

This application claims priority to U.S. Provisional Patent Application No. 63/249,870, filed Sep. 29, 2021, and entitled "Methods and Systems for Controlling Cooperative Surgical Instruments," the disclosure of which is incorporated herein by reference in its entirety.

BACKGROUND

Some surgical procedures require the use of a plurality of surgical instruments operating on a region or portion of tissue at the same time to successfully execute the procedure. In some situations, due to anatomical limitations and/or the nature of the procedure, it is not possible for the plurality of surgical instruments to be in direct visual contact with one another even though they may be located in the same anatomic spaces. For example, during a procedure in which a shared tissue structure (e.g., a section of a patient's small intestine) is operated on, to successfully execute the procedure, the plurality of surgical instruments may need to be located in visually separated portions of the shared tissue structure.

However, in some implementations, a first surgical instrument for operating on a region of tissue and a second surgical instrument for operating on the region of tissue may be operated through independent systems even though the surgical instruments share a common surgical purpose. In such a scenario, it may be difficult or impossible for the first and second surgical instruments to be manipulated in cooperation to achieve a successful shared surgical outcome in situations where neither instrument can directly visualize movement of the other instrument but coordinated operation of the first and second surgical instruments is required to successfully execute a procedure.

Accordingly, there remains a need for improved methods and systems for controlling cooperative surgical instruments when direct visualization between the cooperative surgical instruments is restricted, for example by surrounding tissue.

SUMMARY

In an aspect, a system is provided that includes a first surgical instrument that is configured to be inserted into a first portion of a body cavity and to operate on a first surgical treatment site located within the body cavity of a patient. A second surgical instrument is also provided that is configured to be inserted into a second portion of the first body cavity and to operate on a second surgical treatment site located within the body cavity. The second portion of the body cavity is different than the first portion of the body cavity, and the second surgical treatment site is different than the first treatment tissue site. Furthermore, the system includes a first flexible endoscope that has a first image sensor that is configured to be positioned in the first portion of the body cavity such that the second surgical instrument is not within a field of view of the first image sensor. A second flexible endoscope is also provided that is configured to be positioned in the second portion of the body cavity such that the first surgical instrument is not within a field of view of the second image sensor. Additionally, the system includes a controller that is configured to receive images gathered by each of the first and second image sensors, to determine a first location of the first surgical instrument and a second location of the second surgical instrument, to determine a distance and orientation of the first surgical instrument relative to the second surgical instrument, and to cause movement of at least one of the first and second surgical instruments in the body cavity based on the determined distance and orientation.

The system can have numerous variations. For example, the first surgical treatment site can be adjacent to a first proximal anatomic landmark, the second surgical treatment site can be adjacent to a second distal anatomic landmark, and the first and second surgical treatment sites can be spaced apart from one another within the body cavity. In still other examples, the first proximal anatomic landmark can be a duodenojejunal flexure, and the second distal anatomic landmark can be an ileocecal valve.

In some embodiments, the first surgical instrument can be configured to be inserted into the body cavity through a first natural orifice of the patient, and the second surgical instrument can be configured to be inserted into the body cavity through a second, different natural orifice of the patient. In other examples, the controller can control a movement speed of at least one of the first and second surgical instruments within the body cavity based on at least the determined locations and distance. In still other examples, the system can include a first portion of a surgical implant that is configured to be releasably attached to the first surgical instrument and delivered into the body cavity while releasably attached to the first surgical instrument, and can include a second portion of the surgical implant configured to be releasably attached to the second surgical instrument and delivered into the body cavity while releasably attached to the second surgical instrument. In some examples, the controller can be configured to cause the movement of the at least one of the first and second surgical instruments before the delivery of the first and second portions of the surgical implants into the body cavity. In other examples, after the delivery of the first and second portions of the implant into the body cavity, the controller can be configured to at least one of move the first surgical instrument within the body cavity so as to move position the first portion of the surgical implant relative to the second portion of the surgical implant, and move the second surgical instrument within the body cavity so as to move position the second portion of the surgical implant relative to the first portion of the surgical implant. In some examples, the first portion of the surgical implant can include a first electromagnetic tracker configured to provide data regarding the first portion of the implant to the controller, and the second portion of the surgical implant can include a second electromagnetic tracker configured to provide data regarding the second portion of the implant to the controller. In some examples, the at least one of the movement of the first and second surgical instruments can be based on the received data regarding the first and second portions of the implant. In some examples, the body cavity can include a jejunum, and the surgical implant can include an anastomosis device.

In another aspect, a system is provided that includes at least one data processor and memory storing instructions that are configured to cause the at least one data processor to perform operations. The operations include receiving, in real time, from a first image sensor of a first flexible endoscopic system, first image data characterizing a first portion of a body cavity of a patient. The operations also include receiving, in real time, from a second image sensor of a second flexible endoscopic system, second image data characterizing a second portion of the body cavity, and the second portion of the body cavity is different than the first portion of the body cavity. The operations further include determining, based on the first image data, a first location of the first surgical instrument and determining based on the second image data, a second location of the second surgical instrument relative to the first surgical instrument. The operations also includes controlling advancement rates and advancement forces of the first and second surgical instruments, and the advancement rates and advancement forces are limited by detected proximities and orientations of distal ends of each of the first and second surgical instruments relative to one another.

The system can have a number of different variations. For instance, the first surgical treatment site can be adjacent to a first proximal anatomic landmark, the second surgical treatment site can be adjacent to a second distal anatomic landmark, and the first and second surgical treatment sites can be spaced apart from one another within the body cavity. In still another example, the first proximal anatomic landmark can be a duodenojejunal flexure, and the second the second distal anatomic landmark can be an ileocecal valve.

In some embodiments, the first surgical instrument can be configured to be inserted into the body cavity through a first natural orifice of the patient, and the second surgical instrument can be configured to be inserted into the body cavity through a second, different natural orifice of the patient. In one example, the operations of the at least one data processor further includes deploying a first portion of a surgical implant configured to be releasably attached to the first surgical instrument and delivered into the body cavity while releasably attached to the first surgical instrument, and deploying a second portion of the surgical implant configured to be releasably attached to the second surgical instrument and delivered into the body cavity while releasably attached to the second surgical instrument. In another example, the body cavity includes a jejunum, and the surgical implant includes an anastomosis device.

In another aspect, a method is provided that includes receiving, in real time, from a first image sensor of a first endoscopic system, first image data characterizing a first portion of a body cavity of a patient. The method also includes receiving, in real time, from a second image sensor of a second endoscopic system, second image data characterizing a second portion of the body cavity. The method further includes determining, based on the first image data, a first location of a first surgical instrument disposed within the first portion of a body cavity of the patient and configured to operate on a first surgical treatment site within the body cavity, and the first surgical instrument is outside of a field of view of the second endoscopic system. The method also includes determining, based on the second image data, a second location of a second surgical instrument relative to the first surgical instrument. The second surgical instrument is disposed within a second portion of the body cavity and is configured to operate on a second surgical treatment site within the body cavity, and the second surgical instrument is also outside of a field of view of the first endoscopic system. Additionally, the method includes determining a distance and orientation of the first surgical instrument relative to the second surgical instrument, and causing movement of at least one of the first and second surgical instruments in the body cavity based on the determined distance and orientation.

The method can have numerous variations. In one example, the method further includes advancing the first surgical instrument into the body cavity through a first natural orifice of the patient, and advancing the second surgical instrument into the body cavity through a second, different natural orifice of the patient. In another embodiment, the method includes determining orientations of first and second portions of a surgical implant releasably engaged with the first and second surgical instruments, respectively. In still another example, the method includes controlling a movement speed of the at least one of the first and second surgical instruments within the body cavity based on at least the determined locations and distance.

In another aspect, a system is provided that includes first and second surgical instruments and first and second flexible endoscopes. The first surgical instrument is configured to be inserted into a first portion of a body cavity and to operate on a first surgical treatment site located within the body cavity of a patient, and the second surgical instrument is configured to be inserted into a second portion of the body cavity and to operate on a second surgical treatment site located within the body cavity. Additionally, the second portion of the body cavity is different than the first portion of the body cavity, and the second surgical treatment site is different than the first treatment tissue site. Furthermore, the first flexible endoscope has a first image sensor and is configured to be positioned such that the second surgical instrument is not within a field of view of the first image sensor, and the second flexible endoscope has a second image sensor and is configured to be positioned such that the first surgical instrument is not within a field of view of the second image sensor. The system also has a controller that is configured to receive images gathered by each of the first and second image sensors, to determine a first location of the first surgical instrument and a second location of the second surgical instrument relative to one another, and to cause synchronized surgical actions between the first and second surgical instruments at the first and second treatment tissue sites, respectively.

The system can have numerous different variations. For example, the system can further include a first portion of a surgical implant that is configured to be releasably attached to the first surgical instrument and delivered into the body cavity while releasably attached to the first surgical instrument; and a second portion of the surgical implant that is configured to be releasably attached to the second surgical instrument and delivered into the body cavity while releasably attached to the second surgical instrument. In some examples, the controller can also be configured to actuate deployment of the first and second portions of the surgical implant simultaneously. In another example, the body cavity can include a jejunum, and the surgical implant can include an anastomosis device. In still another example, the first portion of the surgical implant can include a first electromagnetic tracker that is configured to provide data regarding the first portion of the implant to the controller, and the second portion of the surgical implant can include a second electromagnetic tracker that is configured to provide data regarding the second portion of the implant to the controller. In some examples, the simultaneous deployment of the first and second portions by the controller can be based on the received data regarding the first and second portions of the implant.

In another example, the system can include a third surgical instrument that is configured to be introduced into a third portion of the body cavity, and that is also configured to assist the controller to cause the synchronized surgical actions of the first and second surgical instruments. In another example, the first surgical instrument can be configured to be introduced into the patient through a first natural orifice of the patient, the second surgical instrument can be configured to be introduced into the patient through a second, different natural orifice of the patient, and the third surgical instrument can be configured to be introduced into the patient from a laparoscopic approach. In still another example, the synchronized surgical actions between the first and second surgical instruments can include simultaneous synchronized surgical actions at the first and second treatment tissue sites.

In some examples, the controller can be configured to cause the synchronized actions between the first and second surgical instruments when tissue obstructs the second surgical instrument from the field of view of the first endoscope, and when tissue obstructs the first surgical instrument from the field of view of the second endoscope.

In another aspect, a system is provided that includes at least one data processor and memory storing instructions that are configured to cause the at least one data processor to perform operations. The operations include receiving, in real time, from a first image sensor of a first endoscope, first image data characterizing a first portion of a body cavity of a patient. The operations also include receiving, in real time, from a second image sensor of a second endoscope, second image data characterizing a second portion of the body cavity. The operations further include determining, based on the first image data, a first location of a first surgical instrument that is configured to operate on tissue at a first surgical treatment site in the first portion of the body cavity. Furthermore, the first surgical instrument is outside of a field of view of the second endoscope. The operations also includes determining, based on the second image data, a second location of a second surgical instrument relative to the first location of the first surgical instrument. The second surgical instrument is configured to operate on tissue at a second surgical treatment site, and the second surgical instrument is outside of a field of view of the first endoscope. The operations also includes causing synchronized surgical actions between the first and second surgical instruments at the first and second treatment tissue sites, respectively.

The system can have numerous different variations. In one example, the synchronized surgical actions can include simultaneously deploying a first portion of a surgical implant from the first surgical instrument and a second portion of the surgical implant from the second surgical instrument. In still another example, the body cavity includes a jejunum, and the surgical implant includes a two-part magnetic anastomosis device. In still other examples, the system includes receiving, in real time, from a third image sensor of a third endoscope, third image data characterizing a third portion of the body cavity of the patient. In some examples, the synchronized surgical actions can include avoiding penetrating any tissue by the first and second surgical instruments.

In still another aspect, a method is provided that includes receiving, in real time, from a first image sensor of a first endoscopic system, first image data characterizing a first portion of a body cavity of a patient. The method also includes receiving, in real time, from a second image sensor of a second endoscopic system, second image data characterizing a second portion of the body cavity. The method also includes determining, by a controller, based on the first image data, a first location of a first surgical instrument that manipulates tissue at a first surgical treatment site disposed within the first portion of the body cavity of the patient, and the first surgical instrument is outside of a field of view of the second endoscopic system. The method further includes determining, by the controller, based on the second image data, a second location of a second surgical instrument relative to the first surgical instrument. The second surgical instrument manipulates tissue at a second surgical treatment site disposed within the second portion of the body cavity, and the second surgical instrument is outside of a field of view of the first endoscopic system. The method further includes causing, by the controller, synchronized surgical actions between the first and second surgical instruments at the first and second treatment tissue sites, respectively.

The method can nave numerous different variations. For example, the method can further include deploying a first portion of a surgical implant that is configured to be releasably attached to the first surgical instrument and delivered into the body cavity while releasably attached to the first surgical instrument, and deploying a second portion of the surgical implant that is configured to be releasably attached to the second surgical instrument and delivered into the body cavity while releasably attached to the second surgical instrument. In another example, the body cavity includes a jejunum, and the surgical implant includes a two-part magnetic anastomosis device. In still another example, the method further includes receiving, in real time, from a third image sensor of a third endoscope, third image data characterizing a third portion of the body cavity of the patient.

In another aspect, a system is provide that includes a first surgical instrument that is configured to be inserted into a first portion of a body cavity and to deploy a first portion of a surgical implant within the body cavity of a patient. The system also includes a second surgical instrument that is configured to be inserted into a second portion of the body cavity and to deploy a second portion of the surgical implant within the body cavity, and the second portion of the body cavity is different than the first portion. The system further includes a first flexible endoscope that has a first image sensor, and the first flexible endoscope is positioned such that the second surgical instrument is not within a field of view of the first image sensor. The system also has a second flexible endoscope with a second image sensor, and the second flexible endoscope is positioned such that the first surgical instrument is not within a field of view of the second image sensor. The system also includes a controller that is configured to receive images gathered by each of the first and second image sensors, to determine a first location of the first surgical instrument and a second location of the second surgical instrument relative to one another, to determine properties of the tissue walls within the first and second portions of the first body cavity, and to determine a placement location of the first and second portions of the surgical implant based on the properties of the tissue walls.

The system can have a number of variations. For example, the first portion of the surgical implant can include a first electromagnetic tracker that is configured to provide data regarding the first portion of the implant to the controller, and the second portion of the surgical implant can include a second electromagnetic tracker that is configured to provide data regarding the second portion of the implant to the controller. In some examples, the determined placement location of the first and second portions of the surgical implant can be based at least on the received data regarding the first and second portions of the implant. In another example, the properties of the tissue walls can include at least one of thickness, stiffness, or tissue composition. In another example, the controller can be configured to determine the thickness of the tissue walls based on at least the first and second locations of the first and second instruments. In still another example, the controller can be configured to determine the properties of the tissue walls based on at least one of tissue impedance and non-visual light spectrum imaging.

In some embodiments, the controller can be configured to determine the locations of the first and second surgical instruments when tissue obstructs the second surgical instrument from the field of view of the first endoscope and when tissue obstructs the first surgical instrument from the field of view of the second endoscope. In some examples, the first surgical instrument can be configured to be inserted into the body cavity through a first natural orifice of the patient, and the second surgical instrument can be configured to be inserted into the body cavity through a second, different natural orifice of the patient. In other examples, the controller is configured to rotate and articulate the first surgical instrument to position the first portion of the surgical implant relative to the second portion of the surgical implant. In still other examples, the body cavity can include a jejunum, and the surgical implant can include a two-part magnetic anastomosis device.

In another aspect, a system is provided that has at least one data processor and memory storing instructions that are configured to cause the at least one data processor to perform operations. The operations include receiving, in real time, from a first image sensor of a first endoscope, first image data characterizing a first portion of a body cavity of a patient. The operations also include receiving, in real time, from a second image sensor of a second endoscope, second image data characterizing a second portion of the first body cavity. Furthermore, the operations include determining, based on the first image data, a first location of a first surgical instrument that is configured to deploy a first portion of a surgical implant in the first portion of the body cavity. The operations also include determining, based on the second image data, a second location of a second surgical instrument relative to the first location of the first surgical instrument, and the second surgical instrument is configured to deploy a second portion of a surgical implant in the second portion of the body cavity. The operations also include determining properties of the tissue walls within the first and second portions of the first body cavity, and include determining placement locations of the first and second portions of the surgical implant based on the properties of the tissue walls.

The system can have a number of different variations. For example, the operations of the at least one data processor can include receiving data from a first electromagnetic tracker in the first portion of the surgical implant regarding the first portion of the implant to the controller, and receiving data from a second electromagnetic tracker in the second portion of the surgical implant regarding the second portion of the implant to the controller. In some examples, the operations can also include determining placement locations of the first and second portions of the surgical implant based on at least the data received from the first and second electromagnetic trackers. In another example, the properties of the tissue walls can include at least one of thickness, stiffness, or tissue composition. In another example, the system can include determining the properties of the tissue walls based on at least one of the first and second locations of the first and second instruments, tissue impedance, and non-visual light spectrum imaging. In still another example, the system can include determining the first location of the first surgical instrument and determining the second location of the second surgical instrument when tissue obstructs the second surgical instrument from the field of view of the first endoscope and when tissue obstructs the first surgical instrument from the field of view of the second endoscope. In another example, the body cavity can include a jejunum, and the surgical implant can include an anastomosis device.

In still another aspect, a method is provided that includes receiving, in real time, from a first image sensor of a first endoscopic system, first image data characterizing a first portion of a body cavity of a patient. The method also includes receiving, in real time, from a second image sensor of a second endoscopic system, second image data characterizing a second portion of the first hollow organ. The method also includes determining, by a controller, based on the first image data, a first location of a first surgical instrument within the first body portion and having a first portion of a surgical implant releasably engaged thereon. The first surgical instrument is outside of a field of view of the second endoscopic system. Furthermore, the second portion of the body cavity is different than the first portion, and the second surgical treatment site of the body cavity is different from the first surgical treatment site. The method further includes determining, by the controller, based on the second image data, a second location of a second surgical instrument within the second portion of the body cavity relative to the first surgical instrument. Additionally, the second surgical instrument has a second portion of a surgical implant that is releasably engaged thereon, and the second surgical instrument is outside of a field of view of the first endoscopic system. The method further includes determining, by the controller, properties of the tissue walls within the first and second portions of the first body cavity, and includes determining, by the controller, placement locations of the first and second portions of the surgical implant based on the properties of the tissue walls.

The method can have numerous different variations. For example, the properties of the tissue walls can include at least one of thickness, stiffness, or tissue composition. In another example, the method can include determining the properties of the tissue walls based on at least one of the first and second locations of the first and second instruments, tissue impedance, and non-visual light spectrum imaging. In still another example, the method can also include determining the first location of the first surgical instrument and determining the second location of the second surgical instrument when tissue obstructs the second surgical instrument from the field of view of the first endoscope and when tissue obstructs the first surgical instrument from the field of view of the second endoscope. In still yet another example, the body cavity can include a jejunum, and the surgical implant can include an anastomosis device.

BRIEF DESCRIPTION OF DRAWINGS

The present invention is described by way of reference to the accompanying figures which are as follows.

DETAILED DESCRIPTION

Figure 1:
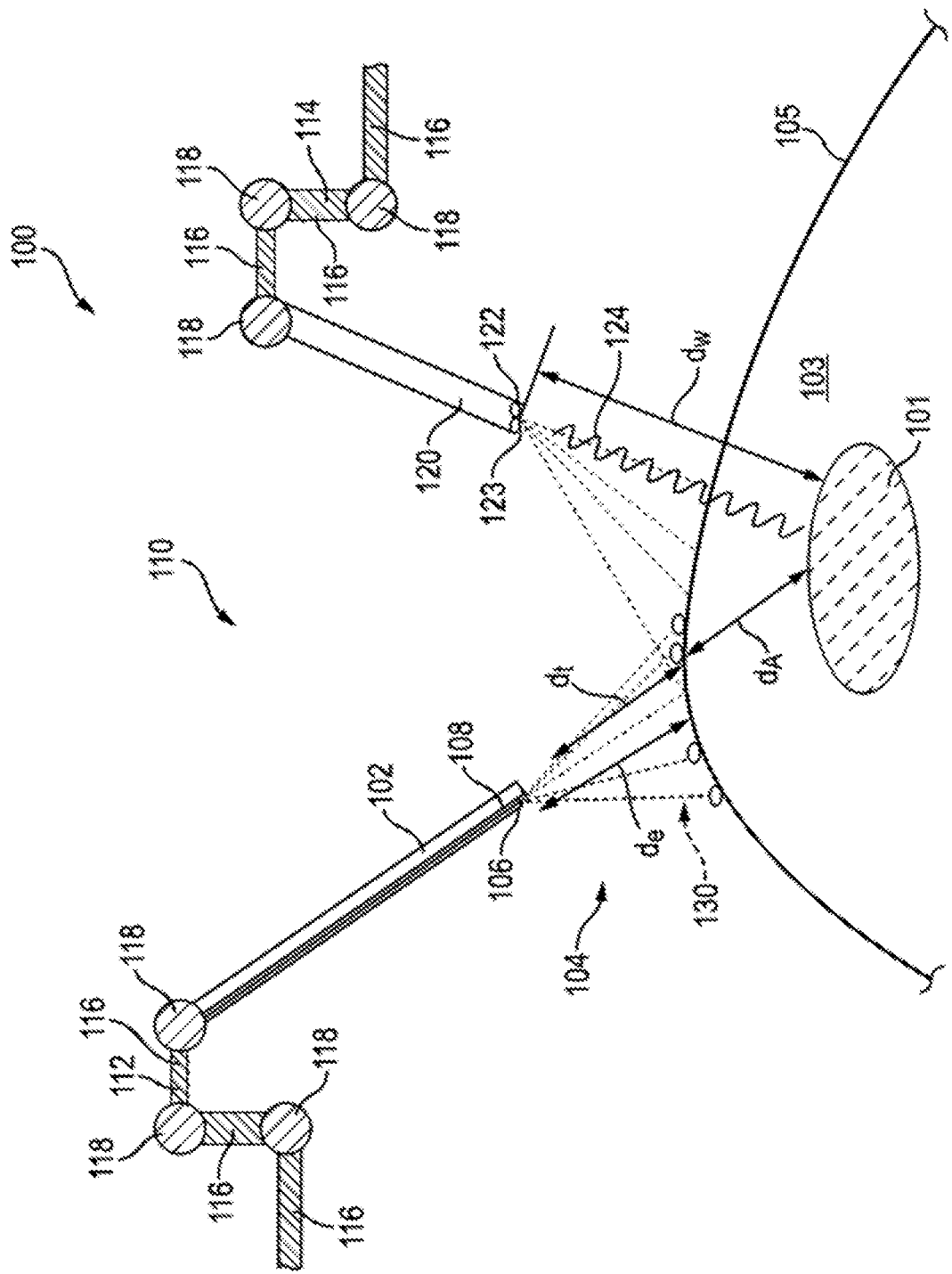
FIG. 1 is a schematic view of one embodiment of a surgical visualization system.

Certain exemplary embodiments will now be described to provide an overall understanding of the principles of the structure, function, manufacture, and use of the devices, systems, and methods disclosed herein. One or more examples of these embodiments are illustrated in the accompanying drawings. A person skilled in the art will understand that the devices, systems, and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Further, in the present disclosure, like-named components of the embodiments generally have similar features, and thus within a particular embodiment each feature of each like-named component is not necessarily fully elaborated upon. Additionally, to the extent that linear or circular dimensions are used in the description of the disclosed systems, devices, and methods, such dimensions are not intended to limit the types of shapes that can be used in conjunction with such systems, devices, and methods. A person skilled in the art will recognize that an equivalent to such linear and circular dimensions can easily be determined for any geometric shape. A person skilled in the art will appreciate that a dimension may not be a precise value but nevertheless be considered to be at about that value due to any number of factors such as manufacturing tolerances and sensitivity of measurement equipment. Sizes and shapes of the systems and devices, and the components thereof, can depend at least on the size and shape of components with which the systems and devices will be used.

Surgical Visualization

In general, a surgical visualization system is configured to leverage "digital surgery" to obtain additional information about a patient's anatomy and/or a surgical procedure. The surgical visualization system is further configured to convey data to one or more medical practitioners in a helpful manner. Various aspects of the present disclosure provide improved visualization of the patient's anatomy and/or the surgical procedure, and/or use visualization to provide improved control of a surgical tool (also referred to herein as a "surgical device" or a "surgical instrument").

"Digital surgery" can embrace robotic systems, advanced imaging, advanced instrumentation, artificial intelligence, machine learning, data analytics for performance tracking and benchmarking, connectivity both inside and outside of the operating room (OR), and more. Although various surgical visualization systems described herein can be used in combination with a robotic surgical system, surgical visualization systems are not limited to use with a robotic surgical system. In certain instances, surgical visualization using a surgical visualization system can occur without robotics and/or with limited and/or optional robotic assistance. Similarly, digital surgery can occur without robotics and/or with limited and/or optional robotic assistance.

In certain instances, a surgical system that incorporates a surgical visualization system may enable smart dissection in order to identify and avoid critical structures. Critical structures include anatomical structures such as a ureter, an artery such as a superior mesenteric artery, a vein such as a portal vein, a nerve such as a phrenic nerve, and/or a tumor, among other anatomical structures. In other instances, a critical structure can be a foreign structure in the anatomical field, such as a surgical device, a surgical fastener, a clip, a tack, a bougie, a band, a plate, and other foreign structures. Critical structures can be determined on a patient-by-patient and/or a procedure-by-procedure basis. Smart dissection technology may provide, for example, improved intraoperative guidance for dissection and/or may enable smarter decisions with critical anatomy detection and avoidance technology.

A surgical system incorporating a surgical visualization system may enable smart anastomosis technologies that provide more consistent anastomoses at optimal location(s) with improved workflow. Cancer localization technologies may be improved with a surgical visualization platform. For example, cancer localization technologies can identify and track a cancer location, orientation, and its margins. In certain instances, the cancer localization technologies may compensate for movement of a surgical instrument, a patient, and/or the patient's anatomy during a surgical procedure in order to provide guidance back to the point of interest for medical practitioner(s).

A surgical visualization system may provide improved tissue characterization and/or lymph node diagnostics and mapping. For example, tissue characterization technologies may characterize tissue type and health without the need for physical haptics, especially when dissecting and/or placing stapling devices within the tissue. Certain tissue characterization technologies may be utilized without ionizing radiation and/or contrast agents. With respect to lymph node diagnostics and mapping, a surgical visualization platform may, for example, preoperatively locate, map, and ideally diagnose the lymph system and/or lymph nodes involved in cancerous diagnosis and staging.

During a surgical procedure, information available to a medical practitioner via the "naked eye" and/or an imaging system may provide an incomplete view of the surgical site. For example, certain structures, such as structures embedded or buried within an organ, can be at least partially concealed or hidden from view. Additionally, certain dimensions and/or relative distances can be difficult to ascertain with existing sensor systems and/or difficult for the "naked eye" to perceive. Moreover, certain structures can move pre-operatively (e.g., before a surgical procedure but after a preoperative scan) and/or intraoperatively. In such instances, the medical practitioner can be unable to accurately determine the location of a critical structure intraoperatively.

When the position of a critical structure is uncertain and/or when the proximity between the critical structure and a surgical tool is unknown, a medical practitioner's decision-making process can be inhibited. For example, a medical practitioner may avoid certain areas in order to avoid inadvertent dissection of a critical structure; however, the avoided area may be unnecessarily large and/or at least partially misplaced. Due to uncertainty and/or overly/excessive exercises in caution, the medical practitioner may not access certain desired regions. For example, excess caution may cause a medical practitioner to leave a portion of a tumor and/or other undesirable tissue in an effort to avoid a critical structure even if the critical structure is not in the particular area and/or would not be negatively impacted by the medical practitioner working in that particular area. In certain instances, surgical results can be improved with increased knowledge and/or certainty, which can allow a surgeon to be more accurate and, in certain instances, less conservative/more aggressive with respect to particular anatomical areas.

A surgical visualization system can allow for intraoperative identification and avoidance of critical structures. The surgical visualization system may thus enable enhanced intraoperative decision making and improved surgical outcomes. The surgical visualization system can provide advanced visualization capabilities beyond what a medical practitioner sees with the "naked eye" and/or beyond what an imaging system can recognize and/or convey to the medical practitioner. The surgical visualization system can augment and enhance what a medical practitioner is able to know prior to tissue treatment (e.g., dissection, etc.) and, thus, may improve outcomes in various instances. As a result, the medical practitioner can confidently maintain momentum throughout the surgical procedure knowing that the surgical visualization system is tracking a critical structure, which may be approached during dissection, for example. The surgical visualization system can provide an indication to the medical practitioner in sufficient time for the medical practitioner to pause and/or slow down the surgical procedure and evaluate the proximity to the critical structure to prevent inadvertent damage thereto. The surgical visualization system can provide an ideal, optimized, and/or customizable amount of information to the medical practitioner to allow the medical practitioner to move confidently and/or quickly through tissue while avoiding inadvertent damage to healthy tissue and/or critical structure(s) and, thus, to minimize the risk of harm resulting from the surgical procedure.

Surgical visualization systems are described in detail below. In general, a surgical visualization system can include a first light emitter configured to emit a plurality of spectral waves, a second light emitter configured to emit a light pattern, and a receiver, or sensor, configured to detect visible light, molecular responses to the spectral waves (spectral imaging), and/or the light pattern. The surgical visualization system can also include an imaging system and a control circuit in signal communication with the receiver and the imaging system. Based on output from the receiver, the control circuit can determine a geometric surface map, e.g., three-dimensional surface topography, of the visible surfaces at the surgical site and a distance with respect to the surgical site, such as a distance to an at least partially concealed structure. The imaging system can convey the geometric surface map and the distance to a medical practitioner. In such instances, an augmented view of the surgical site provided to the medical practitioner can provide a representation of the concealed structure within the relevant context of the surgical site. For example, the imaging system can virtually augment the concealed structure on the geometric surface map of the concealing and/or obstructing tissue similar to a line drawn on the ground to indicate a utility line below the surface. Additionally or alternatively, the imaging system can convey the proximity of a surgical tool to the visible and obstructing tissue and/or to the at least partially concealed structure and/or a depth of the concealed structure below the visible surface of the obstructing tissue. For example, the visualization system can determine a distance with respect to the augmented line on the surface of the visible tissue and convey the distance to the imaging system.

Throughout the present disclosure, any reference to "light," unless specifically in reference to visible light, can include electromagnetic radiation (EMR) or photons in the visible and/or non-visible portions of the EMR wavelength spectrum. The visible spectrum, sometimes referred to as the optical spectrum or luminous spectrum, is that portion of the electromagnetic spectrum that is visible to (e.g., can be detected by) the human eye and may be referred to as "visible light" or simply "light." A typical human eye will respond to wavelengths in air that are from about 380 nm to about 750 nm. The invisible spectrum (e.g., the non-luminous spectrum) is that portion of the electromagnetic spectrum that lies below and above the visible spectrum. The invisible spectrum is not detectable by the human eye. Wavelengths greater than about 750 nm are longer than the red visible spectrum, and they become invisible infrared (IR), microwave, and radio electromagnetic radiation. Wavelengths less than about 380 nm are shorter than the violet spectrum, and they become invisible ultraviolet, x-ray, and gamma ray electromagnetic radiation.

FIG. 1 illustrates one embodiment of a surgical visualization system 100. The surgical visualization system 100 is configured to create a visual representation of a critical structure 101 within an anatomical field. The critical structure 101 can include a single critical structure or a plurality of critical structures. As discussed herein, the critical structure 101 can be any of a variety of structures, such as an anatomical structure, e.g., a ureter, an artery such as a superior mesenteric artery, a vein such as a portal vein, a nerve such as a phrenic nerve, a vessel, a tumor, or other anatomical structure, or a foreign structure, e.g., a surgical device, a surgical fastener, a surgical clip, a surgical tack, a bougie, a surgical band, a surgical plate, or other foreign structure. As discussed herein, the critical structure 101 can be identified on a patient-by-patient and/or a procedure-by-procedure basis. Embodiments of critical structures and of identifying critical structures using a visualization system are further described in U.S. Pat. No. 10,792,034 entitled "Visualization Of Surgical Devices" issued Oct. 6, 2020, which is hereby incorporated by reference in its entirety.

In some instances, the critical structure 101 can be embedded in tissue 103. The tissue 103 can be any of a variety of tissues, such as fat, connective tissue, adhesions, and/or organs. Stated differently, the critical structure 101 may be positioned below a surface 105 of the tissue 103. In such instances, the tissue 103 conceals the critical structure 101 from the medical practitioner's "naked eye" view. The tissue 103 also obscures the critical structure 101 from the view of an imaging device 120 of the surgical visualization system 100. Instead of being fully obscured, the critical structure 101 can be partially obscured from the view of the medical practitioner and/or the imaging device 120.

The surgical visualization system 100 can be used for clinical analysis and/or medical intervention. In certain instances, the surgical visualization system 100 can be used intraoperatively to provide real-time information to the medical practitioner during a surgical procedure, such as real-time information regarding proximity data, dimensions, and/or distances. A person skilled in the art will appreciate that information may not be precisely real time but nevertheless be considered to be real time for any of a variety of reasons, such as time delay induced by data transmission, time delay induced by data processing, and/or sensitivity of measurement equipment. The surgical visualization system 100 is configured for intraoperative identification of critical structure(s) and/or to facilitate the avoidance of the critical structure(s) 101 by a surgical device. For example, by identifying the critical structure 101, a medical practitioner can avoid maneuvering a surgical device around the critical structure 101 and/or a region in a predefined proximity of the critical structure 101 during a surgical procedure. For another example, by identifying the critical structure 101, a medical practitioner can avoid dissection of and/or near the critical structure 101, thereby helping to prevent damage to the critical structure 101 and/or helping to prevent a surgical device being used by the medical practitioner from being damaged by the critical structure 101.

The surgical visualization system 100 is configured to incorporate tissue identification and geometric surface mapping in combination with the surgical visualization system's distance sensor system 104. In combination, these features of the surgical visualization system 100 can determine a position of a critical structure 101 within the anatomical field and/or the proximity of a surgical device 102 to the surface 105 of visible tissue 103 and/or to the critical structure 101. Moreover, the surgical visualization system 100 includes an imaging system that includes the imaging device 120 configured to provide real-time views of the surgical site. The imaging device 120 can include, for example, a spectral camera (e.g., a hyperspectral camera, multispectral camera, or selective spectral camera), which is configured to detect reflected spectral waveforms and generate a spectral cube of images based on the molecular response to the different wavelengths. Views from the imaging device 120 can be provided in real time to a medical practitioner, such as on a display (e.g., a monitor, a computer tablet screen, etc.). The displayed views can be augmented with additional information based on the tissue identification, landscape mapping, and the distance sensor system 104. In such instances, the surgical visualization system 100 includes a plurality of subsystems—an imaging subsystem, a surface mapping subsystem, a tissue identification subsystem, and/or a distance determining subsystem. These subsystems can cooperate to intra-operatively provide advanced data synthesis and integrated information to the medical practitioner.

The imaging device 120 can be configured to detect visible light, spectral light waves (visible or invisible), and a structured light pattern (visible or invisible). Examples of the imaging device 120 includes scopes, e.g., an endoscope, an arthroscope, an angioscope, a bronchoscope, a choledochoscope, a colonoscope, a cytoscope, a duodenoscope, an enteroscope, an esophagogastro-duodenoscope (gastroscope), a laryngoscope, a nasopharyngo-neproscope, a sigmoidoscope, a thoracoscope, an ureteroscope, or an exoscope. Scopes can be particularly useful in minimally invasive surgical procedures. In open surgery applications, the imaging device 120 may not include a scope.

The tissue identification subsystem can be achieved with a spectral imaging system. The spectral imaging system can rely on imaging such as hyperspectral imaging, multispectral imaging, or selective spectral imaging. Embodiments of hyperspectral imaging of tissue are further described in U.S. Pat. No. 9,274,047 entitled "System And Method For Gross Anatomic Pathology Using Hyperspectral Imaging" issued Mar. 1, 2016, which is hereby incorporated by reference in its entirety.

The surface mapping subsystem can be achieved with a light pattern system. Various surface mapping techniques using a light pattern (or structured light) for surface mapping can be utilized in the surgical visualization systems described herein. Structured light is the process of projecting a known pattern (often a grid or horizontal bars) on to a surface. In certain instances, invisible (or imperceptible) structured light can be utilized, in which the structured light is used without interfering with other computer vision tasks for which the projected pattern may be confusing. For example, infrared light or extremely fast frame rates of visible light that alternate between two exact opposite patterns can be utilized to prevent interference. Embodiments of surface mapping and a surgical system including a light source and a projector for projecting a light pattern are further described in U.S. Pat. Pub. No. 2017/0055819 entitled "Set Comprising A Surgical Instrument" published Mar. 2, 2017, U.S. Pat. Pub. No. 2017/0251900 entitled "Depiction System" published Sep. 7, 2017, and U.S. patent application Ser. No. 16/729,751 entitled "Surgical Systems For Generating Three Dimensional Constructs Of Anatomical Organs And Coupling Identified Anatomical Structures Thereto" filed Dec. 30, 2019, which are hereby incorporated by reference in their entireties.

The distance determining system can be incorporated into the surface mapping system. For example, structured light can be utilized to generate a three-dimensional (3D) virtual model of the visible surface 105 and determine various distances with respect to the visible surface 105. Additionally or alternatively, the distance determining system can rely on time-of-flight measurements to determine one or more distances to the identified tissue (or other structures) at the surgical site.

The surgical visualization system 100 also includes a surgical device 102. The surgical device 102 can be any suitable surgical device. Examples of the surgical device 102 includes a surgical dissector, a surgical stapler, a surgical grasper, a clip applier, a smoke evacuator, a surgical energy device (e.g., mono-polar probes, bi-polar probes, ablation probes, an ultrasound device, an ultrasonic end effector, etc.), etc. In some embodiments, the surgical device 102 includes an end effector having opposing jaws that extend from a distal end of a shaft of the surgical device 102 and that are configured to engage tissue therebetween.

The surgical visualization system 100 can be configured to identify the critical structure 101 and a proximity of the surgical device 102 to the critical structure 101. The imaging device 120 of the surgical visualization system 100 is configured to detect light at various wavelengths, such as visible light, spectral light waves (visible or invisible), and a structured light pattern (visible or invisible). The imaging device 120 can include a plurality of lenses, sensors, and/or receivers for detecting the different signals. For example, the imaging device 120 can be a hyperspectral, multispectral, or selective spectral camera, as described herein. The imaging device 120 can include a waveform sensor 122 (such as a spectral image sensor, detector, and/or three-dimensional camera lens). For example, the imaging device 120 can include a right-side lens and a left-side lens used together to record two two-dimensional images at the same time and, thus, generate a three-dimensional (3D) image of the surgical site, render a three-dimensional image of the surgical site, and/or determine one or more distances at the surgical site. Additionally or alternatively, the imaging device 120 can be configured to receive images indicative of the topography of the visible tissue and the identification and position of hidden critical structures, as further described herein. For example, a field of view of the imaging device 120 can overlap with a pattern of light (structured light) on the surface 105 of the tissue 103, as shown in FIG. 1.

As in this illustrated embodiment, the surgical visualization system 100 can be incorporated into a robotic surgical system 110. The robotic surgical system 110 can have a variety of configurations, as discussed herein. In this illustrated embodiment, the robotic surgical system 110 includes a first robotic arm 112 and a second robotic arm 114. The robotic arms 112, 114 each include rigid structural members 116 and joints 118, which can include servomotor controls. The first robotic arm 112 is configured to maneuver the surgical device 102, and the second robotic arm 114 is configured to maneuver the imaging device 120. A robotic control unit of the robotic surgical system 110 is configured to issue control motions to the first and second robotic arms 112, 114, which can affect the surgical device 102 and the imaging device 120, respectively.

In some embodiments, one or more of the robotic arms 112, 114 can be separate from the main robotic system 110 used in the surgical procedure. For example, at least one of the robotic arms 112, 114 can be positioned and registered to a particular coordinate system without a servomotor control. For example, a closed-loop control system and/or a plurality of sensors for the robotic arms 112, 114 can control and/or register the position of the robotic arm(s) 112, 114 relative to the particular coordinate system. Similarly, the position of the surgical device 102 and the imaging device 120 can be registered relative to a particular coordinate system.

Examples of robotic surgical systems include the Ottava™ robotic-assisted surgery system (Johnson & Johnson of New Brunswick, NJ), da Vinci® surgical systems (Intuitive Surgical, Inc. of Sunnyvale, CA), the Hugo™ robotic-assisted surgery system (Medtronic PLC of Minneapolis, MN), the Versius® surgical robotic system (CMR Surgical Ltd of Cambridge, UK), and the Monarch® platform (Auris Health, Inc. of Redwood City, CA). Embodiments of various robotic surgical systems and using robotic surgical systems are further described in U.S. Pat. Pub. No. 2018/0177556 entitled "Flexible Instrument Insertion Using An Adaptive Force Threshold" filed Dec. 28, 2016, U.S. Pat. Pub. No. 2020/0000530 entitled "Systems And Techniques For Providing Multiple Perspectives During Medical Procedures" filed Apr. 16, 2019, U.S. Pat. Pub. No. 2020/0170720 entitled "Image-Based Branch Detection And Mapping For Navigation" filed Feb. 7, 2020, U.S. Pat. Pub. No. 2020/0188043 entitled "Surgical Robotics System" filed Dec. 9, 2019, U.S. Pat. Pub. No. 2020/0085516 entitled "Systems And Methods For Concomitant Medical Procedures" filed Sep. 3, 2019, U.S. Pat. No. 8,831,782 entitled "Patient-Side Surgeon Interface For A Teleoperated Surgical Instrument" filed Jul. 15, 2013, and Intl. Pat. Pub. No. WO 2014151621 entitled "Hyperdexterous Surgical System" filed Mar. 13, 2014, which are hereby incorporated by reference in their entireties.

The surgical visualization system 100 also includes an emitter 106. The emitter 106 is configured to emit a pattern of light, such as stripes, grid lines, and/or dots, to enable the determination of the topography or landscape of the surface 105. For example, projected light arrays 130 can be used for three-dimensional scanning and registration on the surface 105. The projected light arrays 130 can be emitted from the emitter 106 located on the surgical device 102 and/or one of the robotic arms 112, 114 and/or the imaging device 120. In one aspect, the projected light array 130 is employed by the surgical visualization system 100 to determine the shape defined by the surface 105 of the tissue 103 and/or motion of the surface 105 intraoperatively. The imaging device 120 is configured to detect the projected light arrays 130 reflected from the surface 105 to determine the topography of the surface 105 and various distances with respect to the surface 105.

As in this illustrated embodiment, the imaging device 120 can include an optical waveform emitter 123, such as by being mounted on or otherwise attached on the imaging device 120. The optical waveform emitter 123 is configured to emit electromagnetic radiation 124 (near-infrared (NIR) photons) that can penetrate the surface 105 of the tissue 103 and reach the critical structure 101. The imaging device 120 and the optical waveform emitter 123 can be positionable by the robotic arm 114. The optical waveform emitter 123 is mounted on or otherwise on the imaging device 122 but in other embodiments can be positioned on a separate surgical device from the imaging device 120. A corresponding waveform sensor 122 (e.g., an image sensor, spectrometer, or vibrational sensor) of the imaging device 120 is configured to detect the effect of the electromagnetic radiation received by the waveform sensor 122. The wavelengths of the electromagnetic radiation 124 emitted by the optical waveform emitter 123 are configured to enable the identification of the type of anatomical and/or physical structure, such as the critical structure 101. The identification of the critical structure 101 can be accomplished through spectral analysis, photo-acoustics, and/or ultrasound, for example. In one aspect, the wavelengths of the electromagnetic radiation 124 can be variable. The waveform sensor 122 and optical waveform emitter 123 can be inclusive of a multispectral imaging system and/or a selective spectral imaging system, for example. In other instances, the waveform sensor 122 and optical waveform emitter 123 can be inclusive of a photoacoustic imaging system, for example.

The distance sensor system 104 of the surgical visualization system 100 is configured to determine one or more distances at the surgical site. The distance sensor system 104 can be a time-of-flight distance sensor system that includes an emitter, such as the emitter 106 as in this illustrated embodiment, and that includes a receiver 108. In other instances, the time-of-flight emitter can be separate from the structured light emitter. The emitter 106 can include a very tiny laser source, and the receiver 108 can include a matching sensor. The distance sensor system 104 is configured to detect the "time of flight," or how long the laser light emitted by the emitter 106 has taken to bounce back to the sensor portion of the receiver 108. Use of a very narrow light source in the emitter 106 enables the distance sensor system 104 to determining the distance to the surface 105 of the tissue 103 directly in front of the distance sensor system 104.

The receiver 108 of the distance sensor system 104 is positioned on the surgical device 102 in this illustrated embodiment, but in other embodiments the receiver 108 can be mounted on a separate surgical device instead of the surgical device 102. For example, the receiver 108 can be mounted on a cannula or trocar through which the surgical device 102 extends to reach the surgical site. In still other embodiments, the receiver 108 for the distance sensor system 104 can be mounted on a separate robotically-controlled arm of the robotic system 110 (e.g., on the second robotic arm 114) than the first robotic arm 112 to which the surgical device 102 is coupled, can be mounted on a movable arm that is operated by another robot, or be mounted to an operating room (OR) table or fixture. In some embodiments, the imaging device 120 includes the receiver 108 to allow for determining the distance from the emitter 106 to the surface 105 of the tissue 103 using a line between the emitter 106 on the surgical device 102 and the imaging device 120. For example, the distance $d_e$ can be triangulated based on known positions of the emitter 106 (on the surgical device 102) and the receiver 108 (on the imaging device 120) of the distance sensor system 104. The three-dimensional position of the receiver 108 can be known and/or registered to the robot coordinate plane intraoperatively.

As in this illustrated embodiment, the position of the emitter 106 of the distance sensor system 104 can be controlled by the first robotic arm 112, and the position of the receiver 108 of the distance sensor system 104 can be controlled by the second robotic arm 114. In other embodiments, the surgical visualization system 100 can be utilized apart from a robotic system. In such instances, the distance sensor system 104 can be independent of the robotic system.

In FIG. 1, $d_e$ is emitter-to-tissue distance from the emitter 106 to the surface 105 of the tissue 103, and $d_t$ is device-to-tissue distance from a distal end of the surgical device 102 to the surface 105 of the tissue 103. The distance sensor system 104 is configured to determine the emitter-to-tissue distance $d_e$. The device-to-tissue distance $d_t$ is obtainable from the known position of the emitter 106 on the surgical device 102, e.g., on a shaft thereof proximal to the surgical device's distal end, relative to the distal end of the surgical device 102. In other words, when the distance between the emitter 106 and the distal end of the surgical device 102 is known, the device-to-tissue distance $d_t$ can be determined from the emitter-to-tissue distance $d_e$. In some embodiments, the shaft of the surgical device 102 can include one or more articulation joints and can be articulatable with respect to the emitter 106 and jaws at the distal end of the surgical device 102. The articulation configuration can include a multi-joint vertebrae-like structure, for example. In some embodiments, a three-dimensional camera can be utilized to triangulate one or more distances to the surface 105.

In FIG. 1, $d_w$ is camera-to-critical structure distance from the optical waveform emitter 123 located on the imaging device 120 to the surface of the critical structure 101, and $d_A$ is a depth of the critical structure 101 below the surface 105 of the tissue 103 (e.g., the distance between the portion of the surface 105 closest to the surgical device 102 and the critical structure 101). The time-of-flight of the optical waveforms emitted from the optical waveform emitter 123 located on the imaging device 120 are configured to determine the camera-to-critical structure distance $d_w$.

Figure 2:
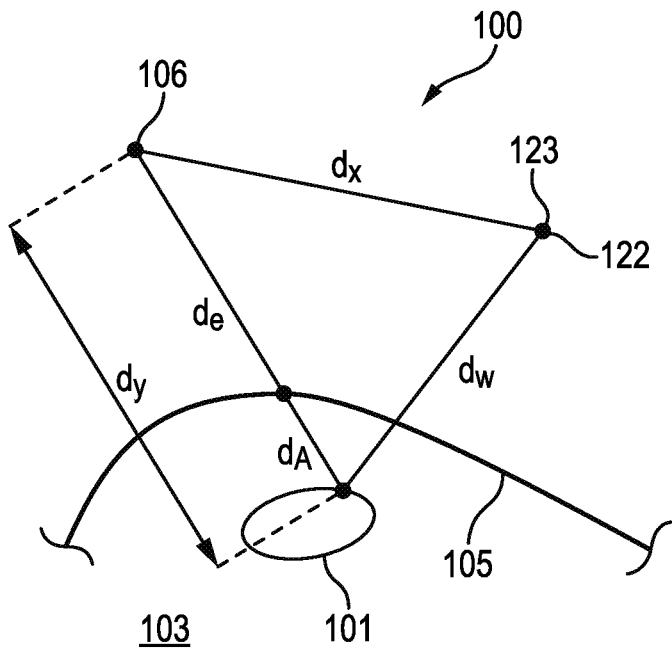
FIG. 2 is a schematic view of triangularization between a surgical device, an imaging device, and a critical structure of FIG. 1.

As shown in FIG. 2, the depth $d_A$ of the critical structure 101 relative to the surface 105 of the tissue 103 can be determined by triangulating from the distance $d_w$ and known positions of the emitter 106 on the surgical device 102 and the optical waveform emitter 123 on the imaging device 120 (and, thus, the known distance $d_x$ therebetween) to determine the distance $d_y$, which is the sum of the distances $d_e$ and $d_A$. Additionally or alternatively, time-of-flight from the optical waveform emitter 123 can be configured to determine the distance from the optical waveform emitter 123 to the surface 105 of the tissue 103. For example, a first waveform (or range of waveforms) can be utilized to determine the camera-to-critical structure distance $d_w$ and a second waveform (or range of waveforms) can be utilized to determine the distance to the surface 105 of the tissue 103. In such instances, the different waveforms can be utilized to determine the depth of the critical structure 101 below the surface 105 of the tissue 103.

Additionally or alternatively, the distance $d_A$ can be determined from an ultrasound, a registered magnetic resonance imaging (MRI), or computerized tomography (CT) scan. In still other instances, the distance $d_A$ can be determined with spectral imaging because the detection signal received by the imaging device 120 can vary based on the type of material, e.g., type of the tissue 103. For example, fat can decrease the detection signal in a first way, or a first amount, and collagen can decrease the detection signal in a different, second way, or a second amount.

Figure 3:
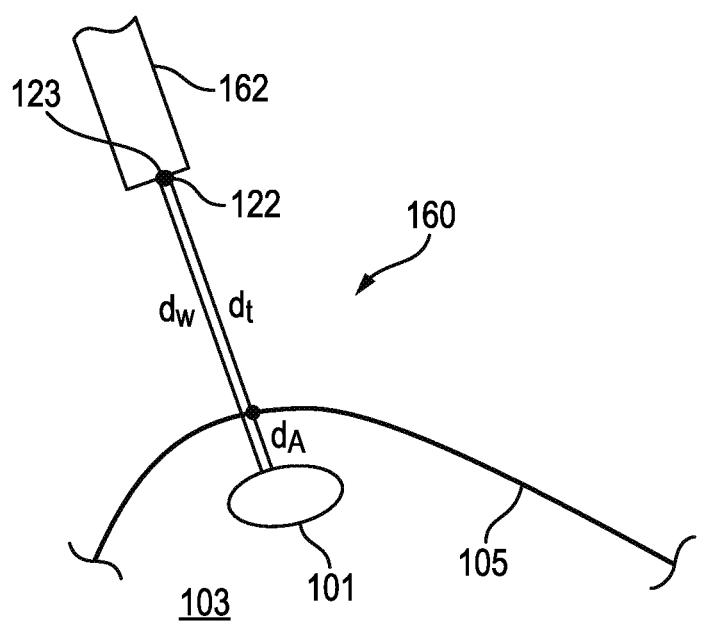
FIG. 3 is a schematic view of another embodiment of a surgical visualization system.

In another embodiment of a surgical visualization system 160 illustrated in FIG. 3, a surgical device 162, and not the imaging device 120, includes the optical waveform emitter 123 and the waveform sensor 122 that is configured to detect the reflected waveforms. The optical waveform emitter 123 is configured to emit waveforms for determining the distances $d_t$ and $d_w$ from a common device, such as the surgical device 162, as described herein. In such instances, the distance $d_A$ from the surface 105 of the tissue 103 to the surface of the critical structure 101 can be determined as follows:

$$d_A = d_w - d_t$$

Figure 4:
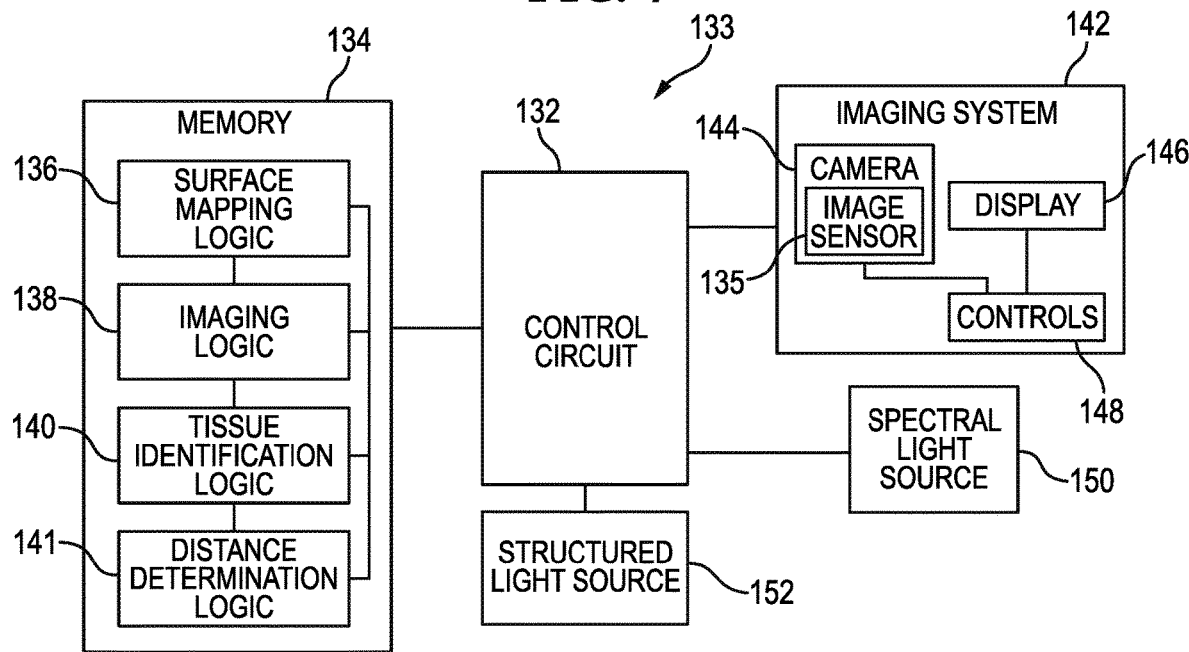
FIG. 4 is a schematic view of one embodiment of a control system for a surgical visualization system.

The surgical visualization system 100 includes a control system configured to control various aspects of the surgical visualization system 100. FIG. 4 illustrates one embodiment of a control system 133 that can be utilized as the control system of the surgical visualization system 100 (or other surgical visualization system described herein). The control system 133 includes a control circuit 132 configured to be in signal communication with a memory 134. The memory 134 is configured to store instructions executable by the control circuit 132, such as instructions to determine and/or recognize critical structures (e.g., the critical structure 101 of FIG. 1), instructions to determine and/or compute one or more distances and/or three-dimensional digital representations, and instructions to communicate information to a medical practitioner. As in this illustrated embodiment, the memory 134 can store surface mapping logic 136, imaging logic 138, tissue identification logic 140, and distance determining logic 141, although the memory 134 can store any combinations of the logics 136, 138, 140, 141 and/or can combine various logics together. The control system 133 also includes an imaging system 142 including a camera 144 (e.g., the imaging system including the imaging device 120 of FIG. 1), a display 146 (e.g., a monitor, a computer tablet screen, etc.), and controls 148 of the camera 144 and the display 146. The camera 144 includes an image sensor 135 (e.g., the waveform sensor 122) configured to receive signals from various light sources emitting light at various visible and invisible spectra (e.g., visible light, spectral imagers, three-dimensional lens, etc.). The display 146 is configured to depict real, virtual, and/or virtually-augmented images and/or information to a medical practitioner.

In an exemplary embodiment, the image sensor 135 is a solid-state electronic device containing up to millions of discrete photodetector sites called pixels. The image sensor 135 technology falls into one of two categories: Charge-Coupled Device (CCD) and Complementary Metal Oxide Semiconductor (CMOS) imagers and more recently, short-wave infrared (SWIR) is an emerging technology in imaging. Another type of the image sensor 135 employs a hybrid CCD/CMOS architecture (sold under the name "sCMOS") and consists of CMOS readout integrated circuits (ROICs) that are bump bonded to a CCD imaging substrate. CCD and CMOS image sensors 135 are sensitive to wavelengths in a range of about 350 nm to about 1050 nm, such as in a range of about 400 nm to about 1000 nm. A person skilled in the art will appreciate that a value may not be precisely at a value but nevertheless considered to be about that value for any of a variety of reasons, such as sensitivity of measurement equipment and manufacturing tolerances. CMOS sensors are, in general, more sensitive to IR wavelengths than CCD sensors. Solid state image sensors 135 are based on the photoelectric effect and, as a result, cannot distinguish between colors. Accordingly, there are two types of color CCD cameras: single chip and three-chip. Single chip color CCD cameras offer a common, low-cost imaging solution and use a mosaic (e.g., Bayer) optical filter to separate incoming light into a series of colors and employ an interpolation algorithm to resolve full color images. Each color is, then, directed to a different set of pixels. Three-chip color CCD cameras provide higher resolution by employing a prism to direct each section of the incident spectrum to a different chip. More accurate color reproduction is possible, as each point in space of the object has separate RGB intensity values, rather than using an algorithm to determine the color. Three-chip cameras offer extremely high resolutions.

The control system 133 also includes an emitter (e.g., the emitter 106) including a spectral light source 150 and a structured light source 152 each operably coupled to the control circuit 133. A single source can be pulsed to emit wavelengths of light in the spectral light source 150 range and wavelengths of light in the structured light source 152 range. Alternatively, a single light source can be pulsed to provide light in the invisible spectrum (e.g., infrared spectral light) and wavelengths of light on the visible spectrum. The spectral light source 150 can be, for example, a hyperspectral light source, a multispectral light source, and/or a selective spectral light source. The tissue identification logic 140 is configured to identify critical structure(s) (e.g., the critical structure 101 of FIG. 1) via data from the spectral light source 150 received by the image sensor 135 of the camera 144. The surface mapping logic 136 is configured to determine the surface contours of the visible tissue (e.g., the tissue 103) based on reflected structured light. With time-of-flight measurements, the distance determining logic 141 is configured to determine one or more distance(s) to the visible tissue and/or the critical structure. Output from each of the surface mapping logic 136, the tissue identification logic 140, and the distance determining logic 141 is configured to be provided to the imaging logic 138, and combined, blended, and/or overlaid by the imaging logic 138 to be conveyed to a medical practitioner via the display 146 of the imaging system 142.

Figure 5:
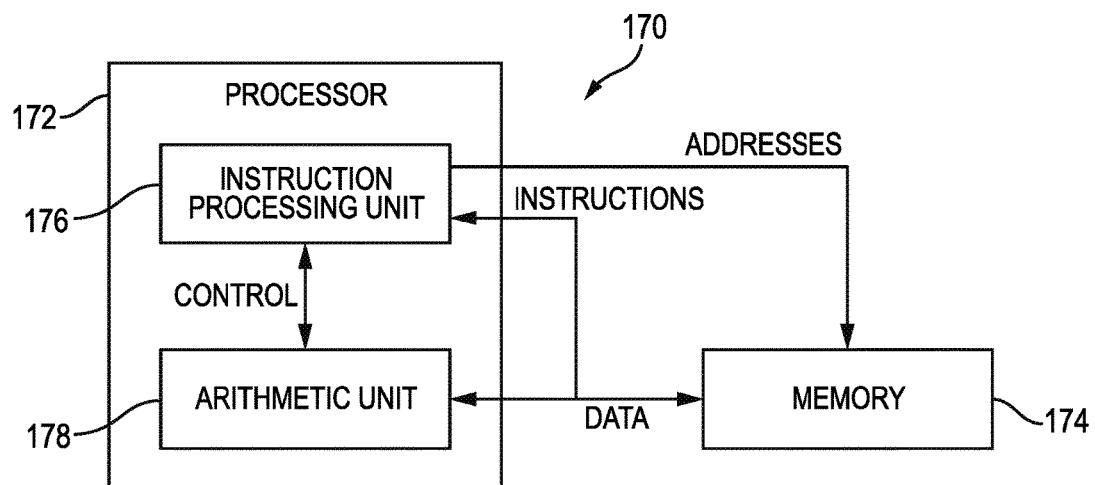
FIG. 5 is a schematic view of one embodiment of a control circuit of a control system for a surgical visualization system.

The control circuit 132 can have a variety of configurations. FIG. 5 illustrates one embodiment of a control circuit 170 that can be used as the control circuit 132 configured to control aspects of the surgical visualization system 100. The control circuit 170 is configured to implement various processes described herein. The control circuit 170 includes a microcontroller that includes a processor 172 (e.g., a microprocessor or microcontroller) operably coupled to a memory 174. The memory 174 is configured to store machine-executable instructions that, when executed by the processor 172, cause the processor 172 to execute machine instructions to implement various processes described herein. The processor 172 can be any one of a number of single-core or multicore processors known in the art. The memory 174 can include volatile and non-volatile storage media. The processor 172 includes an instruction processing unit 176 and an arithmetic unit 178. The instruction processing unit 176 is configured to receive instructions from the memory 174.

Figure 6:
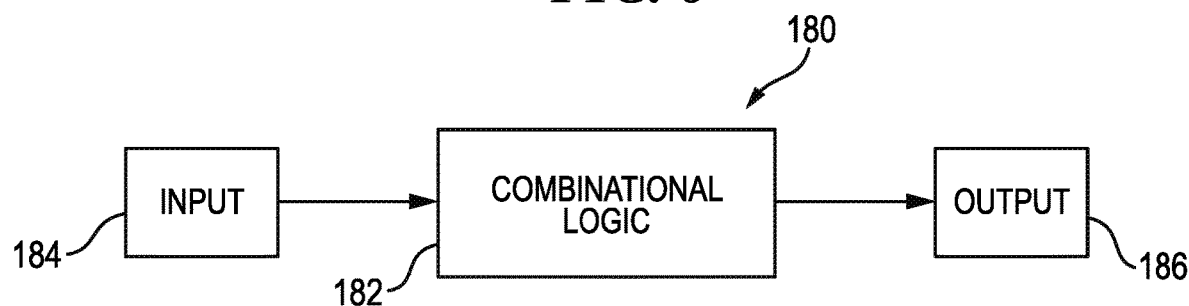
FIG. 6 is a schematic view of one embodiment of a combinational logic circuit of a surgical visualization system.

The surface mapping logic 136, the imaging logic 138, the tissue identification logic 140, and the distance determining logic 141 can have a variety of configurations. FIG. 6 illustrates one embodiment of a combinational logic circuit 180 configured to control aspects of the surgical visualization system 100 using logic such as one or more of the surface mapping logic 136, the imaging logic 138, the tissue identification logic 140, and the distance determining logic 141. The combinational logic circuit 180 includes a finite state machine that includes a combinational logic 182 configured to receive data associated with a surgical device (e.g. the surgical device 102 and/or the imaging device 120) at an input 184, process the data by the combinational logic 182, and provide an output 186 to a control circuit (e.g., the control circuit 132).

Figure 7:
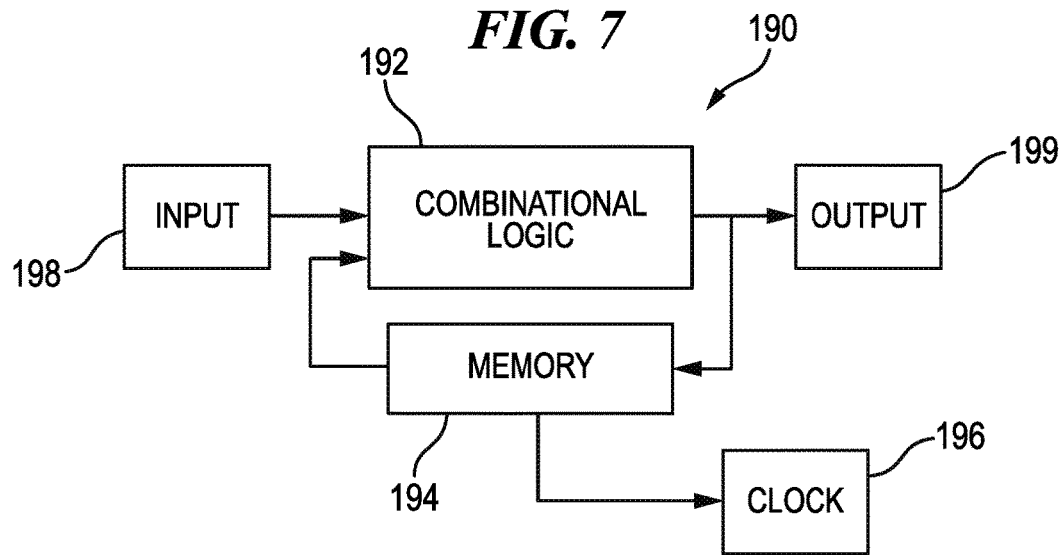
FIG. 7 is a schematic view of one embodiment of a sequential logic circuit of a surgical visualization system.

FIG. 7 illustrates one embodiment of a sequential logic circuit 190 configured to control aspects of the surgical visualization system 100 using logic such as one or more of the surface mapping logic 136, the imaging logic 138, the tissue identification logic 140, and the distance determining logic 141. The sequential logic circuit 190 includes a finite state machine that includes a combinational logic 192, a memory 194, and a clock 196. The memory 194 is configured to store a current state of the finite state machine. The sequential logic circuit 190 can be synchronous or asynchronous. The combinational logic 192 is configured to receive data associated with a surgical device (e.g. the surgical device 102 and/or the imaging device 120) at an input 198, process the data by the combinational logic 192, and provide an output 199 to a control circuit (e.g., the control circuit 132). In some embodiments, the sequential logic circuit 190 can include a combination of a processor (e.g., processor 172 of FIG. 5) and a finite state machine to implement various processes herein. In some embodiments, the finite state machine can include a combination of a combinational logic circuit (e.g., the combinational logic circuit 192 of FIG. 7) and the sequential logic circuit 190.

Figure 8:
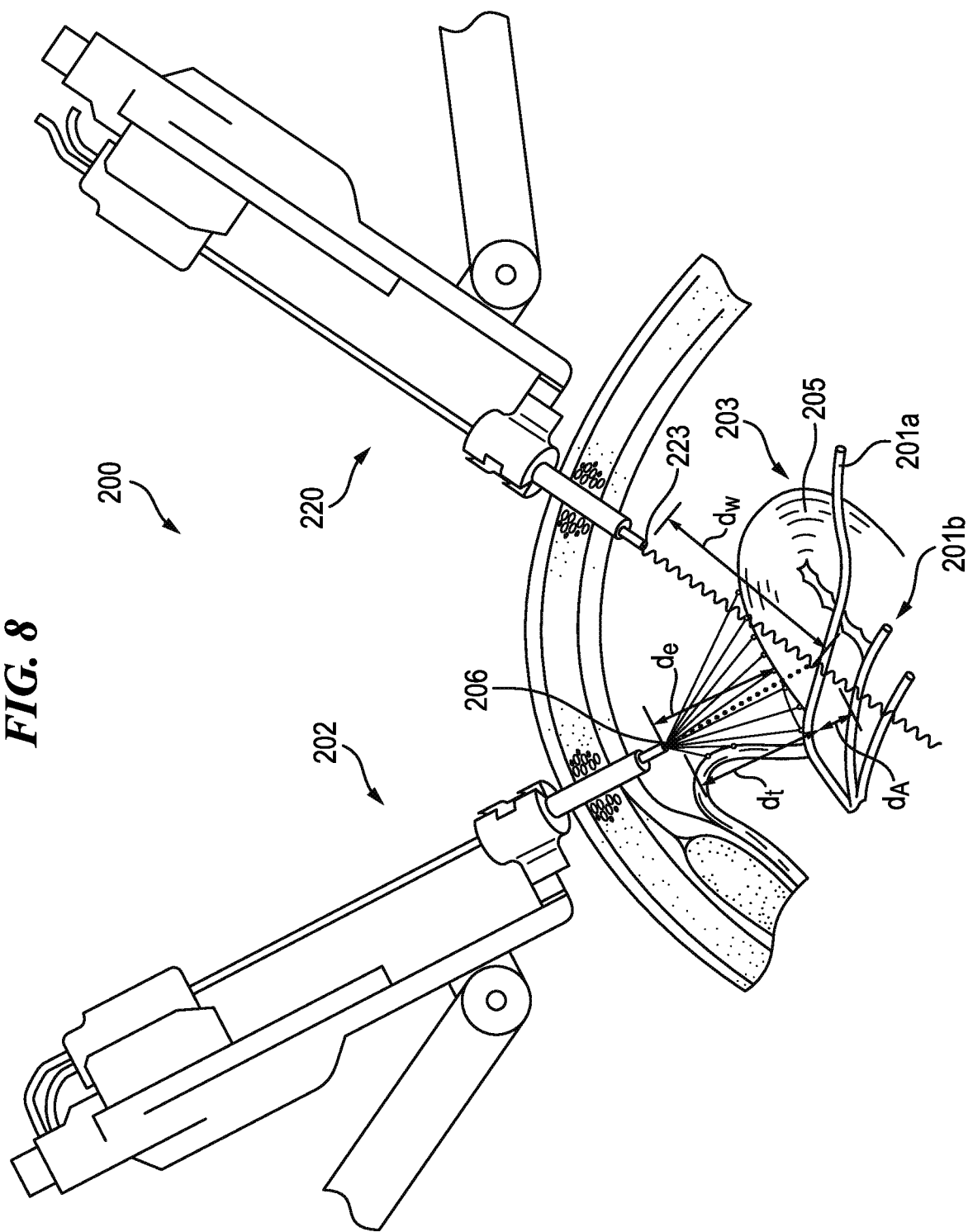
FIG. 8 is a schematic view of yet another embodiment of a surgical visualization system.

FIG. 8 illustrates another embodiment of a surgical visualization system 200. The surgical visualization system 200 is generally configured and used similar to the surgical visualization system 100 of FIG. 1, e.g., includes a surgical device 202 and an imaging device 220. The imaging device 220 includes a spectral light emitter 223 configured to emit spectral light in a plurality of wavelengths to obtain a spectral image of hidden structures, for example. The imaging device 220 can also include a three-dimensional camera and associated electronic processing circuits. The surgical visualization system 200 is shown being utilized intraoperatively to identify and facilitate avoidance of certain critical structures, such as a ureter 201a and vessels 201b, in an organ 203 (a uterus in this embodiment) that are not visible on a surface 205 of the organ 203.

The surgical visualization system 200 is configured to determine an emitter-to-tissue distance $d_e$ from an emitter 206 on the surgical device 202 to the surface 205 of the uterus 203 via structured light. The surgical visualization system 200 is configured to extrapolate a device-to-tissue distance $d_t$ from the surgical device 202 to the surface 205 of the uterus 203 based on the emitter-to-tissue distance $d_e$. The surgical visualization system 200 is also configured to determine a tissue-to-ureter distance $d_A$ from the ureter 201a to the surface 205 and a camera-to-ureter distance $d_w$ from the imaging device 220 to the ureter 201a. As described herein, e.g., with respect to the surgical visualization system 100 of FIG. 1, the surgical visualization system 200 is configured to determine the distance $d_w$ with spectral imaging and time-of-flight sensors, for example. In various embodiments, the surgical visualization system 200 can determine (e.g. triangulate) the tissue-to-ureter distance $d_A$ (or depth) based on other distances and/or the surface mapping logic described herein.

Figure 9:
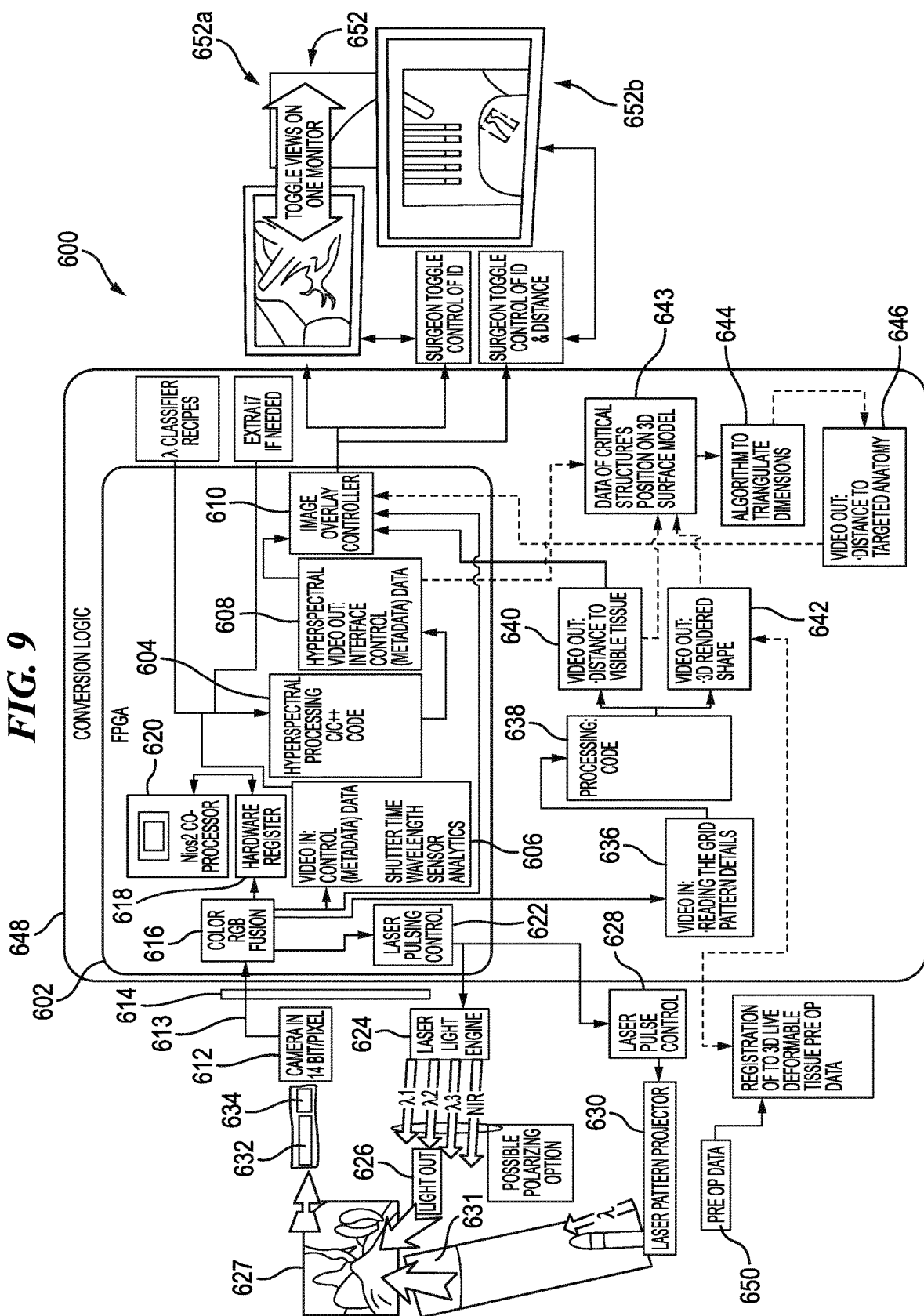
FIG. 9 is a schematic view of another embodiment of a control system for a surgical visualization system.

As mentioned above, a surgical visualization system includes a control system configured to control various aspects of the surgical visualization system. The control system can have a variety of configurations. FIG. 9 illustrates one embodiment of a control system 600 for a surgical visualization system, such as the surgical visualization system 100 of FIG. 1, the surgical visualization system 200 of FIG. 8, or other surgical visualization system described herein. The control system 600 is a conversion system that integrates spectral signature tissue identification and structured light tissue positioning to identify a critical structure, especially when those structure(s) are obscured by tissue, e.g., by fat, connective tissue, blood tissue, and/or organ(s), and/or by blood, and/or to detect tissue variability, such as differentiating tumors and/or non-healthy tissue from healthy tissue within an organ.

The control system 600 is configured for implementing a hyperspectral imaging and visualization system in which a molecular response is utilized to detect and identify anatomy in a surgical field of view. The control system 600 includes a conversion logic circuit 648 configured to convert tissue data to usable information for surgeons and/or other medical practitioners. For example, variable reflectance based on wavelengths with respect to obscuring material can be utilized to identify the critical structure in the anatomy. Moreover, the control system 600 is configured to combine the identified spectral signature and the structural light data in an image. For example, the control system 600 can be employed to create of three-dimensional data set for surgical use in a system with augmentation image overlays. Techniques can be employed both intraoperatively and preoperatively using additional visual information. In various embodiments, the control system 600 is configured to provide warnings to a medical practitioner when in the proximity of one or more critical structures. Various algorithms can be employed to guide robotic automation and semi-automated approaches based on the surgical procedure and proximity to the critical structure(s).

A projected array of lights is employed by the control system 600 to determine tissue shape and motion intraoperatively. Alternatively, flash Lidar may be utilized for surface mapping of the tissue.

The control system 600 is configured to detect the critical structure, which as mentioned above can include one or more critical structures, and provide an image overlay of the critical structure and measure the distance to the surface of the visible tissue and the distance to the embedded/buried critical structure(s). The control system 600 can measure the distance to the surface of the visible tissue or detect the critical structure and provide an image overlay of the critical structure.

The control system 600 includes a spectral control circuit 602. The spectral control circuit 602 can be a field programmable gate array (FPGA) or another suitable circuit configuration, such as the configurations described with respect to FIG. 6, FIG. 7, and FIG. 8. The spectral control circuit 602 includes a processor 604 configured to receive video input signals from a video input processor 606. The processor 604 can be configured for hyperspectral processing and can utilize C/C++ code, for example. The video input processor 606 is configured to receive video-in of control (metadata) data such as shutter time, wave length, and sensor analytics, for example. The processor 604 is configured to process the video input signal from the video input processor 606 and provide a video output signal to a video output processor 608, which includes a hyperspectral video-out of interface control (metadata) data, for example. The video output processor 608 is configured to provides the video output signal to an image overlay controller 610.

The video input processor 606 is operatively coupled to a camera 612 at the patient side via a patient isolation circuit 614. The camera 612 includes a solid state image sensor 634. The patient isolation circuit 614 can include a plurality of transformers so that the patient is isolated from other circuits in the system. The camera 612 is configured to receive intraoperative images through optics 632 and the image sensor 634. The image sensor 634 can include a CMOS image sensor, for example, or can include another image sensor technology, such as those discussed herein in connection with FIG. 4. The camera 612 is configured to output 613 images in 14 bit/pixel signals. A person skilled in the art will appreciate that higher or lower pixel resolutions can be employed. The isolated camera output signal 613 is provided to a color RGB fusion circuit 616, which in this illustrated embodiment employs a hardware register 618 and a Nios2 co-processor 620 configured to process the camera output signal 613. A color RGB fusion output signal is provided to the video input processor 606 and a laser pulsing control circuit 622.

The laser pulsing control circuit 622 is configured to control a laser light engine 624. The laser light engine 624 is configured to output light in a plurality of wavelengths ($\lambda 1, \lambda 2, \lambda 3 \ldots \lambda n$) including near infrared (NIR). The laser light engine 624 can operate in a plurality of modes. For example, the laser light engine 624 can operate in two modes. In a first mode, e.g., a normal operating mode, the laser light engine 624 is configured to output an illuminating signal. In a second mode, e.g., an identification mode, the laser light engine 624 is configured to output RGBG and NIR light. In various embodiments, the laser light engine 624 can operate in a polarizing mode.

Light output 626 from the laser light engine 624 is configured to illuminate targeted anatomy in an intraoperative surgical site 627. The laser pulsing control circuit 622 is also configured to control a laser pulse controller 628 for a laser pattern projector 630 configured to project a laser light pattern 631, such as a grid or pattern of lines and/or dots, at a predetermined wavelength ($\lambda 2$) on an operative tissue or organ at the surgical site 627. The camera 612 is configured to receive the patterned light as well as the reflected light output through the camera optics 632. The image sensor 634 is configured to convert the received light into a digital signal.

The color RGB fusion circuit 616 is also configured to output signals to the image overlay controller 610 and a video input module 636 for reading the laser light pattern 631 projected onto the targeted anatomy at the surgical site 627 by the laser pattern projector 630. A processing module 638 is configured to process the laser light pattern 631 and output a first video output signal 640 representative of the distance to the visible tissue at the surgical site 627. The data is provided to the image overlay controller 610. The processing module 638 is also configured to output a second video signal 642 representative of a three-dimensional rendered shape of the tissue or organ of the targeted anatomy at the surgical site.

The first and second video output signals 640, 642 include data representative of the position of the critical structure on a three-dimensional surface model, which is provided to an integration module 643. In combination with data from the video out processor 608 of the spectral control circuit 602, the integration module 643 is configured to determine the distance (e.g., distance $d_A$ of FIG. 1) to a buried critical structure (e.g., via triangularization algorithms 644), and the distance to the buried critical structure can be provided to the image overlay controller 610 via a video out processor 646. The foregoing conversion logic can encompass the conversion logic circuit 648 intermediate video monitors 652 and the camera 624/laser pattern projector 630 positioned at the surgical site 627.

Preoperative data 650, such as from a CT or MRI scan, can be employed to register or align certain three-dimensional deformable tissue in various instances. Such preoperative data 650 can be provided to the integration module 643 and ultimately to the image overlay controller 610 so that such information can be overlaid with the views from the camera 612 and provided to the video monitors 652. Embodiments of registration of preoperative data are further described in U.S. Pat. Pub. No. 2020/0015907 entitled "Integration Of Imaging Data" filed Sep. 11, 2018, which is hereby incorporated by reference herein in its entirety.

The video monitors 652 are configured to output the integrated/augmented views from the image overlay controller 610. A medical practitioner can select and/or toggle between different views on one or more displays. On a first display 652a, which is a monitor in this illustrated embodiment, the medical practitioner can toggle between (A) a view in which a three-dimensional rendering of the visible tissue is depicted and (B) an augmented view in which one or more hidden critical structures are depicted over the three-dimensional rendering of the visible tissue. On a second display 652b, which is a monitor in this illustrated embodiment, the medical practitioner can toggle on distance measurements to one or more hidden critical structures and/or the surface of visible tissue, for example.

The various surgical visualization systems described herein can be utilized to visualize various different types of tissues and/or anatomical structures, including tissues and/or anatomical structures that may be obscured from being visualized by EMR in the visible portion of the spectrum. The surgical visualization system can utilize a spectral imaging system, as mentioned above, which can be configured to visualize different types of tissues based upon their varying combinations of constituent materials. In particular, a spectral imaging system can be configured to detect the presence of various constituent materials within a tissue being visualized based on the absorption coefficient of the tissue across various EMR wavelengths. The spectral imaging system can be configured to characterize the tissue type of the tissue being visualized based upon the particular combination of constituent materials.

Figure 10:
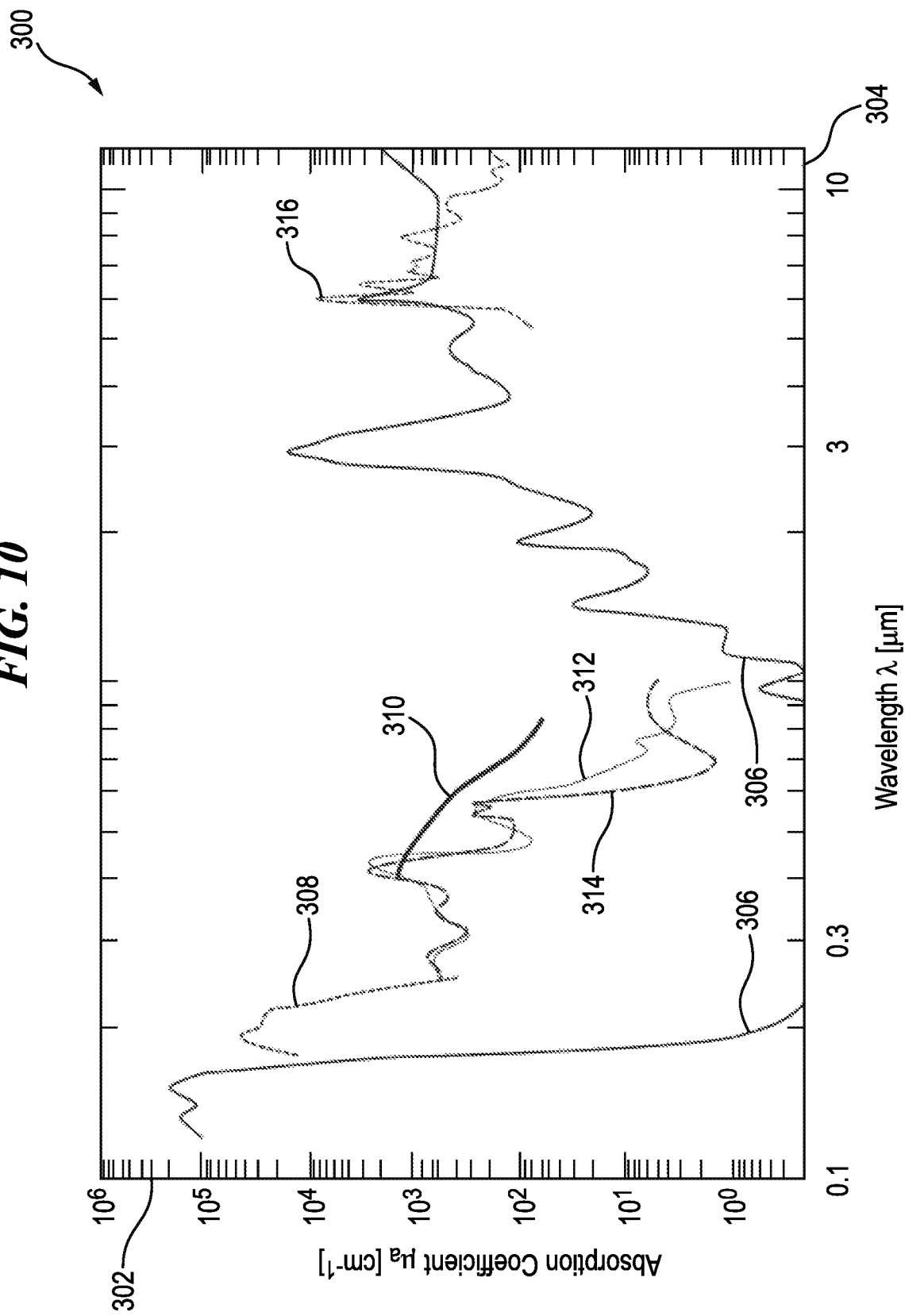
FIG. 10 is a graph showing wavelength versus absorption coefficient for various biological materials.

FIG. 10 shows a graph 300 depicting how the absorption coefficient of various biological materials varies across the EMR wavelength spectrum. In the graph 300, the vertical axis 302 represents absorption coefficient of the biological material in $cm^{-1}$, and the horizontal axis 304 represents EMR wavelength in μm. A first line 306 in the graph 300 represents the absorption coefficient of water at various EMR wavelengths, a second line 308 represents the absorption coefficient of protein at various EMR wavelengths, a third line 310 represents the absorption coefficient of melanin at various EMR wavelengths, a fourth line 312 represents the absorption coefficient of deoxygenated hemoglobin at various EMR wavelengths, a fifth line 314 represents the absorption coefficient of oxygenated hemoglobin at various EMR wavelengths, and a sixth line 316 represents the absorption coefficient of collagen at various EMR wavelengths. Different tissue types have different combinations of constituent materials and, therefore, the tissue type(s) being visualized by a surgical visualization system can be identified and differentiated between according to the particular combination of detected constituent materials. Accordingly, a spectral imaging system of a surgical visualization system can be configured to emit EMR at a number of different wavelengths, determine the constituent materials of the tissue based on the detected absorption EMR absorption response at the different wavelengths, and then characterize the tissue type based on the particular detected combination of constituent materials.

Figure 11:
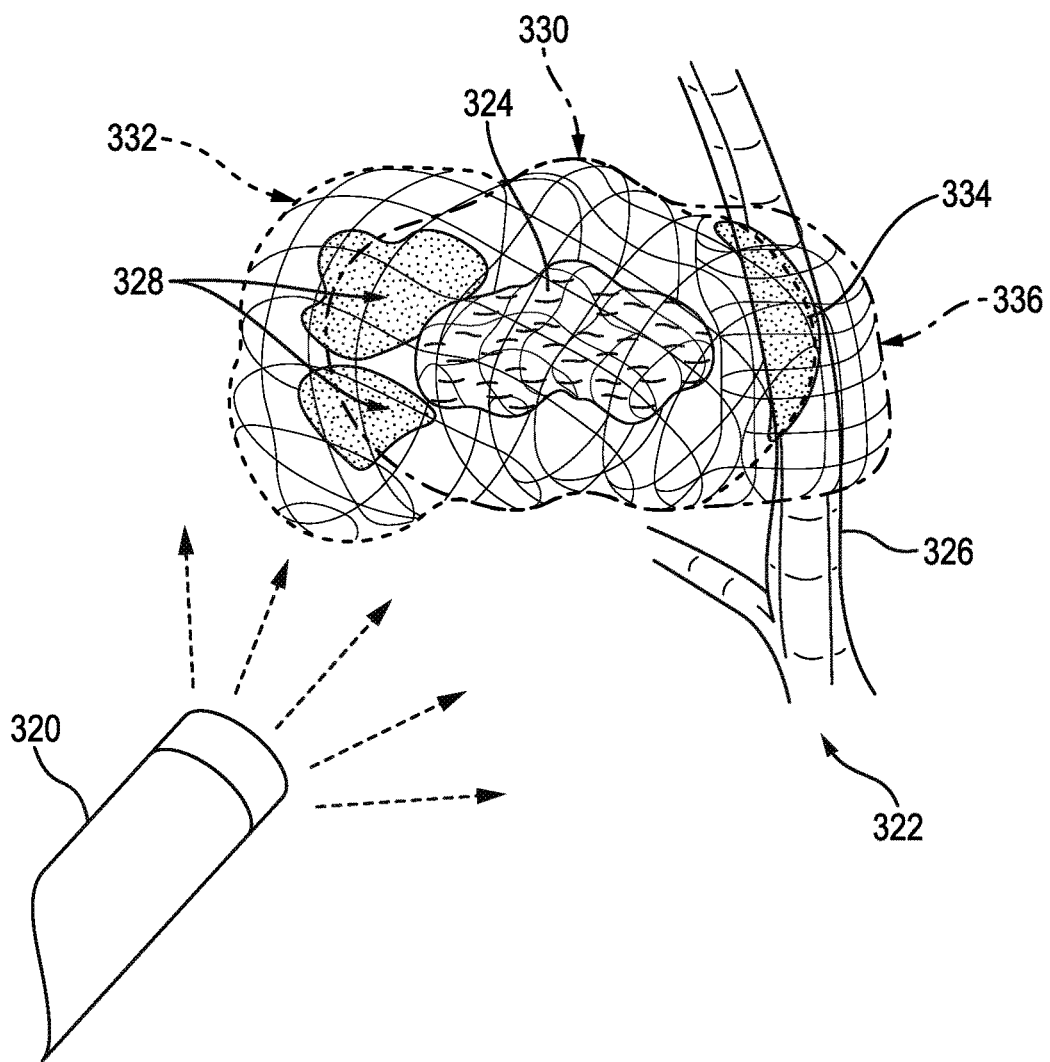
FIG. 11 is a schematic view of one embodiment of a spectral emitter visualizing a surgical site.

FIG. 11 shows an embodiment of the utilization of spectral imaging techniques to visualize different tissue types and/or anatomical structures. In FIG. 11, a spectral emitter 320 (e.g., the spectral light source 150 of FIG. 4) is being utilized by an imaging system to visualize a surgical site 322. The EMR emitted by the spectral emitter 320 and reflected from the tissues and/or structures at the surgical site 322 is received by an image sensor (e.g., the image sensor 135 of FIG. 4) to visualize the tissues and/or structures, which can be either visible (e.g., be located at a surface of the surgical site 322) or obscured (e.g., underlay other tissue and/or structures at the surgical site 322). In this embodiment, an imaging system (e.g., the imaging system 142 of FIG. 4) visualizes a tumor 324, an artery 326, and various abnormalities 328 (e.g., tissues not confirming to known or expected spectral signatures) based upon the spectral signatures characterized by the differing absorptive characteristics (e.g., absorption coefficient) of the constituent materials for each of the different tissue/structure types. The visualized tissues and structures can be displayed on a display screen associated with or coupled to the imaging system (e.g., the display 146 of the imaging system 142 of FIG. 4), on a primary display (e.g., the primary display 819 of FIG. 19), on a non-sterile display (e.g., the non-sterile displays 807, 809 of FIG. 19), on a display of a surgical hub (e.g., the display of the surgical hub 806 of FIG. 19), on a device/instrument display, and/or on another display.

The imaging system can be configured to tailor or update the displayed surgical site visualization according to the identified tissue and/or structure types. For example, as shown in FIG. 11, the imaging system can display a margin 330 associated with the tumor 324 being visualized on a display screen associated with or coupled to the imaging system, on a primary display, on a non-sterile display, on a display of a surgical hub, on a device/instrument display, and/or on another display. The margin 330 can indicate the area or amount of tissue that should be excised to ensure complete removal of the tumor 324. The surgical visualization system's control system (e.g., the control system 133 of FIG. 4) can be configured to control or update the dimensions of the margin 330 based on the tissues and/or structures identified by the imaging system. In this illustrated embodiment, the imaging system has identified multiple abnormalities 328 within the field of view (FOV). Accordingly, the control system can adjust the displayed margin 330 to a first updated margin 332 having sufficient dimensions to encompass the abnormalities 328. Further, the imaging system has also identified the artery 326 partially overlapping with the initially displayed margin 330 (as indicated by a highlighted region 334 of the artery 326). Accordingly, the control system can adjust the displayed margin to a second updated margin 336 having sufficient dimensions to encompass the relevant portion of the artery 326.

Figure 12:
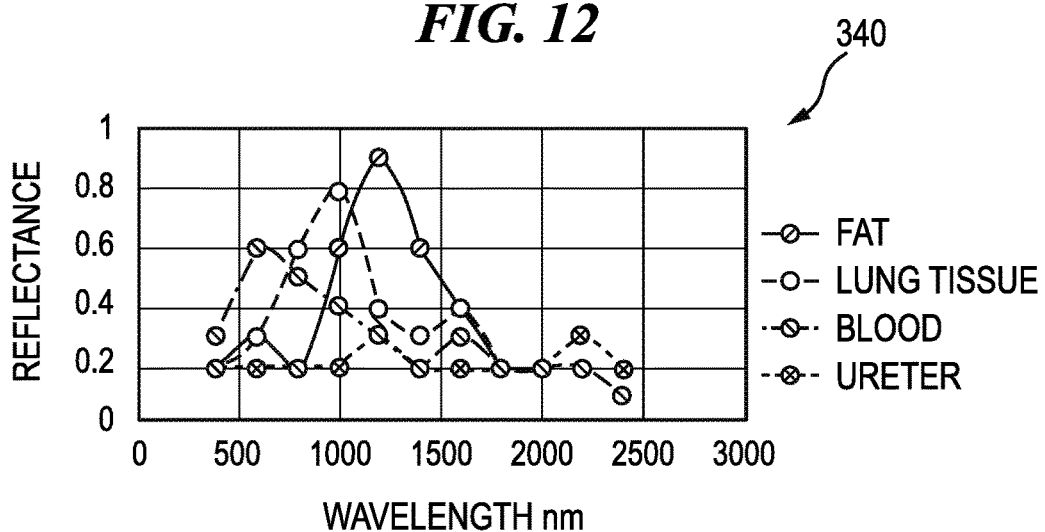
FIG. 12 is a graph depicting illustrative hyperspectral identifying signatures to differentiate a ureter from obscurants.
Figure 13:
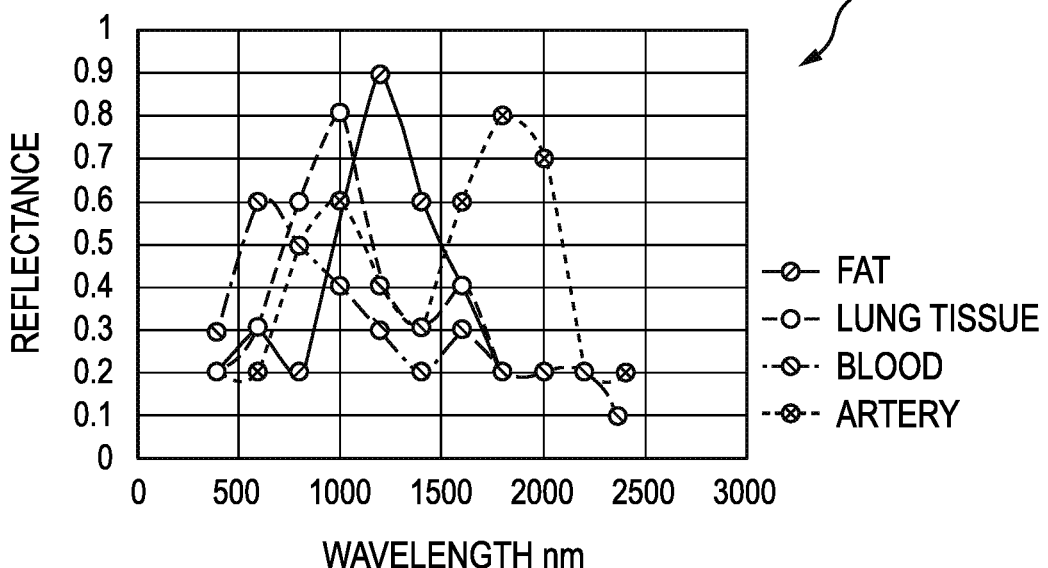
FIG. 13 is a graph depicting illustrative hyperspectral identifying signatures to differentiate an artery from obscurants.
Figure 14:
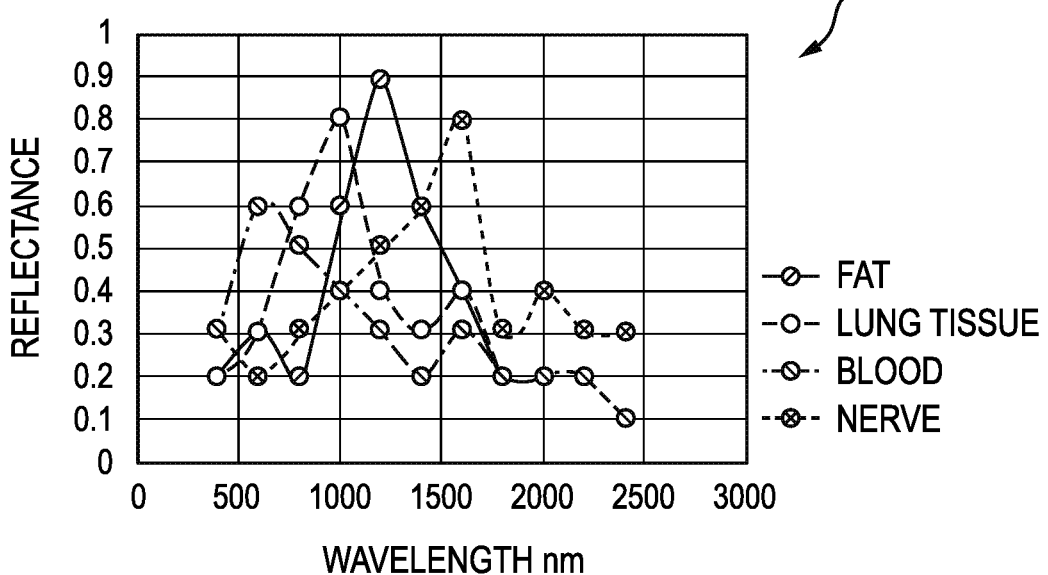
FIG. 14 is a graph depicting illustrative hyperspectral identifying signatures to differentiate a nerve from obscurants.

Tissues and/or structures can also be imaged or characterized according to their reflective characteristics, in addition to or in lieu of their absorptive characteristics described above with respect to FIG. 10 and FIG. 11, across the EMR wavelength spectrum. For example, FIG. 12, FIG. 13, and FIG. 14 illustrate various graphs of reflectance of different types of tissues or structures across different EMR wavelengths. FIG. 12 is a graphical representation 340 of an illustrative ureter signature versus obscurants. FIG. 13 is a graphical representation 342 of an illustrative artery signature versus obscurants. FIG. 14 is a graphical representation 344 of an illustrative nerve signature versus obscurants. The plots in FIG. 12, FIG. 13, and FIG. 14 represent reflectance as a function of wavelength (nm) for the particular structures (ureter, artery, and nerve) relative to the corresponding reflectances of fat, lung tissue, and blood at the corresponding wavelengths. These graphs are simply for illustrative purposes and it should be understood that other tissues and/or structures could have corresponding detectable reflectance signatures that would allow the tissues and/or structures to be identified and visualized.

Select wavelengths for spectral imaging can be identified and utilized based on the anticipated critical structures and/or obscurants at a surgical site (e.g., "selective spectral" imaging). By utilizing selective spectral imaging, the amount of time required to obtain the spectral image can be minimized such that the information can be obtained in real-time and utilized intraoperatively. The wavelengths can be selected by a medical practitioner or by a control circuit based on input by a user, e.g., a medical practitioner. In certain instances, the wavelengths can be selected based on machine learning and/or big data accessible to the control circuit via, e.g., a cloud or surgical hub.

Figure 15:
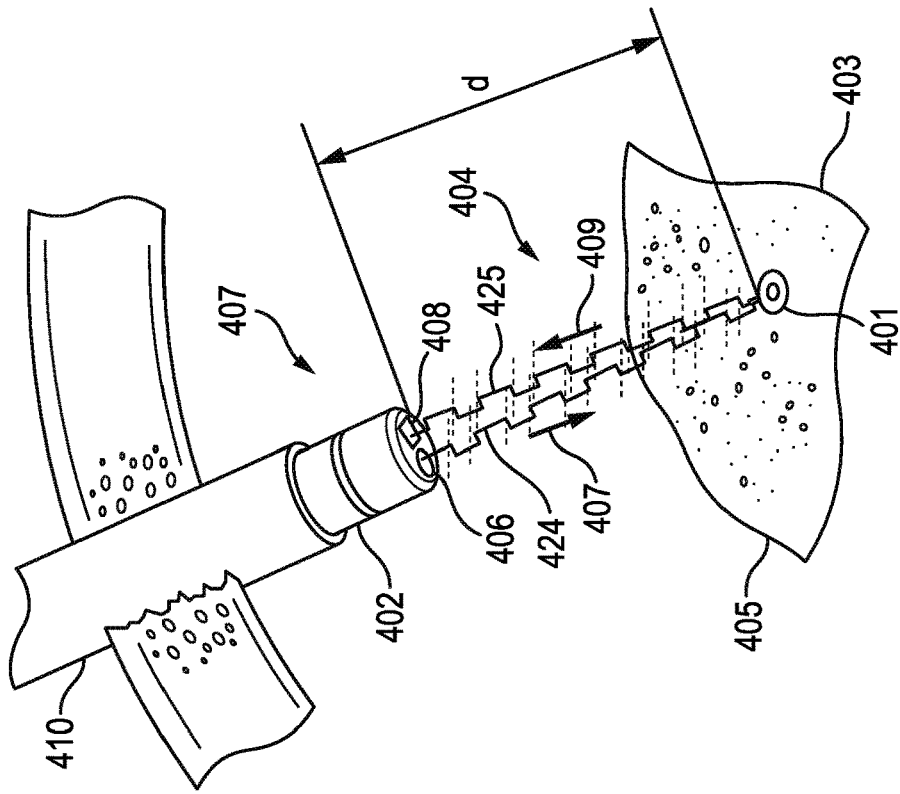
FIG. 15 is a schematic view of one embodiment of a near infrared (NIR) time-of-flight measurement system being utilized intraoperatively.

FIG. 15 illustrates one embodiment of spectral imaging to tissue being utilized intraoperatively to measure a distance between a waveform emitter and a critical structure that is obscured by tissue. FIG. 15 shows an embodiment of a time-of-flight sensor system 404 utilizing waveforms 424, 425. The time-of-flight sensor system 404 can be incorporated into a surgical visualization system, e.g., as the sensor system 104 of the surgical visualization system 100 of FIG. 1. The time-of-flight sensor system 404 includes a waveform emitter 406 and a waveform receiver 408 on the same surgical device 402 (e.g., the emitter 106 and the receiver 108 on the same surgical device 102 of FIG. 1). The emitted wave 400 extends to a critical structure 401 (e.g., the critical structure 101 of FIG. 1) from the emitter 406, and the received wave 425 is reflected back to by the receiver 408 from the critical structure 401. The surgical device 402 in this illustrated embodiment is positioned through a trocar 410 that extends into a cavity 407 in a patient. Although the trocar 410 is used in this in this illustrated embodiment, other trocars or other access devices can be used, or no access device may be used.

Figure 16:
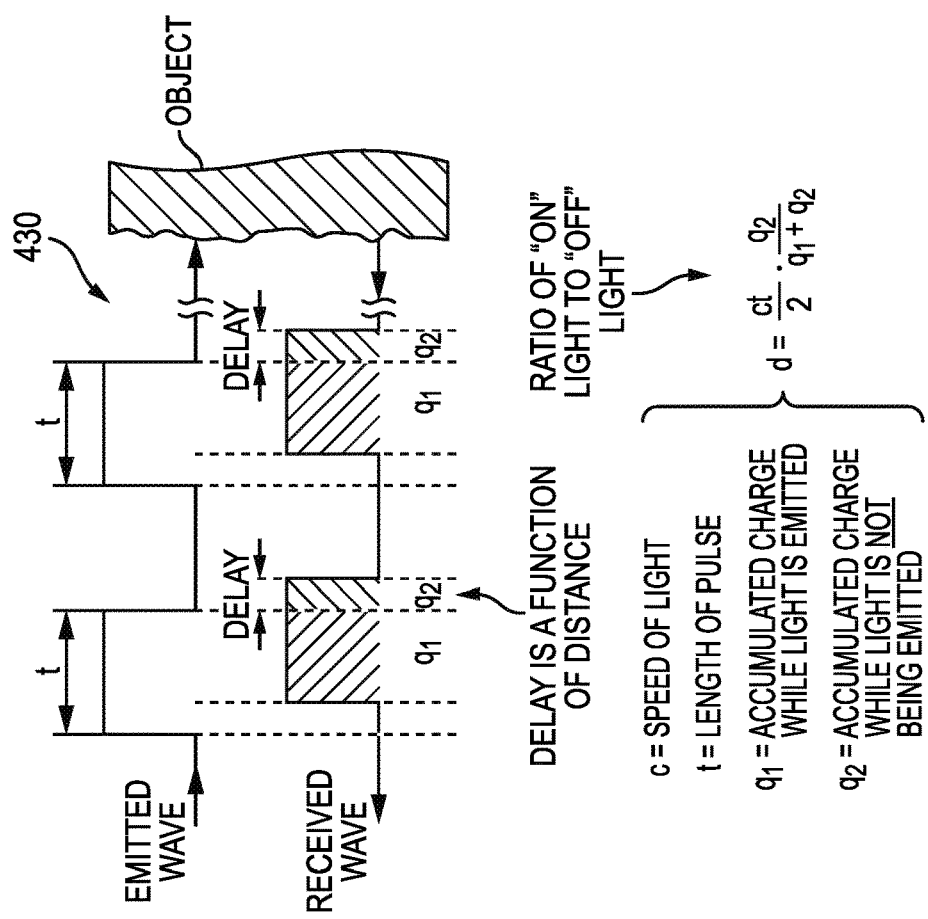
FIG. 16 shows a time-of-flight timing diagram for the system of FIG. 15.

The waveforms 424, 425 are configured to penetrate obscuring tissue 403, such as by having wavelengths in the NIR or SWIR spectrum of wavelengths. A spectral signal (e.g., hyperspectral, multispectral, or selective spectral) or a photoacoustic signal is emitted from the emitter 406, as shown by a first arrow 407 pointing distally, and can penetrate the tissue 403 in which the critical structure 401 is concealed. The emitted waveform 424 is reflected by the critical structure 401, as shown by a second arrow 409 pointing proximally. The received waveform 425 can be delayed due to a distance d between a distal end of the surgical device 402 and the critical structure 401. The waveforms 424, 425 can be selected to target the critical structure 401 within the tissue 403 based on the spectral signature of the critical structure 401, as described herein. The emitter 406 is configured to provide a binary signal on and off, as shown in FIG. 16, for example, which can be measured by the receiver 408.

Based on the delay between the emitted wave 424 and the received wave 425, the time-of-flight sensor system 404 is configured to determine the distance d. A time-of-flight timing diagram 430 for the emitter 406 and the receiver 408 of FIG. 15 is shown in FIG. 16. The delay is a function of the distance d and the distance d is given by:

$$d = \frac{ct}{2} \cdot \frac{q_2}{q_1 + q_2}$$

where c=the speed of light; t=length of pulse; q1=accumulated charge while light is emitted; and q2=accumulated charge while light is not being emitted.

The time-of-flight of the waveforms 424, 425 corresponds to the distance d in FIG. 15. In various instances, additional emitters/receivers and/or pulsing signals from the emitter 406 can be configured to emit a non-penetrating signal. The non-penetrating signal can be configured to determine the distance from the emitter 406 to the surface 405 of the obscuring tissue 403. In various instances, a depth of the critical structure 401 can be determined by:

$$d_A = d_w - d_t$$

where $d_A$=the depth of the critical structure 401; $d_w$=the distance from the emitter 406 to the critical structure 401 (d in FIG. 15); and $d_t$=the distance from the emitter 406 (on the distal end of the surgical device 402) to the surface 405 of the obscuring tissue 403.

Figure 17:
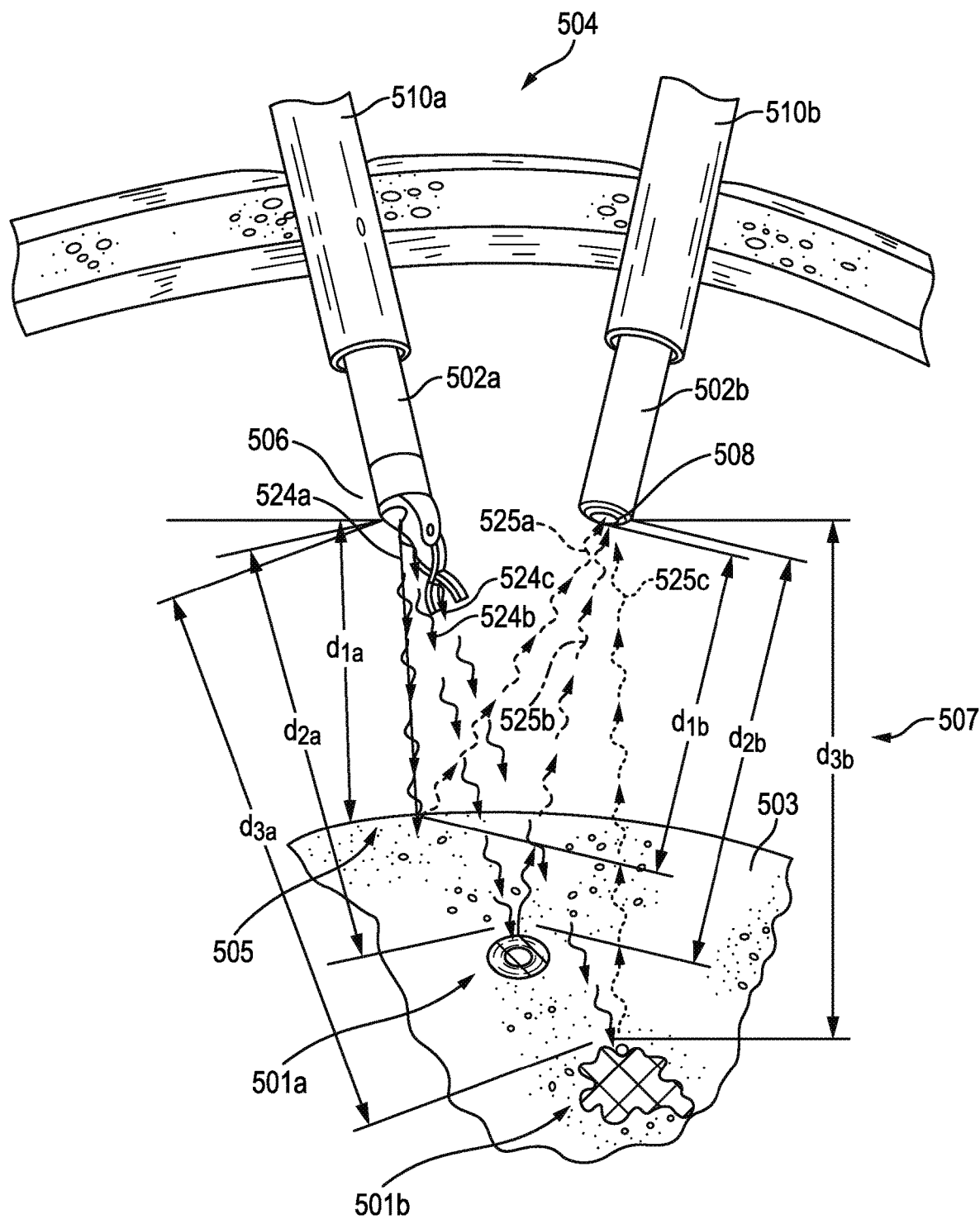
FIG. 17 is a schematic view of another embodiment of a near infrared (NIR) time-of-flight measurement system being utilized intraoperatively.

FIG. 17 illustrates another embodiment of a time-of-flight sensor system 504 utilizing waves 524a, 524b, 524c, 525a, 525b, 525c is shown. The time-of-flight sensor system 504 can be incorporated into a surgical visualization system, e.g., as the sensor system 104 of the surgical visualization system 100 of FIG. 1. The time-of-flight sensor system 504 includes a waveform emitter 506 and a waveform receiver 508 (e.g., the emitter 106 and the receiver 108 of FIG. 1). The waveform emitter 506 is positioned on a first surgical device 502a (e.g., the surgical device 102 of FIG. 1), and the waveform receiver 508 is positioned on a second surgical device 502b. The surgical devices 502a, 502b are positioned through first and second trocars 510a, 510b, respectively, which extend into a cavity 507 in a patient. Although the trocars 510a, 510b are used in this in this illustrated embodiment, other trocars or other access devices can be used, or no access device may be used. The emitted waves 524a, 524b, 524c extend toward a surgical site from the emitter 506, and the received waves 525a, 525b, 525c are reflected back to the receiver 508 from various structures and/or surfaces at the surgical site.

The different emitted waves 524a, 524b, 524c are configured to target different types of material at the surgical site. For example, the wave 524a targets obscuring tissue 503, the wave 524b targets a first critical structure 501a (e.g., the critical structure 101 of FIG. 1), which is a vessel in this illustrated embodiment, and the wave 524c targets a second critical structure 501b (e.g., the critical structure 101 of FIG. 1), which is a cancerous tumor in this illustrated embodiment. The wavelengths of the waves 524a, 524b, 524c can be in the visible light, NIR, or SWIR spectrum of wavelengths. For example, visible light can be reflected off a surface 505 of the tissue 503, and NIR and/or SWIR waveforms can penetrate the surface 505 of the tissue 503. In various aspects, as described herein, a spectral signal (e.g., hyperspectral, multispectral, or selective spectral) or a photoacoustic signal can be emitted from the emitter 506. The waves 524b, 524c can be selected to target the critical structures 501a, 501b within the tissue 503 based on the spectral signature of the critical structure 501a, 501b, as described herein. Photoacoustic imaging is further described in various U.S. patent applications, which are incorporated by reference herein in the present disclosure.

The emitted waves 524a, 524b, 524c are reflected off the targeted material, namely the surface 505, the first critical structure 501a, and the second structure 501b, respectively. The received waveforms 525a, 525b, 525c can be delayed due to distances $d_{1a}$, $d_{2a}$, $d_{3a}$, $d_{1b}$, $d_{2b}$, $d_{2c}$.

In the time-of-flight sensor system 504, in which the emitter 506 and the receiver 508 are independently positionable (e.g., on separate surgical devices 502a, 502b and/or controlled by separate robotic arms), the various distances $d_{1a}$, $d_{2a}$, $d_{3a}$, $d_{1b}$, $d_{2b}$, $d_{2c}$ can be calculated from the known position of the emitter 506 and the receiver 508. For example, the positions can be known when the surgical devices 502a, 502b are robotically-controlled. Knowledge of the positions of the emitter 506 and the receiver 508, as well as the time of the photon stream to target a certain tissue and the information received by the receiver 508 of that particular response can allow a determination of the distances $d_{1a}$, $d_{2a}$, $d_{3a}$, $d_{1b}$, $d_{2b}$, $d_{2c}$. In one aspect, the distance to the obscured critical structures 501a, 501b can be triangulated using penetrating wavelengths. Because the speed of light is constant for any wavelength of visible or invisible light, the time-of-flight sensor system 504 can determine the various distances.

In a view provided to the medical practitioner, such as on a display, the receiver 508 can be rotated such that a center of mass of the target structure in the resulting images remains constant, e.g., in a plane perpendicular to an axis of a select target structure 503, 501a, or 501b. Such an orientation can quickly communicate one or more relevant distances and/or perspectives with respect to the target structure. For example, as shown in FIG. 17, the surgical site is displayed from a viewpoint in which the critical structure 501a is perpendicular to the viewing plane (e.g., the vessel is oriented in/out of the page). Such an orientation can be default setting; however, the view can be rotated or otherwise adjusted by a medical practitioner. In certain instances, the medical practitioner can toggle between different surfaces and/or target structures that define the viewpoint of the surgical site provided by the imaging system.

As in this illustrated embodiment, the receiver 508 can be mounted on the trocar 510b (or other access device) through which the surgical device 502b is positioned. In other embodiments, the receiver 508 can be mounted on a separate robotic arm for which the three-dimensional position is known. In various instances, the receiver 508 can be mounted on a movable arm that is separate from a robotic surgical system that controls the surgical device 502a or can be mounted to an operating room (OR) table or fixture that is intraoperatively registerable to the robot coordinate plane. In such instances, the position of the emitter 506 and the receiver 508 can be registerable to the same coordinate plane such that the distances can be triangulated from outputs from the time-of-flight sensor system 504.

Combining time-of-flight sensor systems and near-infrared spectroscopy (NIRS), termed TOF-NIRS, which is capable of measuring the time-resolved profiles of NIR light with nanosecond resolution can be found in "Time-Of-Flight Near-Infrared Spectroscopy For Nondestructive Measurement Of Internal Quality In Grapefruit," Journal of the American Society for Horticultural Science, May 2013 vol. 138 no. 3 225-228, which is hereby incorporated by reference in its entirety.

Embodiments of visualization systems and aspects and uses thereof are described further in U.S. Pat. Pub. No. 2020/0015923 entitled "Surgical Visualization Platform" filed Sep. 11, 2018, U.S. Pat. Pub. No. 2020/0015900 entitled "Controlling An Emitter Assembly Pulse Sequence" filed Sep. 11, 2018, U.S. Pat. Pub. No. 2020/0015668 entitled "Singular EMR Source Emitter Assembly" filed Sep. 11, 2018, U.S. Pat. Pub. No. 2020/0015925 entitled "Combination Emitter And Camera Assembly" filed Sep. 11, 2018, U.S. Pat. Pub. No. 2020/00015899 entitled "Surgical Visualization With Proximity Tracking Features" filed Sep. 11, 2018, U.S. Pat. Pub. No. 2020/00015903 entitled "Surgical Visualization Of Multiple Targets" filed Sep. 11, 2018, U.S. Pat. No. 10,792,034 entitled "Visualization Of Surgical Devices" filed Sep. 11, 2018, U.S. Pat. Pub. No. 2020/0015897 entitled "Operative Communication Of Light" filed Sep. 11, 2018, U.S. Pat. Pub. No. 2020/0015924 entitled "Robotic Light Projection Tools" filed Sep. 11, 2018, U.S. Pat. Pub. No. 2020/0015898 entitled "Surgical Visualization Feedback System" filed Sep. 11, 2018, U.S. Pat. Pub. No. 2020/0015906 entitled "Surgical Visualization And Monitoring" filed Sep. 11, 2018, U.S. Pat. Pub. No. 2020/0015907 entitled "Integration Of Imaging Data" filed Sep. 11, 2018, U.S. Pat. No. 10,925,598 entitled "Robotically-Assisted Surgical Suturing Systems" filed Sep. 11, 2018, U.S. Pat. Pub. No. 2020/0015901 entitled "Safety Logic For Surgical Suturing Systems" filed Sep. 11, 2018, U.S. Pat. Pub. No. 2020/0015914 entitled "Robotic Systems With Separate Photoacoustic Receivers" filed Sep. 11, 2018, U.S. Pat. Pub. No. 2020/0015902 entitled "Force Sensor Through Structured Light Deflection" filed Sep. 11, 2018, U.S. Pat. Pub. No. 2019/0201136 entitled "Method Of Hub Communication" filed Dec. 4, 2018, U.S. patent application Ser. No. 16/729,772 entitled "Analyzing Surgical Trends By A Surgical System" filed Dec. 30, 2019, U.S. patent application Ser. No. 16/729,747 entitled "Dynamic Surgical Visualization Systems" filed Dec. 30, 2019, U.S. patent application Ser. No. 16/729,744 entitled "Visualization Systems Using Structured Light" filed Dec. 30, 2019, U.S. patent application Ser. No. 16/729,778 entitled "System And Method For Determining, Adjusting, And Managing Resection Margin About A Subject Tissue" filed Dec. 30, 2019, U.S. patent application Ser. No. 16/729,729 entitled "Surgical Systems For Proposing And Corroborating Organ Portion Removals" filed Dec. 30, 2019, U.S. patent application Ser. No. 16/729,778 entitled "Surgical System For Overlaying Surgical Instrument Data Onto A Virtual Three Dimensional Construct Of An Organ" filed Dec. 30, 2019, U.S. patent application Ser. No. 16/729,751 entitled "Surgical Systems For Generating Three Dimensional Constructs Of Anatomical Organs And Coupling Identified Anatomical Structures Thereto" filed Dec. 30, 2019, U.S. patent application Ser. No. 16/729,740 entitled "Surgical Systems Correlating Visualization Data And Powered Surgical Instrument Data" filed Dec. 30, 2019, U.S. patent application Ser. No. 16/729,737 entitled "Adaptive Surgical System Control According To Surgical Smoke Cloud Characteristics" filed Dec. 30, 2019, U.S. patent application Ser. No. 16/729,796 entitled "Adaptive Surgical System Control According To Surgical Smoke Particulate Characteristics" filed Dec. 30, 2019, U.S. patent application Ser. No. 16/729,803 entitled "Adaptive Visualization By A Surgical System" filed Dec. 30, 2019, U.S. patent application Ser. No. 16/729,807 entitled "Method Of Using Imaging Devices In Surgery" filed Dec. 30, 2019, U.S. Pat. App No. 63/249,644 entitled "Surgical Devices, Systems, And Methods Using Multi-Source Imaging" filed on Sep. 29, 2021, U.S. Pat. App No. 63/249,652 entitled "Surgical Devices, Systems, Methods Using Fiducial Identification And Tracking" filed on Sep. 29, 2021, U.S. Pat. App No. 63/249,658 entitled "Surgical Devices, Systems, And Methods For Control Of One Visualization With Another" filed on Sep. 29, 2021, U.S. Pat. App No. 63/249,877 entitled "Methods And Systems For Controlling Cooperative Surgical Instruments" filed on Sep. 29, 2021, and U.S. Pat. App No. 63/249,980 entitled "Cooperative Access" filed on Sep. 29, 2021, which are hereby incorporated by reference in their entireties.

Surgical Hubs

The various visualization or imaging systems described herein can be incorporated into a system that includes a surgical hub. In general, a surgical hub can be a component of a comprehensive digital medical system capable of spanning multiple medical facilities and configured to provide integrated and comprehensive improved medical care to a vast number of patients. The comprehensive digital medical system includes a cloud-based medical analytics system that is configured to interconnect to multiple surgical hubs located across many different medical facilities. The surgical hubs are configured to interconnect with one or more elements, such as one or more surgical instruments that are used to conduct medical procedures on patients and/or one or more visualization systems that are used during performance of medical procedures. The surgical hubs provide a wide array of functionality to improve the outcomes of medical procedures. The data generated by the various surgical devices, visualization systems, and surgical hubs about the patient and the medical procedure may be transmitted to the cloud-based medical analytics system. This data may then be aggregated with similar data gathered from many other surgical hubs, visualization systems, and surgical instruments located at other medical facilities. Various patterns and correlations may be found through the cloud-based analytics system analyzing the collected data. Improvements in the techniques used to generate the data may be generated as a result, and these improvements may then be disseminated to the various surgical hubs, visualization systems, and surgical instruments. Due to the interconnectedness of all of the aforementioned components, improvements in medical procedures and practices may be found that otherwise may not be found if the many components were not so interconnected.

Examples of surgical hubs configured to receive, analyze, and output data, and methods of using such surgical hubs, are further described in U.S. Pat. Pub. No. 2019/0200844 entitled "Method Of Hub Communication, Processing, Storage And Display" filed Dec. 4, 2018, U.S. Pat. Pub. No. 2019/0200981 entitled "Method Of Compressing Tissue Within A Stapling Device And Simultaneously Displaying The Location Of The Tissue Within The Jaws" filed Dec. 4, 2018, U.S. Pat. Pub. No. 2019/0201046 entitled "Method For Controlling Smart Energy Devices" filed Dec. 4, 2018, U.S. Pat. Pub. No. 2019/0201114 entitled "Adaptive Control Program Updates For Surgical Hubs" filed Mar. 29, 2018, U.S. Pat. Pub. No. 2019/0201140 entitled "Surgical Hub Situational Awareness" filed Mar. 29, 2018, U.S. Pat. Pub. No. 2019/0206004 entitled "Interactive Surgical Systems With Condition Handling Of Devices And Data Capabilities" filed Mar. 29, 2018, U.S. Pat. Pub. No. 2019/0206555 entitled "Cloud-based Medical Analytics For Customization And Recommendations To A User" filed Mar. 29, 2018, and U.S. Pat. Pub. No. 2019/0207857 entitled "Surgical Network Determination Of Prioritization Of Communication, Interaction, Or Processing Based On System Or Device Needs" filed Nov. 6, 2018, which are hereby incorporated by reference in their entireties.

Figure 18:
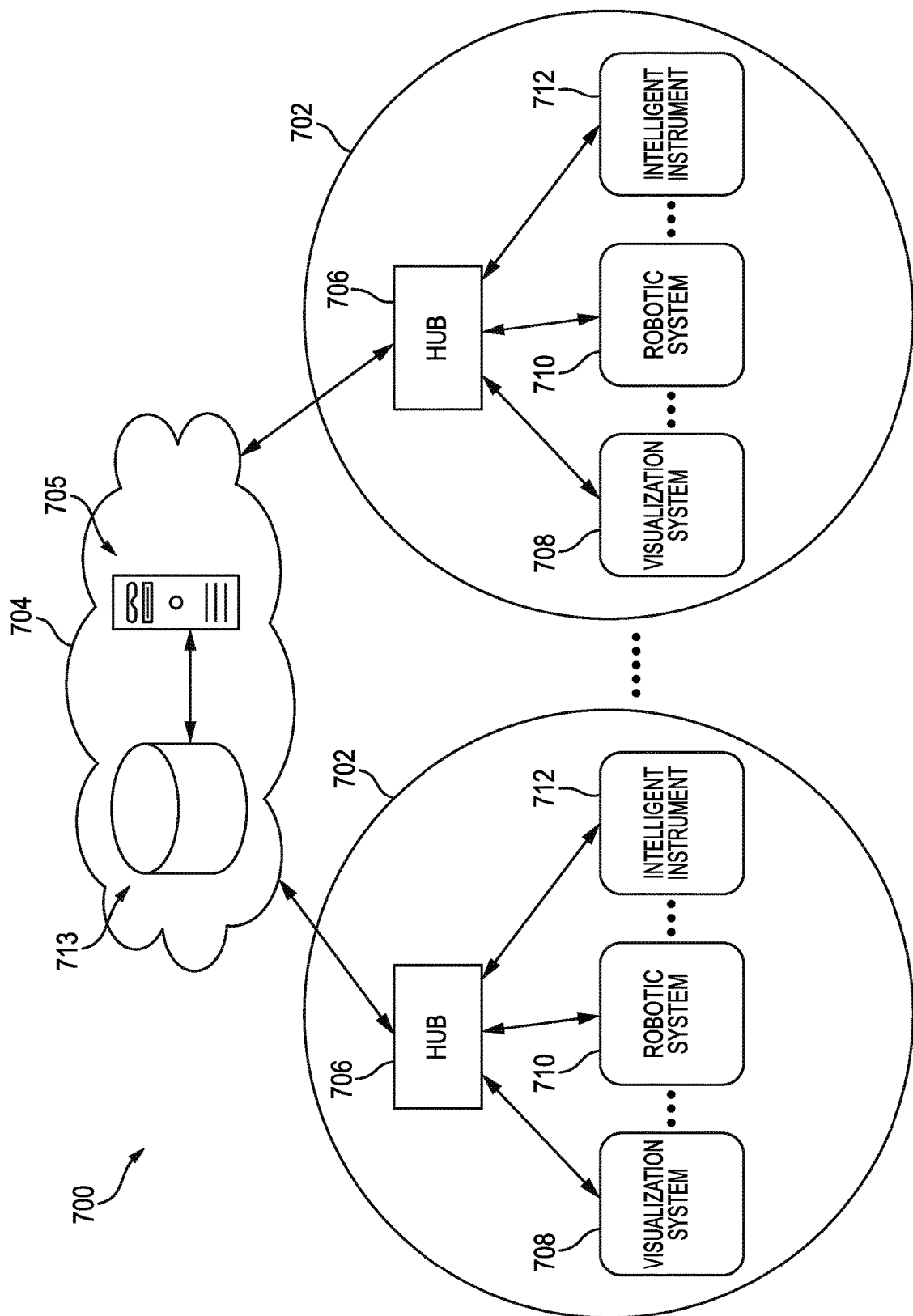
FIG. 18 is a schematic view of one embodiment of a computer-implemented interactive surgical system.

FIG. 18 illustrates one embodiment of a computer-implemented interactive surgical system 700 that includes one or more surgical systems 702 and a cloud-based system (e.g., a cloud 704 that can include a remote server 713 coupled to a storage device 705). Each surgical system 702 includes at least one surgical hub 706 in communication with the cloud 704. In one example, as illustrated in FIG. 18, the surgical system 702 includes a visualization system 708, a robotic system 710, and an intelligent (or "smart") surgical instrument 712, which are configured to communicate with one another and/or the hub 706. The intelligent surgical instrument 712 can include imaging device(s). The surgical system 702 can include an M number of hubs 706, an N number of visualization systems 708, an O number of robotic systems 710, and a P number of intelligent surgical instruments 712, where M, N, O, and P are integers greater than or equal to one that may or may not be equal to any one or more of each other. Various exemplary intelligent surgical instruments and robotic systems are described herein.

Data received by a surgical hub from a surgical visualization system can be used in any of a variety of ways. In an exemplary embodiment, the surgical hub can receive data from a surgical visualization system in use with a patient in a surgical setting, e.g., in use in an operating room during performance of a surgical procedure. The surgical hub can use the received data in any of one or more ways, as discussed herein.

The surgical hub can be configured to analyze received data in real time with use of the surgical visualization system and adjust control one or more of the surgical visualization system and/or one or more intelligent surgical instruments in use with the patient based on the analysis of the received data. Such adjustment can include, for example, adjusting one or operational control parameters of intelligent surgical instrument(s), causing one or more sensors of one or more intelligent surgical instruments to take a measurement to help gain an understanding of the patient's current physiological condition, and/or current operational status of an intelligent surgical instrument, and other adjustments. Controlling and adjusting operation of intelligent surgical instruments is discussed further below. Examples of operational control parameters of an intelligent surgical instrument include motor speed, cutting element speed, time, duration, level of energy application, and light emission. Examples of surgical hubs and of controlling and adjusting intelligent surgical instrument operation are described further in previously mentioned U.S. patent application Ser. No. 16/729,772 entitled "Analyzing Surgical Trends By A Surgical System" filed Dec. 30, 2019, U.S. patent application Ser. No. 16/729,747 entitled "Dynamic Surgical Visualization Systems" filed Dec. 30, 2019, U.S. patent application Ser. No. 16/729,744 entitled "Visualization Systems Using Structured Light" filed Dec. 30, 2019, U.S. patent application Ser. No. 16/729,778 entitled "System And Method For Determining, Adjusting, And Managing Resection Margin About A Subject Tissue" filed Dec. 30, 2019, U.S. patent application Ser. No. 16/729,729 entitled "Surgical Systems For Proposing And Corroborating Organ Portion Removals" filed Dec. 30, 2019, U.S. patent application Ser. No. 16/729,778 entitled "Surgical System For Overlaying Surgical Instrument Data Onto A Virtual Three Dimensional Construct Of An Organ" filed Dec. 30, 2019, U.S. patent application Ser. No. 16/729,751 entitled "Surgical Systems For Generating Three Dimensional Constructs Of Anatomical Organs And Coupling Identified Anatomical Structures Thereto" filed Dec. 30, 2019, U.S. patent application Ser. No. 16/729,740 entitled "Surgical Systems Correlating Visualization Data And Powered Surgical Instrument Data" filed Dec. 30, 2019, U.S. patent application Ser. No. 16/729,737 entitled "Adaptive Surgical System Control According To Surgical Smoke Cloud Characteristics" filed Dec. 30, 2019, U.S. patent application Ser. No. 16/729,796 entitled "Adaptive Surgical System Control According To Surgical Smoke Particulate Characteristics" filed Dec. 30, 2019, U.S. patent application Ser. No. 16/729,803 entitled "Adaptive Visualization By A Surgical System" filed Dec. 30, 2019, and U.S. patent application Ser. No. 16/729,807 entitled "Method Of Using Imaging Devices In Surgery" filed Dec. 30, 2019, and in U.S. patent application Ser. No. 17/068,857 entitled "Adaptive Responses From Smart Packaging Of Drug Delivery Absorbable Adjuncts" filed Oct. 13, 2020, U.S. patent application Ser. No. 17/068,858 entitled "Drug Administration Devices That Communicate With Surgical Hubs" filed Oct. 13, 2020, U.S. patent application Ser. No. 17/068,859 entitled "Controlling Operation Of Drug Administration Devices Using Surgical Hubs" filed Oct. 13, 2020, U.S. patent application Ser. No. 17/068,863 entitled "Patient Monitoring Using Drug Administration Devices" filed Oct. 13, 2020, U.S. patent application Ser. No. 17/068,865 entitled "Monitoring And Communicating Information Using Drug Administration Devices" filed Oct. 13, 2020, and U.S. patent application Ser. No. 17/068,867 entitled "Aggregating And Analyzing Drug Administration Data" filed Oct. 13, 2020, which are hereby incorporated by reference in their entireties.

The surgical hub can be configured to cause visualization of the received data to be provided in the surgical setting on a display so that a medical practitioner in the surgical setting can view the data and thereby receive an understanding of the operation of the imaging device(s) in use in the surgical setting. Such information provided via visualization can include text and/or images.

Figure 19:
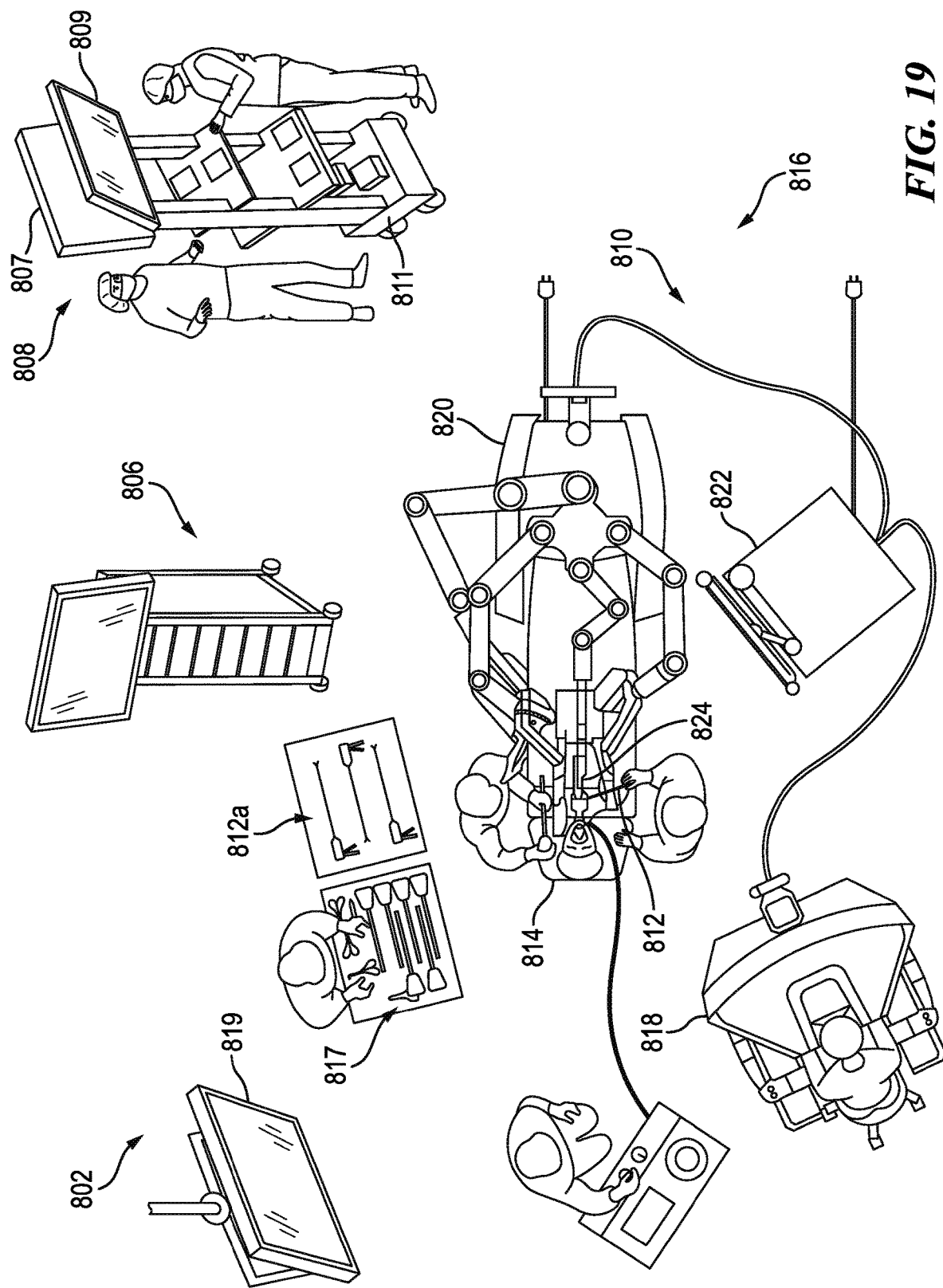
FIG. 19 is a schematic view of one embodiment a surgical system being used to perform a surgical procedure in an operating room.

FIG. 19 illustrates one embodiment of a surgical system 802 including a surgical hub 806 (e.g., the surgical hub 706 of FIG. 18 or other surgical hub described herein), a robotic surgical system 810 (e.g., the robotic surgical system 110 of FIG. 1 or other robotic surgical system herein), and a visualization system 808 (e.g., the visualization system 100 of FIG. 1 or other visualization system described herein). The surgical hub 806 can be in communication with a cloud, as discussed herein. FIG. 19 shows the surgical system 802 being used to perform a surgical procedure on a patient who is lying down on an operating table 814 in a surgical operating room 816. The robotic system 810 includes a surgeon's console 818, a patient side cart 820 (surgical robot), and a robotic system surgical hub 822. The robotic system surgical hub 822 is generally configured similar to the surgical hub 822 and can be in communication with a cloud. In some embodiments, the robotic system surgical hub 822 and the surgical hub 806 can be combined. The patient side cart 820 can manipulate an intelligent surgical tool 812 through a minimally invasive incision in the body of the patient while a medical practitioner, e.g., a surgeon, nurse, and/or other medical practitioner, views the surgical site through the surgeon's console 818. An image of the surgical site can be obtained by an imaging device 824 (e.g., the imaging device 120 of FIG. 1 or other imaging device described herein), which can be manipulated by the patient side cart 820 to orient the imaging device 824. The robotic system surgical hub 822 can be used to process the images of the surgical site for subsequent display to the surgeon through the surgeon's console 818.

A primary display 819 is positioned in the sterile field of the operating room 816 and is configured to be visible to an operator at the operating table 814. In addition, as in this illustrated embodiment, a visualization tower 818 can positioned outside the sterile field. The visualization tower 818 includes a first non-sterile display 807 and a second non-sterile display 809, which face away from each other. The visualization system 808, guided by the surgical hub 806, is configured to utilize the displays 807, 809, 819 to coordinate information flow to medical practitioners inside and outside the sterile field. For example, the surgical hub 806 can cause the visualization system 808 to display a snapshot and/or a video of a surgical site, as obtained by the imaging device 824, on one or both of the non-sterile displays 807, 809, while maintaining a live feed of the surgical site on the primary display 819. The snapshot and/or video on the non-sterile display 807 and/or 809 can permit a non-sterile medical practitioner to perform a diagnostic step relevant to the surgical procedure, for example.

The surgical hub 806 is configured to route a diagnostic input or feedback entered by a non-sterile medical practitioner at the visualization tower 818 to the primary display 819 within the sterile field, where it can be viewed by a sterile medical practitioner at the operating table 814. For example, the input can be in the form of a modification to the snapshot and/or video displayed on the non-sterile display 807 and/or 809, which can be routed to the primary display 819 by the surgical hub 806.

The surgical hub 806 is configured to coordinate information flow to a display of the intelligent surgical instrument 812, as is described in various U.S. Patent Applications that are incorporated by reference herein in the present disclosure. A diagnostic input or feedback entered by a non-sterile operator at the visualization tower 818 can be routed by the surgical hub 806 to the display 819 within the sterile field, where it can be viewed by the operator of the surgical instrument 812 and/or by other medical practitioner(s) in the sterile field.

The intelligent surgical instrument 812 and the imaging device 824, which is also an intelligent surgical tool, is being used with the patient in the surgical procedure as part of the surgical system 802. Other intelligent surgical instruments 812a that can be used in the surgical procedure, e.g., that can be removably coupled to the patient side cart 820 and be in communication with the robotic surgical system 810 and the surgical hub 806, are also shown in FIG. 19 as being available. Non-intelligent (or "dumb") surgical instruments 817, e.g., scissors, trocars, cannulas, scalpels, etc., that cannot be in communication with the robotic surgical system 810 and the surgical hub 806 are also shown in FIG. 19 as being available for use.

Operating Intelligent Surgical Instruments

An intelligent surgical device can have an algorithm stored thereon, e.g., in a memory thereof, configured to be executable on board the intelligent surgical device, e.g., by a processor thereof, to control operation of the intelligent surgical device. In some embodiments, instead of or in addition to being stored on the intelligent surgical device, the algorithm can be stored on a surgical hub, e.g., in a memory thereof, that is configured to communicate with the intelligent surgical device.

The algorithm is stored in the form of one or more sets of pluralities of data points defining and/or representing instructions, notifications, signals, etc. to control functions of the intelligent surgical device. In some embodiments, data gathered by the intelligent surgical device can be used by the intelligent surgical device, e.g., by a processor of the intelligent surgical device, to change at least one variable parameter of the algorithm. As discussed above, a surgical hub can be in communication with an intelligent surgical device, so data gathered by the intelligent surgical device can be communicated to the surgical hub and/or data gathered by another device in communication with the surgical hub can be communicated to the surgical hub, and data can be communicated from the surgical hub to the intelligent surgical device. Thus, instead of or in addition to the intelligent surgical device being configured to change a stored variable parameter, the surgical hub can be configured to communicate the changed at least one variable, alone or as part of the algorithm, to the intelligent surgical device and/or the surgical hub can communicate an instruction to the intelligent surgical device to change the at least one variable as determined by the surgical hub.

The at least one variable parameter is among the algorithm's data points, e.g., are included in instructions for operating the intelligent surgical device, and are thus each able to be changed by changing one or more of the stored pluralities of data points of the algorithm. After the at least one variable parameter has been changed, subsequent execution of the algorithm is according to the changed algorithm. As such, operation of the intelligent surgical device over time can be managed for a patient to increase the beneficial results use of the intelligent surgical device by taking into consideration actual situations of the patient and actual conditions and/or results of the surgical procedure in which the intelligent surgical device is being used. Changing the at least one variable parameter is automated to improve patient outcomes. Thus, the intelligent surgical device can be configured to provide personalized medicine based on the patient and the patient's surrounding conditions to provide a smart system. In a surgical setting in which the intelligent surgical device is being used during performance of a surgical procedure, automated changing of the at least one variable parameter may allow for the intelligent surgical device to be controlled based on data gathered during the performance of the surgical procedure, which may help ensure that the intelligent surgical device is used efficiently and correctly and/or may help reduce chances of patient harm by harming a critical anatomical structure.

The at least one variable parameter can be any of a variety of different operational parameters. Examples of variable parameters include motor speed, motor torque, energy level, energy application duration, tissue compression rate, jaw closure rate, cutting element speed, load threshold, etc.

Figure 20:
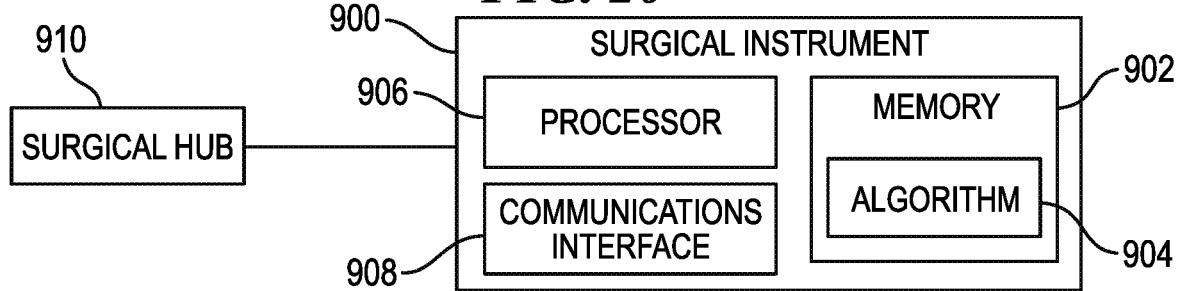
FIG. 20 is a schematic view of one embodiment of a surgical system including a smart surgical instrument and a surgical hub.

FIG. 20 illustrates one embodiment of an intelligent surgical instrument 900 including a memory 902 having an algorithm 904 stored therein that includes at least one variable parameter. The algorithm 904 can be a single algorithm or can include a plurality of algorithms, e.g., separate algorithms for different aspects of the surgical instrument's operation, where each algorithm includes at least one variable parameter. The intelligent surgical instrument 900 can be the surgical device 102 of FIG. 1, the imaging device 120 of FIG. 1, the surgical device 202 of FIG. 8, the imaging device 220 of FIG. 8, the surgical device 402 of FIG. 15, the surgical device 502a of FIG. 17, the surgical device 502b of FIG. 17, the surgical device 712 of FIG. 18, the surgical device 812 of FIG. 19, the imaging device 824 of FIG. 19, or other intelligent surgical instrument. The surgical instrument 900 also includes a processor 906 configured to execute the algorithm 904 to control operation of at least one aspect of the surgical instrument

900. To execute the algorithm 904, the processor 906 is configured to run a program stored in the memory 902 to access a plurality of data points of the algorithm 904 in the memory 902.

The surgical instrument 900 also includes a communications interface 908, e.g., a wireless transceiver or other wired or wireless communications interface, configured to communicate with another device, such as a surgical hub 910. The communications interface 908 can be configured to allow one-way communication, such as providing data to a remote server (e.g., a cloud server or other server) and/or to a local, surgical hub server, and/or receiving instructions or commands from a remote server and/or a local, surgical hub server, or two-way communication, such as providing information, messages, data, etc. regarding the surgical instrument 900 and/or data stored thereon and receiving instructions, such as from a doctor; a remote server regarding updates to software; a local, surgical hub server regarding updates to software; etc.

The surgical instrument 900 is simplified in FIG. 20 and can include additional components, e.g., a bus system, a handle, a elongate shaft having an end effector at a distal end thereof, a power source, etc. The processor 906 can also be configured to execute instructions stored in the memory 902 to control the device 900 generally, including other electrical components thereof such as the communications interface 908, an audio speaker, a user interface, etc.

The processor 906 is configured to change at least one variable parameter of the algorithm 904 such that a subsequent execution of the algorithm 904 will be in accordance with the changed at least one variable parameter. To change the at least one variable parameter of the algorithm 904, the processor 906 is configured to modify or update the data point(s) of the at least one variable parameter in the memory 902. The processor 906 can be configured to change the at least one variable parameter of the algorithm 904 in real time with use of the surgical device 900 during performance of a surgical procedure, which may accommodate real time conditions.

Additionally or alternatively to the processor 906 changing the at least one variable parameter, the processor 906 can be configured to change the algorithm 904 and/or at least one variable parameter of the algorithm 904 in response to an instruction received from the surgical hub 910. In some embodiments, the processor 906 is configured to change the at least one variable parameter only after communicating with the surgical hub 910 and receiving an instruction therefrom, which may help ensure coordinated action of the surgical instrument 900 with other aspects of the surgical procedure in which the surgical instrument 900 is being used.

In an exemplary embodiment, the processor 906 executes the algorithm 904 to control operation of the surgical instrument 900, changes the at least one variable parameter of the algorithm 904 based on real time data, and executes the algorithm 904 after changing the at least one variable parameter to control operation of the surgical instrument 900.

Figure 21:
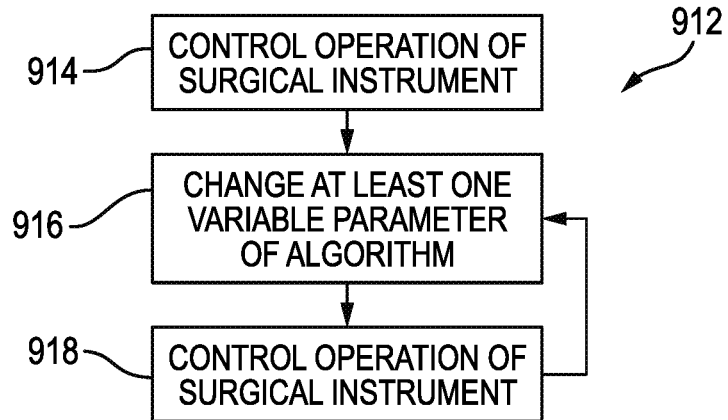
FIG. 21 is a flowchart showing a method of controlling the smart surgical instrument of FIG. 20.

FIG. 21 illustrates one embodiment of a method 912 of using of the surgical instrument 900 including a change of at least one variable parameter of the algorithm 904. The processor 906 controls 914 operation of the surgical instrument 900 by executing the algorithm 904 stored in the memory 902. Based on any of this subsequently known data and/or subsequently gathered data, the processor 904 changes 916 the at least one variable parameter of the algorithm 904 as discussed above. After changing the at least one variable parameter, the processor 906 controls 918 operation of the surgical instrument 900 by executing the algorithm 904, now with the changed at least one variable parameter. The processor 904 can change 916 the at least one variable parameter any number of times during performance of a surgical procedure, e.g., zero, one, two, three, etc. During any part of the method 912, the surgical instrument 900 can communicate with one or more computer systems, e.g., the surgical hub 910, a remote server such as a cloud server, etc., using the communications interface 908 to provide data thereto and/or receive instructions therefrom.

Situational Awareness

Operation of an intelligent surgical instrument can be altered based on situational awareness of the patient. The operation of the intelligent surgical instrument can be altered manually, such as by a user of the intelligent surgical instrument handling the instrument differently, providing a different input to the instrument, ceasing use of the instrument, etc. Additionally or alternatively, the operation of an intelligent surgical instrument can be changed automatically by an algorithm of the instrument being changed, e.g., by changing at least one variable parameter of the algorithm. As mentioned above, the algorithm can be adjusted automatically without user input requesting the change. Automating the adjustment during performance of a surgical procedure may help save time, may allow medical practitioners to focus on other aspects of the surgical procedure, and/or may ease the process of using the surgical instrument for a medical practitioner, which each may improve patient outcomes, such as by avoiding a critical structure, controlling the surgical instrument with consideration of a tissue type the instrument is being used on and/or near, etc.

The visualization systems described herein can be utilized as part of a situational awareness system that can be embodied or executed by a surgical hub, e.g., the surgical hub 706, the surgical hub 806, or other surgical hub described herein. In particular, characterizing, identifying, and/or visualizing surgical instruments (including their positions, orientations, and actions), tissues, structures, users, and/or other things located within the surgical field or the operating theater can provide contextual data that can be utilized by a situational awareness system to infer various information, such as a type of surgical procedure or a step thereof being performed, a type of tissue(s) and/or structure(s) being manipulated by a surgeon or other medical practitioner, and other information. The contextual data can then be utilized by the situational awareness system to provide alerts to a user, suggest subsequent steps or actions for the user to undertake, prepare surgical devices in anticipation for their use (e.g., activate an electrosurgical generator in anticipation of an electrosurgical instrument being utilized in a subsequent step of the surgical procedure, etc.), control operation of intelligent surgical instruments (e.g., customize surgical instrument operational parameters of an algorithm as discussed further below), and so on.

Although an intelligent surgical device including an algorithm that responds to sensed data, e.g., by having at least one variable parameter of the algorithm changed, can be an improvement over a "dumb" device that operates without accounting for sensed data, some sensed data can be incomplete or inconclusive when considered in isolation, e.g., without the context of the type of surgical procedure being performed or the type of tissue that is being operated on. Without knowing the procedural context (e.g., knowing the type of tissue being operated on or the type of procedure being performed), the algorithm may control the surgical device incorrectly or sub-optimally given the particular context-free sensed data. For example, the optimal manner for an algorithm to control a surgical instrument in response to a particular sensed parameter can vary according to the particular tissue type being operated on. This is due to the fact that different tissue types have different properties (e.g., resistance to tearing, ease of being cut, etc.) and thus respond differently to actions taken by surgical instruments. Therefore, it may be desirable for a surgical instrument to take different actions even when the same measurement for a particular parameter is sensed. As one example, the optimal manner in which to control a surgical stapler in response to the surgical stapler sensing an unexpectedly high force to close its end effector will vary depending upon whether the tissue type is susceptible or resistant to tearing. For tissues that are susceptible to tearing, such as lung tissue, the surgical instrument's control algorithm would optimally ramp down the motor in response to an unexpectedly high force to close to avoid tearing the tissue, e.g., change a variable parameter controlling motor speed or torque so the motor is slower. For tissues that are resistant to tearing, such as stomach tissue, the instrument's algorithm would optimally ramp up the motor in response to an unexpectedly high force to close to ensure that the end effector is clamped properly on the tissue, e.g., change a variable parameter controlling motor speed or torque so the motor is faster. Without knowing whether lung or stomach tissue has been clamped, the algorithm may be sub-optimally changed or not changed at all.

A surgical hub can be configured to derive information about a surgical procedure being performed based on data received from various data sources and then control modular devices accordingly. In other words, the surgical hub can be configured to infer information about the surgical procedure from received data and then control the modular devices operably coupled to the surgical hub based upon the inferred context of the surgical procedure. Modular devices can include any surgical device that is controllable by a situational awareness system, such as visualization system devices (e.g., a camera, a display screen, etc.), smart surgical instruments (e.g., an ultrasonic surgical instrument, an electrosurgical instrument, a surgical stapler, smoke evacuators, scopes, etc.). A modular device can include sensor(s)s configured to detect parameters associated with a patient with which the device is being used and/or associated with the modular device itself.

The contextual information derived or inferred from the received data can include, for example, a type of surgical procedure being performed, a particular step of the surgical procedure that the surgeon (or other medical practitioner) is performing, a type of tissue being operated on, or a body cavity that is the subject of the surgical procedure. The situational awareness system of the surgical hub can be configured to derive the contextual information from the data received from the data sources in a variety of different ways. In an exemplary embodiment, the contextual information received by the situational awareness system of the surgical hub is associated with a particular control adjustment or set of control adjustments for one or more modular devices. The control adjustments each correspond to a variable parameter. In one example, the situational awareness system includes a pattern recognition system, or machine learning system (e.g., an artificial neural network), that has been trained on training data to correlate various inputs (e.g., data from databases, patient monitoring devices, and/or modular devices) to corresponding contextual information regarding a surgical procedure. In other words, a machine learning system can be trained to accurately derive contextual information regarding a surgical procedure from the provided inputs. In another example, the situational awareness system can include a lookup table storing pre-characterized contextual information regarding a surgical procedure in association with one or more inputs (or ranges of inputs) corresponding to the contextual information. In response to a query with one or more inputs, the lookup table can return the corresponding contextual information for the situational awareness system for controlling at least one modular device. In another example, the situational awareness system includes a further machine learning system, lookup table, or other such system, which generates or retrieves one or more control adjustments for one or more modular devices when provided the contextual information as input.

A surgical hub including a situational awareness system may provide any number of benefits for a surgical system. One benefit includes improving the interpretation of sensed and collected data, which would in turn improve the processing accuracy and/or the usage of the data during the course of a surgical procedure. Another benefit is that the situational awareness system for the surgical hub may improve surgical procedure outcomes by allowing for adjustment of surgical instruments (and other modular devices) for the particular context of each surgical procedure (such as adjusting to different tissue types) and validating actions during a surgical procedure. Yet another benefit is that the situational awareness system may improve surgeon's and/or other medical practitioners' efficiency in performing surgical procedures by automatically suggesting next steps, providing data, and adjusting displays and other modular devices in the surgical theater according to the specific context of the procedure. Another benefit includes proactively and automatically controlling modular devices according to the particular step of the surgical procedure that is being performed to reduce the number of times that medical practitioners are required to interact with or control the surgical system during the course of a surgical procedure, such as by a situationally aware surgical hub proactively activating a generator to which an RF electrosurgical instrument is connected if it determines that a subsequent step of the procedure requires the use of the instrument. Proactively activating the energy source allows the instrument to be ready for use a soon as the preceding step of the procedure is completed.

For example, a situationally aware surgical hub can be configured to determine what type of tissue is being operated on. Therefore, when an unexpectedly high force to close a surgical instrument's end effector is detected, the situationally aware surgical hub can be configured to correctly ramp up or ramp down a motor of the surgical instrument for the type of tissue, e.g., by changing or causing change of at least one variable parameter of an algorithm for the surgical instrument regarding motor speed or torque.

For another example, a type of tissue being operated can affect adjustments that are made to compression rate and load thresholds of a surgical stapler for a particular tissue gap measurement. A situationally aware surgical hub can be configured to infer whether a surgical procedure being performed is a thoracic or an abdominal procedure, allowing the surgical hub to determine whether the tissue clamped by an end effector of the surgical stapler is lung tissue (for a thoracic procedure) or stomach tissue (for an abdominal procedure). The surgical hub can then be configured to cause adjustment of the compression rate and load thresholds of the surgical stapler appropriately for the type of tissue, e.g., by changing or causing change of at least one variable parameter of an algorithm for the surgical stapler regarding compression rate and load threshold.

As yet another example, a type of body cavity being operated in during an insufflation procedure can affect the function of a smoke evacuator. A situationally aware surgical hub can be configured to determine whether the surgical site is under pressure (by determining that the surgical procedure is utilizing insufflation) and determine the procedure type. As a procedure type is generally performed in a specific body cavity, the surgical hub can be configured to control a motor rate of the smoke evacuator appropriately for the body cavity being operated in, e.g., by changing or causing change of at least one variable parameter of an algorithm for the smoke evacuator regarding motor rate. Thus, a situationally aware surgical hub may provide a consistent amount of smoke evacuation for both thoracic and abdominal procedures.

As yet another example, a type of procedure being performed can affect the optimal energy level for an ultrasonic surgical instrument or radio frequency (RF) electrosurgical instrument to operate at. Arthroscopic procedures, for example, require higher energy levels because an end effector of the ultrasonic surgical instrument or RF electrosurgical instrument is immersed in fluid. A situationally aware surgical hub can be configured to determine whether the surgical procedure is an arthroscopic procedure. The surgical hub can be configured to adjust an RF power level or an ultrasonic amplitude of the generator (e.g., adjust energy level) to compensate for the fluid filled environment, e.g., by changing or causing change of at least one variable parameter of an algorithm for the instrument and/or a generator regarding energy level. Relatedly, a type of tissue being operated on can affect the optimal energy level for an ultrasonic surgical instrument or RF electrosurgical instrument to operate at. A situationally aware surgical hub can be configured to determine what type of surgical procedure is being performed and then customize the energy level for the ultrasonic surgical instrument or RF electrosurgical instrument, respectively, according to the expected tissue profile for the surgical procedure, e.g., by changing or causing change of at least one variable parameter of an algorithm for the instrument and/or a generator regarding energy level. Furthermore, a situationally aware surgical hub can be configured to adjust the energy level for the ultrasonic surgical instrument or RF electrosurgical instrument throughout the course of a surgical procedure, rather than just on a procedure-by-procedure basis. A situationally aware surgical hub can be configured to determine what step of the surgical procedure is being performed or will subsequently be performed and then update the control algorithm(s) for the generator and/or ultrasonic surgical instrument or RF electrosurgical instrument to set the energy level at a value appropriate for the expected tissue type according to the surgical procedure step.

As another example, a situationally aware surgical hub can be configured to determine whether the current or subsequent step of a surgical procedure requires a different view or degree of magnification on a display according to feature(s) at the surgical site that the surgeon and/or other medical practitioner is expected to need to view. The surgical hub can be configured to proactively change the displayed view (supplied by, e.g., an imaging device for a visualization system) accordingly so that the display automatically adjusts throughout the surgical procedure.

As yet another example, a situationally aware surgical hub can be configured to determine which step of a surgical procedure is being performed or will subsequently be performed and whether particular data or comparisons between data will be required for that step of the surgical procedure. The surgical hub can be configured to automatically call up data screens based upon the step of the surgical procedure being performed, without waiting for the surgeon or other medical practitioner to ask for the particular information.

As another example, a situationally aware surgical hub can be configured to determine whether a surgeon and/or other medical practitioner is making an error or otherwise deviating from an expected course of action during the course of a surgical procedure, e.g., as provided in a preoperative surgical plan. For example, the surgical hub can be configured to determine a type of surgical procedure being performed, retrieve a corresponding list of steps or order of equipment usage (e.g., from a memory), and then compare the steps being performed or the equipment being used during the course of the surgical procedure to the expected steps or equipment for the type of surgical procedure that the surgical hub determined is being performed. The surgical hub can be configured to provide an alert (visual, audible, and/or tactile) indicating that an unexpected action is being performed or an unexpected device is being utilized at the particular step in the surgical procedure.

In certain instances, operation of a robotic surgical system, such as any of the various robotic surgical systems described herein, can be controlled by the surgical hub based on its situational awareness and/or feedback from the components thereof and/or based on information from a cloud (e.g., the cloud 713 of FIG. 18).

Embodiments of situational awareness systems and using situational awareness systems during performance of a surgical procedure are described further in previously mentioned U.S. patent application Ser. No. 16/729,772 entitled "Analyzing Surgical Trends By A Surgical System" filed Dec. 30, 2019, U.S. patent application Ser. No. 16/729,747 entitled "Dynamic Surgical Visualization Systems" filed Dec. 30, 2019, U.S. patent application Ser. No. 16/729,744 entitled "Visualization Systems Using Structured Light" filed Dec. 30, 2019, U.S. patent application Ser. No. 16/729,778 entitled "System And Method For Determining, Adjusting, And Managing Resection Margin About A Subject Tissue" filed Dec. 30, 2019, U.S. patent application Ser. No. 16/729,729 entitled "Surgical Systems For Proposing And Corroborating Organ Portion Removals" filed Dec. 30, 2019, U.S. patent application Ser. No. 16/729,778 entitled "Surgical System For Overlaying Surgical Instrument Data Onto A Virtual Three Dimensional Construct Of An Organ" filed Dec. 30, 2019, U.S. patent application Ser. No. 16/729,751 entitled "Surgical Systems For Generating Three Dimensional Constructs Of Anatomical Organs And Coupling Identified Anatomical Structures Thereto" filed Dec. 30, 2019, U.S. patent application Ser. No. 16/729,740 entitled "Surgical Systems Correlating Visualization Data And Powered Surgical Instrument Data" filed Dec. 30, 2019, U.S. patent application Ser. No. 16/729,737 entitled "Adaptive Surgical System Control According To Surgical Smoke Cloud Characteristics" filed Dec. 30, 2019, U.S. patent application Ser. No. 16/729,796 entitled "Adaptive Surgical System Control According To Surgical Smoke Particulate Characteristics" filed Dec. 30, 2019, U.S. patent application Ser. No. 16/729,803 entitled "Adaptive Visualization By A Surgical System" filed Dec. 30, 2019, and U.S. patent application Ser. No. 16/729,807 entitled "Method Of Using Imaging Devices In Surgery" filed Dec. 30, 2019.

Surgical Procedures of the Lung

Various aspects of the devices, systems, and methods described herein may relate to a surgical procedure performed on a lung. For example, a lung resection, e.g., a lobectomy, is a surgical procedure in which all or part, e.g., one or more lobes, of a lung is removed. The purpose of performing a lung resection is to treat a damaged or diseased lung as a result of, for example, lung cancer, emphysema, or bronchiectasis.

During a lung resection, the lung or lungs are first deflated, and thereafter one or more incisions are made on the patient's side between the patient's ribs to reach the lungs laparoscopically. Surgical instruments, such as graspers and a laparoscope, are inserted through the incision. Once the infected or damaged area of the lung is identified, the area is dissected from the lung and removed from the one or more incisions. The dissected area and the one or more incisions can be closed, for example, with a surgical stapler or stitches.

Since the lung is deflated during surgery, the lung, or certain portions thereof, may need to be mobilized to allow the surgical instruments to reach the surgical site. This mobilization can be carried out by grasping the outer tissue layer of the lung with graspers and applying a force to the lung through the graspers. However, the pleura and parenchyma of the lung are very fragile and therefore can be easily ripped or torn under the applied force. Additionally, during mobilization, the graspers can cut off blood supply to one or more areas of the lung.

Further, a breathing tube is placed into the patient's airway to allow each lung to be separately inflated during surgery. Inflation of the lung can cause the lung to move and match pre-operative imaging and/or allow the surgeon to check for leaks at the dissected area(s). However, by inflating the whole lung, working space is lost around the lung due to the filling of the thoracic cavity. Additionally, inflating a whole lung can take time and does not guarantee easy leak detection if multiple portions of the lung are operated on during the surgical procedure.

Surgical Procedures of the Colon

Figure 21A:
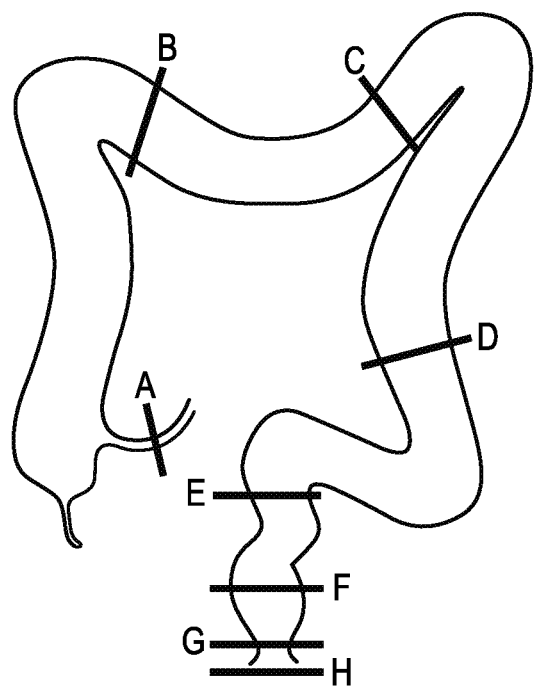
FIG. 21A is a schematic view of a colon illustrating major resections of the colon.

Various aspects of the devices, systems, and methods described herein may relate to a surgical procedure performed on a colon. For example, surgery is often the main treatment for early-stage colon cancers. The type of surgery used depends on the stage (extent) of the cancer, where it is in the colon, and the goal of the surgery. Some early colon cancers (stage 0 and some early stage I tumors) and most polyps can be removed during a colonoscopy. However, if the cancer has progressed, a local excision or colectomy may be required. A colectomy is surgery to remove all or part of the colon. In certain instances, nearby lymph nodes are also removed. If only part of the colon is removed, it is called a hemicolectomy, partial colectomy, or segmental resection in which the surgeon takes out the diseased part of the colon with a small segment of non-diseased colon on either side. Usually, about one-fourth to one-third of the colon is removed, depending on the size and location of the cancer. Major resections of the colon are illustrated in FIG. 21A, in which A-B is a right hemicolectomy, A-C is an extended right hemicolectomy, B-C is a transverse colectomy, C-E is a left hemicolectomy, D-E is a sigmoid colectomy, D-F is an anterior resection, D-G is a (ultra) low anterior resection, D-H is an abdomino-perineal resection, A-D is a subtotal colectomy, A-E is a total colectomy, and A-H is a total procto-colectomy. Once the resection is complete, the remaining intact sections of colon are then reattached.

A colectomy can be performed through an open colectomy, where a single incision through the abdominal wall is used to access the colon for separation and removal of the affected colon tissue, and through a laparoscopic-assisted colectomy. With a laparoscopic-assisted colectomy, the surgery is done through many smaller incisions with surgical instruments and a laparoscope passing through the small incisions to remove the entire colon or a part thereof. At the beginning of the procedure, the abdomen is inflated with gas, e.g., carbon dioxide, to provide a working space for the surgeon. The laparoscope transmits images inside the abdominal cavity, giving the surgeon a magnified view of the patient's internal organs on a monitor or other display. Several other cannulas are inserted to allow the surgeon to work inside and remove part(s) of the colon. Once the diseased parts of the colon are removed, the remaining ends of the colon are attached to each other, e.g., via staplers or stitches. The entire procedure may be completed through the cannulas or by lengthening one of the small cannula incisions.

During a laparoscopic-assisted colectomy procedure, it is often difficult to obtain an adequate operative field. Oftentimes, dissections are made deep in the pelvis which makes it difficult to obtain adequate visualization of the area. As a result, the lower rectum must be lifted and rotated to gain access to the veins and arteries around both sides of the rectum during mobilization. During manipulation of the lower rectum, bunching of tissue and/or overstretching of tissue can occur. Additionally, a tumor within the rectum can cause adhesions in the surrounding pelvis, and as a result, this can require freeing the rectal stump and mobilizing the mesentery and blood supply before transection and removal of the tumor.

Further, multiple graspers are needed to position the tumor for removal from the colon. During dissection of the colon, the tumor should be placed under tension, which requires grasping and stretching the surrounding healthy tissue of the colon. However, the manipulating of the tissue surrounding the tumor can suffer from reduced blood flow and trauma due to the graspers placing a high grip force on the tissue. Additionally, during a colectomy, the transverse colon and upper descending colon may need to be mobilized to allow the healthy, good remaining colon to be brought down to connect to the rectal stump after the section of the colon containing the tumor is transected and removed.

After a colectomy, the remaining healthy portions of the colon must be reattached to one another to create a path for waste to leave the body. However, when using laparoscopic instruments to perform the colectomy, one single entry port may not have a large enough range of motion to move the one end of the colon to a connecting portion of the colon. As such, a second entry port is therefore needed to laparoscopically insert surgical instruments to help mobilize the colon in order to properly position the colon.

Surgical Procedures of the Stomach

Various aspects of the devices, systems, and methods described herein may relate to a surgical procedure performed on a stomach. For example, surgery is the most common treatment for stomach cancer. When surgery is required for stomach cancer, the goal is to remove the entire tumor as well as a good margin of healthy stomach tissue around the tumor. Different procedures can be used to remove stomach cancer. The type of procedure used depends on what part of the stomach the cancer is located and how far it has grown into nearby areas. For example, endoscopic mucosal resection (EMR) and endoscopic submucosal dissection (ESD) are procedures on the stomach can be used to treat some early-stage cancers. These procedures do not require a cut in the skin, but instead the surgeon passes an endoscope down the throat and into the stomach of the patient. Surgical tools (e.g., MEGADYNE™ Tissue Dissector or Electrosurgical Pencils) are then passed through the working channel of the endoscope to remove the tumor and some layers of the normal stomach wall below and around it.

Other surgical procedures performed on a stomach include a subtotal (partial) or a total gastrectomy that can be performed as an open procedure. e.g., surgical instruments are inserted through a large incision in the skin of the abdomen, or as a laparoscopic procedure, e.g., surgical instruments are inserted into the abdomen through several small cuts. For example, a laparoscopic gastrectomy procedure generally involves insufflation of the abdominal cavity with carbon dioxide gas to a pressure of around 15 millimeters of mercury (mm Hg). The abdominal wall is pierced and a straight tubular cannula or trocar, such as a cannula or trocar having a diameter in a range of about 5 mm to about 10 mm, is then inserted into the abdominal cavity. A laparoscope connected to an operating room monitor is used to visualize the operative field and is placed through one of the trocar(s). Laparoscopic surgical instruments are placed through two or more additional cannulas or trocars for manipulation by medical practitioner(s), e.g., surgeon and surgical assistant(s), to remove the desired portion(s) of the stomach.

In certain instances, laparoscopic and endoscopic cooperative surgery can be used to remove gastric tumors. This cooperative surgery typically involves introduction of an endoscope, e.g., a gastroscope, and laparoscopic trocars. A laparoscope and tissue manipulation and dissection surgical instruments are introduced through the trocar. The tumor location can be identified via the endoscope and a cutting element that is inserted into the working channel of the endoscope is then used for submucosal resection around the tumor. A laparoscopic dissection surgical instrument is then used for seromuscular dissection adjacent the tumor margins to create an incision through the stomach wall. The tumor is then pivoted through this incision from the intraluminal space, e.g., inside the stomach, to the extraluminal space, e.g., outside of the stomach. A laparoscopic surgical instrument, e.g., an endocutter, can be used to then complete the transection of the tumor from the stomach wall and seal the incision.

Surgical Procedures of the Intestine

Various aspects of the devices, systems, and methods described herein may relate to a surgical procedure performed on an intestine. For example, a duodenal mucosal resurfacing (DMR) procedure can be performed endoscopically to treat insulin-resistant metabolic diseases such as type 2 diabetes. The DMR procedure can be an effective treatment because it affects detection of food. The DMR procedure inhibits duodenum function such that food tends to be sensed deeper in the intestine than normal, e.g., sensed after passage through the duodenum (which is the first part of the small intestine). The patient's body thus senses sugar deeper in the intestine than is typical and thus reacts to the sugar later than is typical such that glycemic control can be improved. The irregular function of the duodenum changes the body's typical response to the food and, through nervous system and chemical signals, causes the body to adapt its response to the glucose level to increase insulin levels.

In the DMR procedure, the duodenal mucosa is lifted, such as with saline, and then the mucosa is ablated, e.g., using an ablation device advanced into the duodenum through a working channel of an endoscope. Lifting the mucosa before ablation helps protect the duodenum's outer layers from being damaged by the ablation. After the mucosa is ablated, the mucosa later regenerates. Examples of ablation devices are NeuWave™ ablation probes (available from Ethicon US LLC of Cincinnati, OH). Another example of an ablation device is the Hyblate catheter ablation probe (available from Hyblate Medical of Misgav, Israel). Another example of an ablation device is the Barxx™ HaloFlex (available from Medtronic of Minneapolis, MN).

Figure 21B:
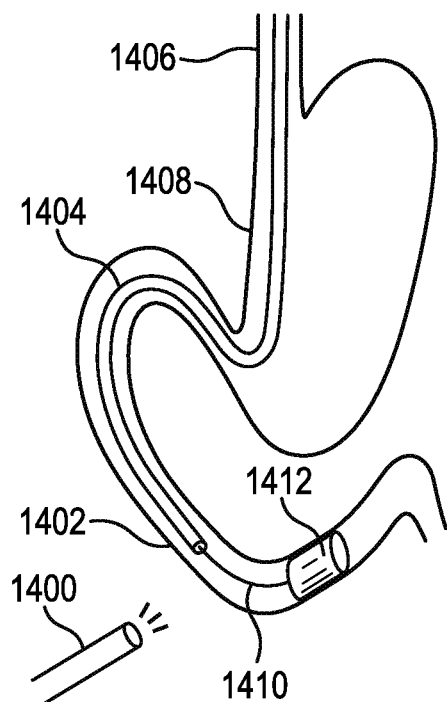
FIG. 21B is a perspective partial cross-sectional view of one embodiment of a duodenal mucosal resurfacing procedure.

FIG. 21B illustrates one embodiment of a DMR procedure. As shown in FIG. 21B, a laparoscope 1400 is positioned external to a duodenum 1402 for external visualization of the duodenum 1402. An endoscope 1404 is advanced transorally through an esophagus 1406, through a stomach 1408, and into the duodenum 1402 for internal visualization of the duodenum 1402. An ablation device 1410 is advanced through a working channel of the endoscope 1404 to extend distally from the endoscope 1404 into the duodenum 1402. A balloon 1412 of the ablation device 1410 is shown expanded or inflated in FIG. 21B. The expanded or inflated balloon 1412 can help center the ablation device's electrode so even circumferential ablating can occur before the ablation device 1410 is advanced and/or retracted to repeat ablation. Before the mucosa is ablated using the ablation device 1410, the duodenal mucosa is lifted, such as with saline. In some embodiments in addition to or instead of including the balloon 1412, the ablation device 1410 can be expandable/collapsible using an electrode array or basket configured to expand and collapse.

The laparoscope's external visualization of the duodenum 1402 can allow for thermal monitoring of the duodenum 1402, which may help ensure that the outer layers of the duodenum 1402 are not damaged by the ablation of the duodenal mucosa, such as by the duodenum being perforated. Various embodiments of thermal monitoring are discussed further, for example, below and in U.S. Pat. App No. 63/249,658 entitled "Surgical Devices, Systems, And Methods For Control Of One Visualization With Another" filed on Sep. 29, 2021. The endoscope 1404 and/or the ablation device 1410 can include a fiducial marker thereon that the laparoscope 1400 can be configured to visualize through the duodenum's tissue, e.g., by using invisible light, to help determine where the laparoscope 1400 should externally visualize the duodenum 1402 at a location where ablation occurs. Various embodiments of fiducial markers are discussed further, for example, in U.S. Pat. App No. 63/249,652 entitled "Surgical Devices, Systems, Methods Using Fiducial Identification And Tracking" filed on Sep. 29, 2021 and in U.S. Pat. App No. 63/249,658 entitled "Surgical Devices, Systems, And Methods For Control Of One Visualization With Another" filed on Sep. 29, 2021.

Control of Cooperative Surgical Instruments

In various aspects, the present disclosure provides methods, devices, and systems for the control of cooperative surgical instruments. For example, in one embodiment, a system can include a first surgical instrument configured to be inserted into a first portion of a body cavity of a patient and to operate on a first surgical treatment site in the body cavity, and a second surgical instrument configured to be inserted into a second portion of the body cavity and to operate on a second surgical treatment site in the body cavity. The system can also include first and second endoscopes. The first endoscope can have a first image sensor that can be positioned in the first portion of the body cavity so that the second surgical instrument is not within a field of view of the first image sensor. The second endoscope can also have a second image sensor that can be positioned in the second portion of the body cavity so that the first surgical instrument is not within a field of view of the second image sensor. A controller can be included in the system that is configured to receive the acquired first and second images, to determine a first location of the first surgical instrument and a second location of the surgical instrument, to determine a distance and orientation of the first surgical instrument relative to the second surgical instrument, and to cause movement of at least one of the first and second surgical instruments in the body cavity based on the determined distance and orientation. By causing movement based on the determined distance and orientation, the controller may help simplify movement of the two instruments for a user when the user is not able to directly see or visualize where the two instruments are relative to each other because of the obscured views of the two endoscopes. By simplifying movement between the two instruments, the controller may help to protect patient health and make surgical procedures more efficient.

Figure 22:
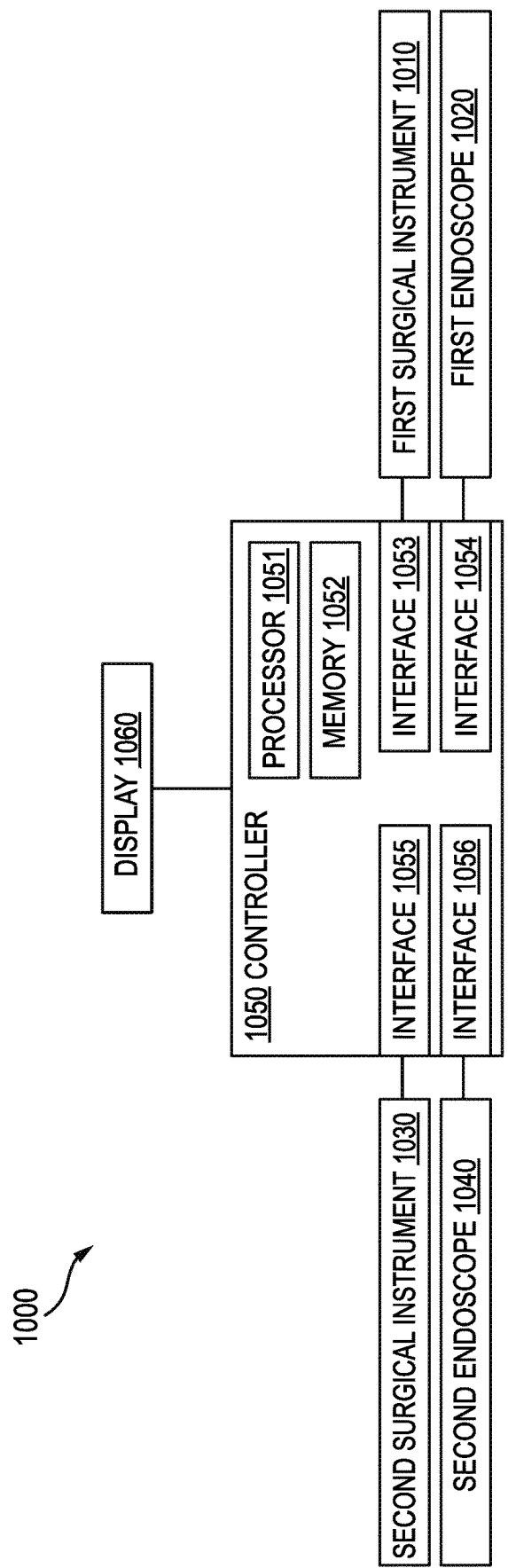
FIG. 22 is a schematic diagram of an exemplary surgical system that can provide for cooperative control of surgical instruments.

For example, FIG. 22 provides a schematic of one exemplary surgical system 1000 that can provide for cooperative control of surgical instruments regarding locations and movements of various instruments, such as the first and second surgical instruments discussed above. As shown, the system 1000 includes a first surgical instrument 1010, a second surgical instrument 1030, a first endoscope 1020, a second endoscope 1040, and a controller 1050.

The first surgical instrument 1010 and the second surgical instrument 1030 can each be any suitable surgical device configured to manipulate and/or treat tissue. The first surgical instrument 1010 and the second surgical instrument 1030 can each be similar to the surgical device 102 of FIG. 1, the surgical device 202 of FIG. 8, or other surgical device described herein. As mentioned above, examples of surgical devices include a surgical dissector, a surgical stapler, a surgical grasper, a clip applier, a smoke evacuator, a surgical energy device (e.g., mono-polar probes, bi-polar probes, ablation probes, an ultrasound device, an ultrasonic end effector, etc.), etc. For example, in some embodiments, the first surgical instrument 1010 and/or the second surgical instrument 1030 can include an end effector having opposing jaws that extend from a distal end of a shaft of the surgical device and that are configured to engage tissue therebetween.

The first endoscope 1020 and the second endoscope 1040 can each include an imaging device configured to acquire an image of a surgical site in a minimally invasive surgical procedure, including various flexible endoscopic systems with image sensors, as discussed above. The first endoscope 1020 and the second endoscope 1040 can each be similar to the imaging device 120 of FIG. 1, the imaging device 220 of FIG. 8, or other imaging device described herein. Although some implementations of the current subject matter are described herein as using one or more endoscopes to acquire images of the surgical site, any type of scope suitable for use in a minimally invasive surgical procedure can be used in conjunction with the systems, methods, and devices described herein. As mentioned above, examples of scopes include an arthroscope, an angioscope, a bronchoscope, a choledochoscope, a colonoscope, a cytoscope, a duodenoscope, an enteroscope, a double-balloon enteroscope, an esophagogastro-duodenoscope (gastroscope), a laryngoscope, a nasopharyngo-neproscope, a sigmoidoscope, a thoracoscope, an ureteroscope, an exoscope, and a self-propelling dual flex endoscope. One or more of these exemplary types of scopes can be used together in a minimally invasive surgical procedure in any feasible combination.

The controller 1050 includes a processor 1051 configured to perform one or more of operations and a memory 1052 that is configured to store instructions for causing the processor 1051 to perform the operations. The controller 1050 also includes a first surgical instrument interface 1053, a first endoscope interface 1054, a second surgical instrument interface 1055, and a second endoscope interface 1056. As shown in FIG. 22, the first surgical instrument 1010 is coupled to the controller 1050 via the first surgical instrument interface 1053 and as such can receive movement and actuation instructions from the processor 1051. The first endoscope 1020 is coupled to the controller 1050 via the first endoscope interface 1054 and as such can provide data characterizing images acquired by the first endoscope 1020 to the processor 1051, and/or the memory 1052 for later use by the processor 1051, for use by the processor 1051 in performing various ones of the operations. Similar to the first surgical instrument 1010, the second surgical instrument 1030 is coupled to the controller 1050 via the second surgical instrument interface 1055 and as such can receive movement and actuation instructions from the processor 1051. Similar to the first endoscope 1020, the second endoscope 1040 is coupled to the controller 1050 via the second endoscope interface 1056 and as such can provide data characterizing images acquired by the second endoscope 1040 to the processor 1051, and/or the memory 1052 for later use by the processor 1051, for use by the processor 1051 in performing various ones of the operations. In some embodiments, each of the first surgical instrument interface 1053, the first endoscope interface 1054, the second surgical instrument interface 1055, and the second endoscope interface 1056 may be different from one another so as to accommodate differences between the controller interfaces of each of the first surgical instrument 1010, the first endoscope 1020, the second surgical instrument 1030, and/or the second endoscope 1040. In some embodiments, the controller 1050 can determine first and second locations of the first and second surgical instruments 1010, 1030, respectively, relative to one another, and can determines a distance and orientation of the first surgical instrument 1010 relative to the second surgical instrument 1030, as discussed further below.

As shown, the system 1000 also includes a display 1060 that is operably coupled to the controller 1050 and configured to graphically depict the images acquired by one or more of the first endoscope 1020 and the second endoscope 1040. In the illustrated embodiment, the controller 1050 receives a stream of image data from each of the first endoscope 1020 and the second endoscope 1040, determines an image and/or video feed in real-time from the received image data, and provides images and/or video feeds to the display 1060 for depiction thereon and viewing by a user. In some embodiments, the controller 1050 can merge the first and second images together to create a merged image or virtual treatment site created from the first and second images that the surgeon uses during the procedure. Additional details regarding various embodiments of merged images are provided in, for example, previously mentioned U.S. App. No. 63/249,980 entitled "Cooperative Access" filed on Sep. 29, 2021.

The system 1000 can be used in a variety of different surgical procedures involving a variety of different surgical instruments and/or surgical implants. For example, the system 1000 can be used to visualize and control orientation of implants, control rates of advancement of various instruments, allow synchronized and/or cooperative actions between various instruments during various procedures, and allow determination of various tissue properties of surrounding tissue during various procedures, as further discussed below.

Figure 23:
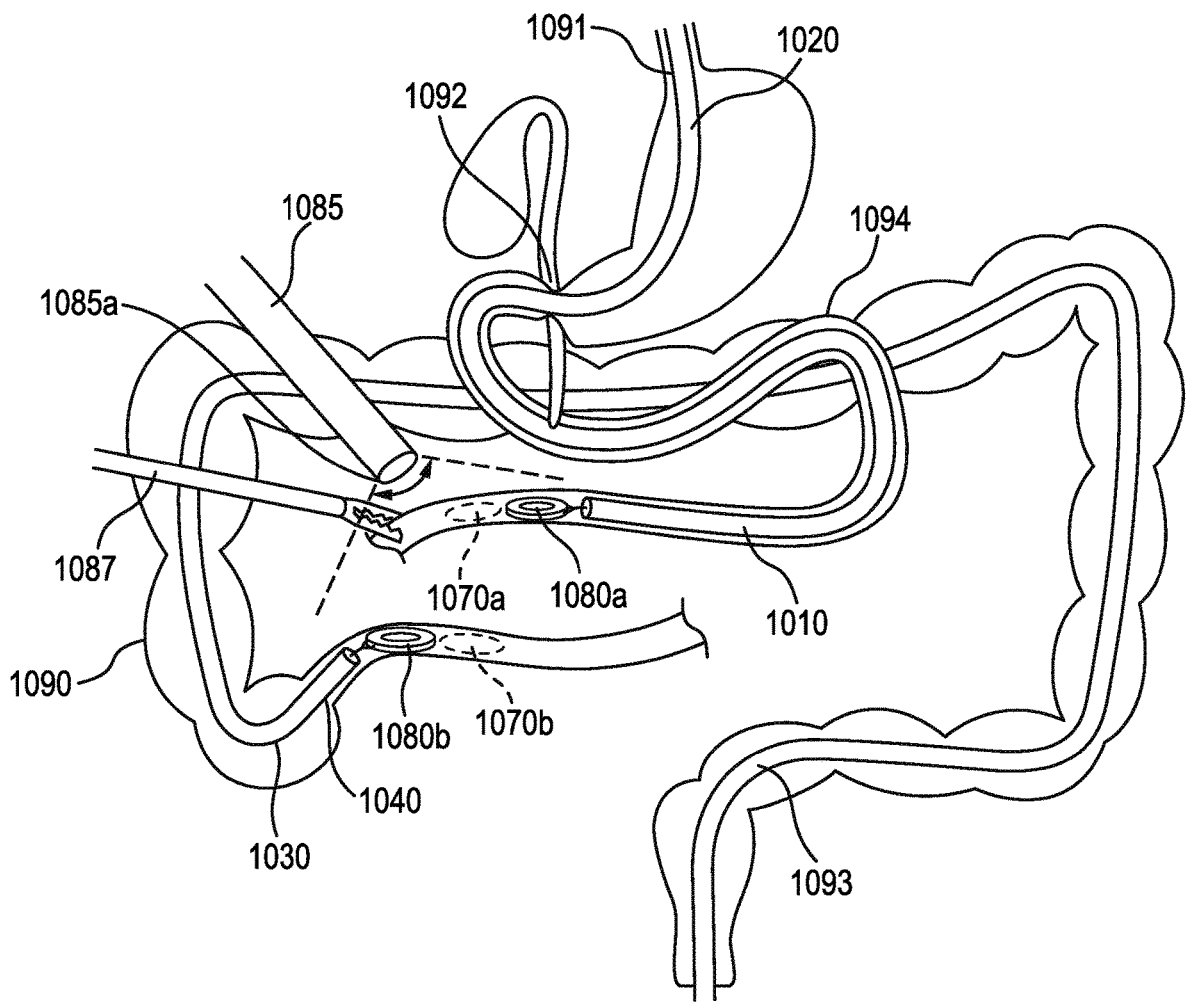
FIG. 23 is an illustrative view of an example embodiment of a system for providing a common field of view by augmenting multiple points of view into the common field of view via the use/tracking of sensors placed on a plurality of endoscopes placed in a surgical field.

FIG. 23 shows one embodiment of using the system 1000 in a partial jejunal diversion to cooperatively place a surgical implant, first and second implant parts 1080a, 1080b of a two-part magnetic anastomosis device in this illustrated embodiment, at a connected or joint surgical treatment site using the first and second endoscopes 1020, 1040 and the first and second surgical instruments 1010, 1030 that approach the surgical site from different directions and when it is not possible to visualize each of the surgical instruments 1010, 1030 and the two-part magnetic anastomosis device with a single one of the endoscopes 1020, 1040. A partial jejunal diversion is used to create a shorter metabolic pathway through a patient's jejunum (small intestines), such as to change a rate of GI motility and glucose implication of digested foods. However, the significant length of patients' jejunums compared to the limited lengths of common endoscopes and surgical instruments presents a challenge to users when using two separate endoscopes and two separate surgical instruments to place a two-part anastomosis device because the endoscopes usually or always cannot be able to directly visualize one another or the two-part anastomosis device to help with orientation and position of the two-part anastomosis device before deployment of the two-part anastomosis device. The illustrated embodiment allows orientations and distances of the surgical instruments 1010, 1030, the endoscopes 1020, 1040, and the implant parts 1080a, 1080b to be determined and controlled, as needed, to ensure correct alignment of the implant parts 1080a, 1080b before deployment. Furthermore, the system 1000 can be similarly used in other surgical procedures and with other implants.

As illustrated in FIG. 23, the first endoscope 1020 is inserted into a first natural orifice of a patient, a mouth in the illustrated embodiment, and steered and advanced through an esophageal sphincter 1091, a pyloric sphincter 1092, and a duodenojejunal flexure 1094 of the patient to a first surgical treatment site 1070a in a jejunum 1090 (or middle portion of the small intestines between the duodenum and the ileum) of the patient. The second endoscope 1040 is inserted into a second natural orifice of a patient, a rectum in this illustrated embodiment, and steered and advanced through an ileocecal valve 1093 to a second surgical treatment site 1070b in the jejunum 1090. The first and second surgical treatment sites 1070a, 1070b can be identified before insertion in some embodiments using various external imaging mechanisms, such as CT imaging, and the sites 1070a, 1070b can be confirmed in some embodiments after insertion of the endoscopes 1020, 1040 through using various external imaging such as CT imaging, through use of imaging from the endoscopes 1020, 1040 directly, through use of various additional instruments, such as a laparoscope 1085 shown in FIG. 23, etc. In some surgical procedures, the laparoscope 1085 may not be used.

In the illustrated embodiment, when the first and second endoscopes 1020, 1040 reach the first and second surgical treatment sites 1070a, 1070b, respectively, each endoscope 1020, 1040 detects its location with respect to the other endoscope 1020, 1040 so that both endoscopes 1020, 1040 can be positioned and oriented relative to one another at their respective surgical treatment sites 1070a, 1070b to help ensure successful delivery of the first and second implant parts 1080a, 1080b at each site 1070a, 1070b, respectively. The location and orientation of each endoscope 1020, 1040 is tracked by the controller 1050 of the system 1000 using electromagnetic (EM) tracked tips of each endoscope 1020, 1040 through magnetic field detection to determine locations and orientations of each endoscope 1020, 1040 in a global coordinate system of the system 1000, which is known by the controller 1050 in communication with each of the endoscopes 1020, 1040 and each of the surgical instruments 1010, 1030. While EM tracked tips are provided in the illustrated embodiment, alternative and/or additional tracking means can be used, such as fiber bragg grating, virtual tags, fiducial markers as discussed above, use of probes, identification of known anatomy, various 3D scanning techniques such as using structured light as discussed above, various sensors and/or imaging systems discussed above, etc. Additional details regarding various embodiments of tracking surgical instruments are provided in, for example, previously mentioned U.S. App. No. 63/249,980 entitled "Cooperative Access" filed on Sep. 29, 2021.

The first implant part 1080a of the two-part magnetic anastomosis device is releasably attached to a distal end of the first surgical instrument 1010, and the first surgical instrument 1010 with the first implant part 1080a is inserted through a working channel of the first endoscope 1020 until the first implant part 1080a and a distal-most portion of the first instrument 1010 are positioned distally beyond the first endoscope 1020 at the first surgical treatment site 1070a. Similarly, the second implant part 1080b of the two-part magnetic anastomosis device is releasably attached to a distal end of the second surgical instrument 1030, and the second surgical instrument 1030 with the second implant part 1080b is inserted through a working channel of the second endoscope 1040 until the second implant part 1080b and a distal-most portion of the second instrument 1030 are positioned distally beyond the second endoscope 1040 at the second surgical treatment site 1070b. In other embodiments, the first surgical instrument 1010 and/or the second surgical instrument 1030 can be advanced along an exterior of the first and second endoscopes 1020, 1040, respectively, instead of being advanced through a working channel.

Furthermore, the controller 1050 of the system 1000 controls forces and rates of advancement of the first and second instruments 1010, 1030 and the first and second endoscopes 1020, 1040 within the patient relative to each other and/or a rendezvous point. When tracking the first and second instruments 1010, 1030 and the first and second endoscopes 1020, 1040, the controller 1050 determines speed of advancement, approach vectors, appliable force, and/or distance from each other and/or distance from a rendezvous point, defining a location within the patient where the first and second implant parts 1080a, 1080b are intended to be joined together. As each of the instruments 1010, 1030 and/or endoscopes 1020, 1040 approach the rendezvous point, the advancement speed, the appliable force, and/or the detection sampling rate are changed by the controller 1050 to ensure that the approaching instruments 1010, 1030 and/or endoscopes 1020, 1040 do not impact or overshoot the rendezvous point and to allow more delicate or precise positioning of the corresponding instruments 1010, 1030 and/or endoscopes 1020, 1040. In some embodiments, the controller 1050 can also cause display of indications of the advancement speed, the approach vectors, the appliable force, the distance from each other, the distance from a rendezvous point (whatever that is intended to mean), and/or the detection sampling rate on a display, such as the display 1060.

Figure 24:
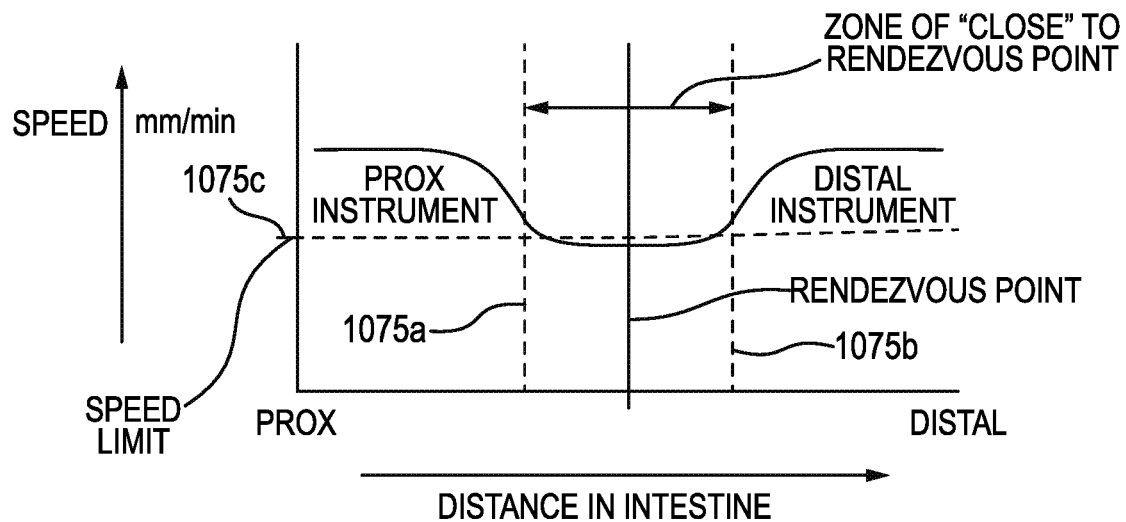
FIG. 24 is a graph showing speed versus distance for the surgical instruments of FIG. 23 operating within a patient's intestines.

Regarding the illustrated system 1000 embodiment, FIG. 24 shows a speed of advancement of the first instrument 1010 (identified as the "Distal Instrument" in FIG. 24) and the second instrument 1030 (identified as the "Proximal Instrument" in FIG. 24) through the patient (in mm/min) compared to a distance from a rendezvous point (identified as the "Distance in Intestine" compared to a "Rendezvous Point" in FIG. 24). The identified Rendezvous Point illustrated in FIG. 24 represents the connected or joint surgical treatment site formed from joining the first and second treatment sites 1070a, 1070b, and the distance in the patient's intestine is shown as increasing from a proximal end of the patient's intestine to a distal end of the patient's intestine with the identified Rendezvous Point approximately in the middle. However, in other embodiments and during other procedures, the distance and the rendezvous point can represent different biological organs and target sites.

Figure 25:
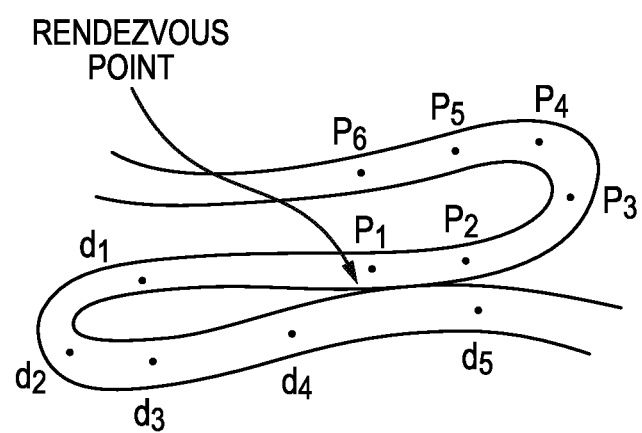
FIG. 25 is an illustrative view of a patient's intestines identifying various distances traveled and an exemplary rendezvous point at a possible surgical site for the surgical instruments of FIG. 23.

The controller 1050 also utilizes threshold values and zones or ranges of values to automatically limit speed of advancement and distance from the rendezvous point of one or both of the first and second instruments 1010, 1030 through the patient to increase safety for the patient. Uppermost speeds of advancement (similar to speed limits) and ranges of distances from the treatment sites 1070a, 1070b are selected for the first and second instruments 1010, 1030, as illustrated in FIG. 24. Additionally, the various threshold values and ranges can also be interrelated in some embodiments. For instance, in the embodiment illustrated in FIG. 24, a "Zone of 'Close' to Rendezvous Point" and a Speed Limit threshold are provided. The "Zone of 'Close' to Rendezvous Point" represents a preselected distance from the rendezvous point and includes a lower threshold distance value 1075a and an upper threshold distance value 1075b on either side of the rendezvous point. Furthermore, the Speed Limit threshold 1075c represents an upper limit on the speed of the instruments 1010, 1030. However, the controller 1050 only restricts a speed of advancement of the instruments 1010, 1030 to the Speed Limit threshold 1075c once the instruments 1010, 1030 enter the "Zone of 'Close' to Rendezvous Point." Before entering the provided range between the threshold distance values 1075a, 1075b, the speed of advancement of the instruments 1010, 1030 is not restricted. FIG. 25 illustrates a plurality of distances away from the rendezvous point of FIG. 24 through the patient's intestine during both a proximal approach and a distal approach. For example, a plurality of proximal distances $P_1, P_2, P_3, P_4, P_5, P_6$, which are associated with the first surgical instrument 1010 and the first endoscope 1030 that approach the rendezvous point from a proximal location relative thereto, and a plurality of distal distances $D_1, D_2, D_3, D_4, D_5, D_6$, which are associated with the second surgical instrument 1020 and the second endoscope 1040 that approach the rendezvous point from a distal location relative thereto, can be identified, and one or more thresholds can be established at one or more of the distances to control speeds of advancement of the instruments 1010, 1030 and endoscopes 1020, 1040.

Known travel paths can be created for each instrument 1010, 1030 to assist the controller 1050 and the user in correctly navigating through the patient's intestines to reach the rendezvous point given the length and complexity of the intestines. In such an example, points of approximately 2 cm apart from one another are picked and tagged during creation of a computer image along the patient's intestines during intestine laparoscopic mobilization, such as the plurality of proximal distances $P_1, P_2, P_3, P_4, P_5, P_6$ and the plurality of distal distances $D_1, D_2, D_3, D_4, D_5, D_6$ illustrated in FIG. 25. The controller 1050 thus knows a distance to each point $P_n$ and $D_n$ with reference to the system's 1000 global coordinate system as well as a position of each endoscope 1020, 1040 within the global coordinate system, and the controller 1050 can track each endoscope's 1020, 1040 distance to the rendezvous point through the compliant curving anatomy of the patient's intestine. Thus, instead of requiring a user to separately monitor multiple systems that each has its own instruments and endoscopes, the controller 1050 can track and limit speed of advancement, appliable force, and/or distance from a selectable point for the system 1000 that includes multiple instruments 1010, 1030 and multiple endoscopes 1020, 1040 to increase safety and precision during placement while also allowing the user to focus more fully on the current procedure and less on monitoring and tracking a plurality of instruments and endoscopes.

Once the instruments 1010, 1030 have reached the treatment sites 1070a, 1070b but before deployment of the implant parts 1080a, 1080b, the instruments 1010, 1030 interact with each other through at least one shared, intact tissue wall, and the controller 1050 makes determinations about the tissue based on the interactions. For example, the controller 1050 determines tissue properties such as thickness, stiffness, cross-sectional tissue composition, etc. By determining tissue properties, various specific deployment or treatment sites can be identified based on specific tissue properties.

For example, in the FIG. 23 embodiment, the first and second surgical treatment sites 1070a, 1070b are initially identified using various pre-operative imaging approaches, such as CT or MRI scans, to identify preliminary locations for implant deployment. While maneuvering the implant parts 1080a, 1080b into position, however, the controller 1050 monitors tissue properties to identify an exact deployment location for each implant part 1080a, 1080b with appropriate tissue properties. Determinations are made based on one or more different factors, such as measured tissue impedance, tissue thickness, tissue density, cross-sectional tissue composition of the surrounding tissue walls (including mucosal, sub-mucosal, or serosal layers), multispectral or ultrasonic non-visual light spectrum imaging, tissue and anatomy visualization, distances between the instruments 1010, 1030 and endoscopes 1020, 1040, resistance from surrounding tissue to further advancement of the instruments 1010, 1030 and endoscopes 1020, 1040, etc. In the illustrated embodiment, the two endoscopes 1020, 1040 are brought together with only a wall thickness of each lumen within the intestines separating the endoscopes 1020, 1040, and the distance between the two endoscopes 1020, 1040 thus is used to help determine a combined tissue wall thicknesses between the surgical treatment sites 1070a, 1070b. When deploying the implant parts 1080a, 1080b, a user attempts to identify locations that prove adequate compression to cause erosion of the tissue wall between the two implant parts 1080a, 1080b and that will result in mated serosal to serosal tissue layers to create a healing bond between the first and second surgical treatment sites 1070a, 1070b. In other embodiments, different imaging or analysis approaches can be taken, such as using noninvasive indocyanine green (ICG) to visualize blood flow to assist a user in ensuring that only intestine walls are between the two implant parts 1080a, 1080b without a mesentery or connective tissue therebetween. A user can further utilize ICG in some embodiments to help determine intestine profusion viability, especially at the surgical treatment sites 1070a, 1070b, and a user can also help to confirm tissue properties or tissue types in some embodiments by comparing tissue property determinations made from within the intestines, such as through use of optical coherence tomography, confocal laser, etc., and made from outside the intestines, such as through use of multispectral non-contact imaging or impedance contact spectroscopy.

The two-part magnetic anastomosis device is subsequently deployed at a location that provides the best chance of success based on the local tissue properties. In some embodiments, the controller 1050 and/or the user seeks out one or more of the different tissue factors discussed above, such as measured tissue impedance, tissue thickness, tissue density, etc., to help prevent the instruments 1010, 1030 from penetrating tissue walls within the patient during the surgical procedure and thereby reduce overall harm to the patient. In other embodiments, one or more additional instruments, such as the laparoscope 1085, various probes or lasers, balloons, etc., can be used to assist in making additional determinations of surrounding tissue and/or to assist in rotating and maneuvering surrounding tissue to ensure that only desirable tissue is positioned between the instruments 1010, 1030 before implant deployment or other treatment.

As the first and second implant parts 1080a, 1080b of the two-part magnetic anastomosis device reach the respective treatment sites 1070a, 1070b in the exemplary embodiment shown in FIG. 23, the first and second surgical instruments 1010, 1030 are rotated or articulated, as needed, based on detected locations and orientations of each instrument 1010, 1030 to help ensure successful delivery of the first and second implant parts 1080a, 1080b at each site 1070a, 1070b, respectively. As with the first and second endoscopes 1020, 1040 discussed above, the location and orientation of each instrument 1010, 1030 is tracked by the controller 1050 of the system 1000 using EM tracked tips (and/or other tracking means) to determine locations and orientations of each instrument 1010, 1030 in the global coordinate frame of the system 1000, which is known by the controller 1050.

While delivery of implants is provided in the illustrated embodiment, the system 1000 can coordinate synchronized or coordinated movements and treatments between the various instruments 1010, 1030 and endoscopes 1020, 1040 for various other surgical procedures to allow the user to perform a cooperative treatment using two or more surgical instruments located at different points in a body cavity such that each instrument can complete a portion of the cooperative treatment even when the instruments are not able to directly visualize each other, for example as a result of being obscured from one another by surrounding tissue.

Figure 26:
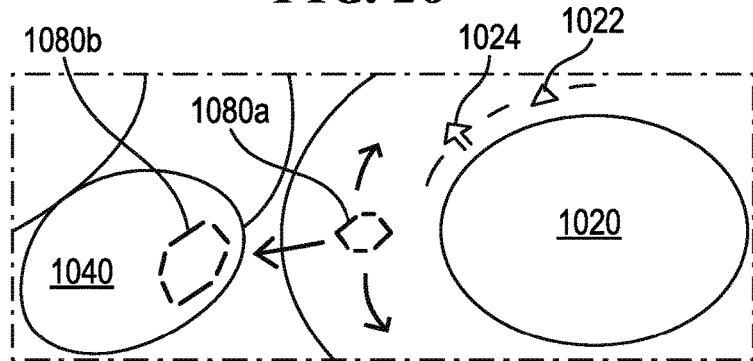
FIG. 26 is an illustrative view of another example embodiment for providing a common field of view by augmenting multiple points of view into the common field of view and by overlaying various exemplary navigational and orientation indicators into the common field of view.

FIG. 26 illustrates an exemplary process of aligning the first implant part 1080a with the second implant part 1080b using an EM tracked distal end of each of the endoscopes 1020, 1040 and a plurality of EM trackers (e.g., three or other number) on each of the first and second implant parts 1080a, 1080b. An "up" or neutral position or orientation of the first endoscope 1020 is determined using the EM tracker thereon. The determined orientation is indicated by an arrow 1022 in FIG. 26. A current orientation of the first implant part 1080a can be determined based on the location of the plurality of EM trackers thereon relative to the first endoscope 1020. The current orientation of the first implant part 1080a is indicated by an arrow 1024 relative to the arrow 1022. The current orientation of the second implant part 1080b can be determined using similar steps regarding the second endoscope 1040, and the first implant part 1080a and/or the second implant part 1080a can be realigned or reoriented, as needed, to align the two implant parts 1080a, 1080b, as shown by solid arrows regarding the first implant part 1080a in FIG. 26, to ensure successful alignment and deployment despite obscured views between the two endoscopes 1020, 1040. In other exemplary embodiments, alignment indicators similar to those shown in FIG. 26 can be incorporated or augmented into various displays used by the system 1000, such as in a laparoscopic view utilized by the user.

Figure 27:
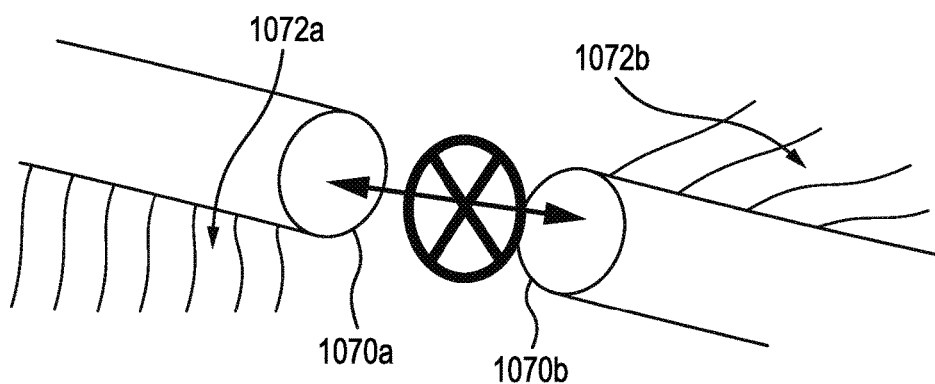
FIG. 27 is an illustrative view of exemplary surgical sites within a patient's intestines that are oriented incorrectly.
Figure 28:
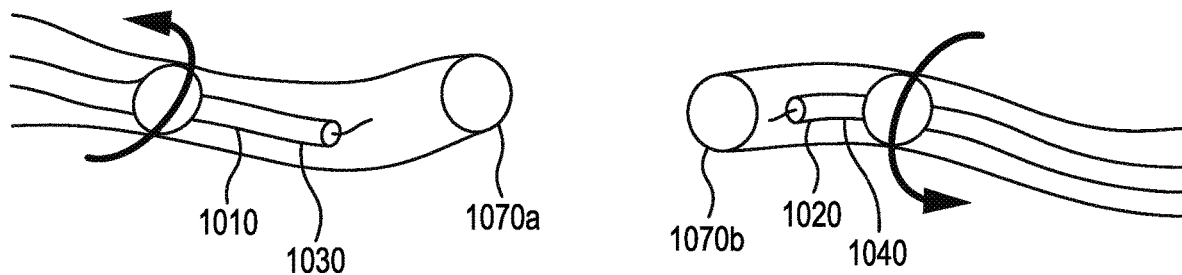
FIG. 28 is an illustrative view of the exemplary surgical sites of FIG. 27 being rotated by the surgical instruments of FIG. 23.
Figure 29:
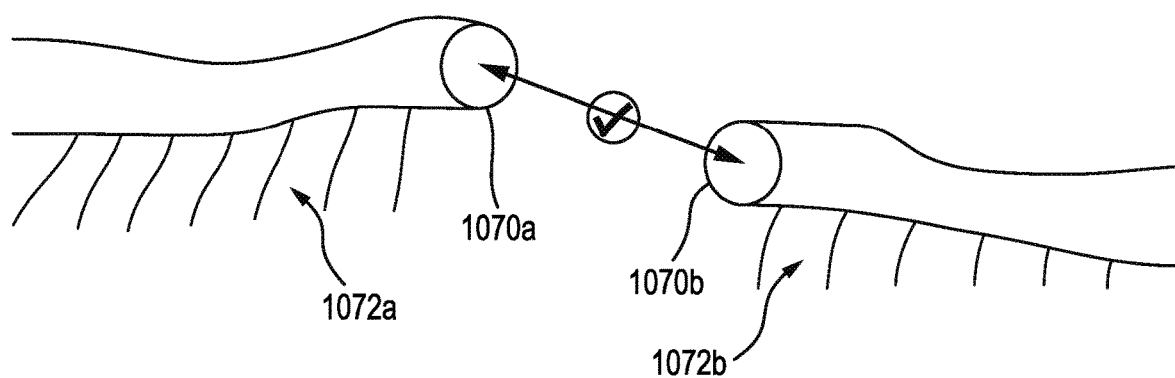
FIG. 29 is an illustrative view of the exemplary surgical sites of FIG. 27 once orientation has been corrected.

Furthermore, while aligning the first and second implant parts 1080a, 1080b, the orientation of the instruments 1010, 1030 and the endoscopes 1020, 1040 and the properties of the tissue therebetween are monitored by the controller 1050 to ensure that there is no inadvertent damage to surrounding tissue, such as tissue twisting or blood flow occlusion, during deployment. For example, FIG. 27, FIG. 28, and FIG. 29 illustrate an exemplary deployment of the implant parts 1080a, 1080b. The controller 1050 causes a notification to be shown on the display 1060 and/or another display to notify the user that deployment of the two-part magnetic anastomosis device in FIG. 27 should not yet be performed due to an orientation mismatch between the surrounding tissue on each side of the surgical treatment sites 1070a, 1070b based in part on identification of certain anatomical structures 1072a, 1072b positioned on each side of the surgical treatment sites 1070a, 1070b. In other embodiments, the controller 1050 can restrict actuation of the instruments 1010, 1030 to prevent deployment of the two-part magnetic anastomosis device because of the orientation mismatch. In FIG. 28, the instruments 1010, 1030 and the endoscopes 1020, 1040 assist in rotating the surrounding tissue to ensure proper anatomical orientation between the surgical treatment sites 1070a, 1070b, and in FIG. 29, the controller 1050 causes a notification to be shown on the display 1060 and/or another display to notify the user that deployment of the two-part magnetic anastomosis device can proceed because the surrounding tissue is correctly oriented on each side of the surgical treatment sites 1070a, 1070b, thus ensuring proper blood flow and preventing potential twisting of the patient's intestines. In other embodiments in which the controller 1050 can initially restrict actuation of the instruments 1010, 1030 to prevent deployment of the two-part magnetic anastomosis device because of the orientation mismatch, the controller 1050 can re-enable actuation of the instruments 1010, 1030 to allow deployment of the two-part magnetic anastomosis device because of the correct orientation. In other embodiments, various other tissue manipulation approaches can be used to assist in rotation, such as utilizing another surgical instrument introduced to one or both of the surgical treatment sites 1070a, 1070b to perform rotational laparoscopic assistance or through use of an endoluminal balloon to assist in rotation of the patient's intestines.

When the first and second implant parts 1080a, 1080b have been reoriented, rotated, and aligned with each other based on any desired movement from the endoscopes 1020, 1040 and/or the instruments 1010, 1030, the first and second implant parts 1080a, 1080b are deployed simultaneously. Because the first and second implant parts 1080a, 1080b are magnetic, the first and second parts 1080a, 1080b connect together through the jejunum wall when deployed, forming the first and second treatment sites 1070a, 1070b into a single connected or joint surgical treatment site.

Additional surgical instrument(s) and/or additional scope(s) can be used in some surgical procedures to assist with additional visualization, movement of surrounding tissue, assistance in positioning implants, etc. Use of additional surgical instrument(s) and/or additional scope(s) can be beneficial in certain embodiments because of the difficulty in reaching some target sites within a patient, such as a target site within the small intestines given the length and complexity of maneuvering through the intestines. For example, the system 1000 can incorporate one or more additional surgical instruments and/or one or more additional scope(s) introduced to the patient's body from one or more additional access locations, and the controller 1050 can coordinate movement of the incorporated surgical instruments and/or scope(s) to perform cooperative procedures. FIG. 23 illustrates, for example, the laparoscope 1085, having a field of view 1085a indicated by dashed lines, introduced into the patient from a laparoscopic approach and a grasper 1087 also introduced into the patient from a laparoscopic approach. In the illustrated embodiment, the laparoscope 1085 and the grasper 1087 can be used help orient and align one or more of the instruments 1010, 1030, endoscopes 1020, 1040, and the implant parts 1080a, 1080b to ensure successful deployment of the implant parts 1080a, 1080b. For example, the grasper 1087 can be introduced to manipulate portions of the small intestine to ensure each implant part 1080a, 1080b is able to reach a desired deployment location, as visually indicated within the field of view 1085a of the laparoscope 1085. An instrument other than a grasper can be used to manipulate portions of the small intestine, such as a dissector.

In still other embodiments, various surgical instrument(s) and/or scope(s), such as a double-balloon enteroscope, a self-propelling dual flex endoscope, etc., can be used in place of or in addition to one or more of the surgical instruments to assist in navigating and controlling surrounding tissue, such as the small intestines given their length and complexity. For example, if a user wants to position one of the endoscopes 1020, 1040 deeper into the jejunum of the patient, a double-balloon enteroscope can be used to bunch up an amount of small intestines onto a selected one of? the endoscopes 1020, 1040 while preventing the selected endoscope 1020, 1040 from sliding or retracting backwards out of the jejunum. The approach allows several feet or more of small intestines to be bunched up on several inches of the selected endoscope 1020, 1040, which is useful because endoscopes have a set length and a target surgical site within the patient's small intestines may be farther into the intestines than the length of the endoscope. In such an example, a user may need to use a cooperative laparoscopic and endoscopic interaction to allow enough intestinal tissue to be pulled onto the selected endoscope 1020, 1040.

Figure 30:
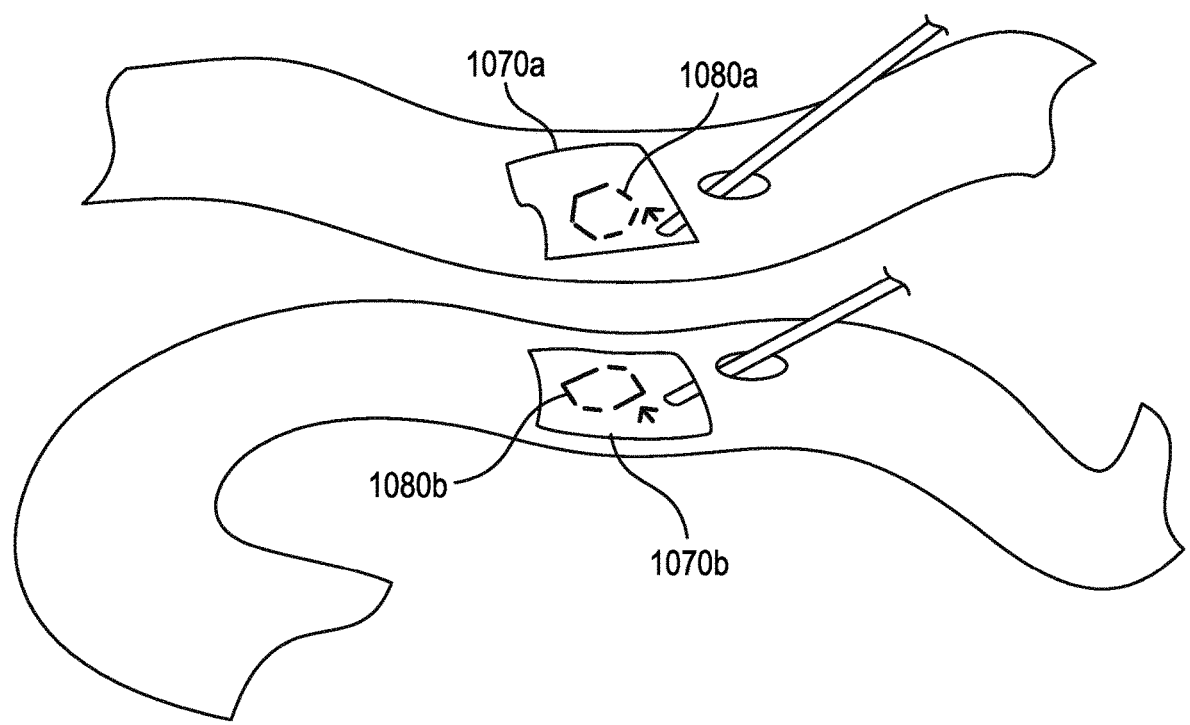
FIG. 30 is an illustrative view of the surgical instruments of FIG. 23 utilizing a laparoscopic approach.

In other examples, a double balloon enteroscope may be used to assist in deploying one of the implant parts 1080a, 1080b of the two-part magnetic anastomosis device. For example, a distal-most balloon of the enteroscope can be positioned distal of the second implant part 1080b to be deployed, and when the distal-most balloon is positioned at the second surgical treatment site 1070b, there will be increased visibility at the site because of the balloon. Additional details regarding various embodiments of tissue manipulation instruments are provided in, for example, previously mentioned U.S. App. No. 63/249,980 entitled "Cooperative Access" filed on Sep. 29, 2021. Various additional navigational aids can also be used in some embodiments, such as introducing a laparoscopic probe to the target site and/or otherwise tagging various sites within the patient through known means, such as virtually in a robotic system or with a fiducial marker. In various other embodiments, one or both of the implant parts 1080a, 1080b of the two-part magnetic anastomosis device can be deployed using the laparoscopic approach instead of through one or both of the natural orifices, discussed above. Using the laparoscopic approach, one or both of the implant parts 1080a, 1080b are deployed using cooperative movement between the instruments 1010, 1030 and the endoscopes 1020, 1040 through the patient's jejunum or small intestine wall, as illustrated in FIG. 30. This approach can utilize various laparoscopic access ports that are commonly used for anatomic mobilization for introducing one or both of the implant parts 1080a, 1080b, thus avoiding a potentially challenging insertion process through the patient's intestines, and the implant parts 1080a, 1080b can use similar tracking and imaging mechanisms to those discussed above to ensure correct alignment and orientation before placement. Additional details regarding various embodiments of a laparoscopic are provided in, for example, previously mentioned U.S. App. No. 63/249,980 entitled "Cooperative Access" filed on Sep. 29, 2021.

Additional details regarding partial jejunal diversions and corresponding implants are provided in U.S. Pat. No. 8,636, 751, titled "Methods and devices for the rerouting of chyme to induce intestinal brake" and issued on Jan. 28, 2014; U.S. Pat. No. 10,206,682, titled "Magnetic tissue compression device with backup mechanical latch" and issued on Feb. 19, 2019; U.S. Pat. No. 10,517,600, titled "Magnetic anastomosis devices with varying magnetic force at a distance" and issued on Dec. 31, 2019; U.S. Pat. No. 10,779,831, titled "Systems, devices, and methods for forming anastomoses" and issued on Sep. 22, 2020; U.S. Pat. No. 11,033,272, titled "Methods for partial diversion of the intestinal tract" and issued on Jun. 15, 2021; U.S. Patent Pub. No. 2017/0265866, titled "Targeting systems for providing accurate placement of magnetic anastomosis devices" and published on Sep. 21, 2017; and PCT Pub. No. WO2012007052A1, titled "A device for an endoluminal cholecysto-enterostomy" and published on Jan. 19, 2012, all of which are incorporated herein by reference in their entirety.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety for all purposes.

What is claimed is:

1. A system, comprising:
a first surgical instrument configured to be inserted into a first portion of a body cavity and to operate on a first surgical treatment site located within the body cavity of a patient;
a second surgical instrument configured to be inserted into a second portion of the body cavity and to operate on a second surgical treatment site located within the body cavity, the second portion of the body cavity being different than the first portion of the body cavity, and the second surgical treatment site being different than the first surgical treatment site;
a first flexible endoscope having a first image sensor and configured to be positioned such that the second surgical instrument is not within a field of view of the first image sensor;
a second flexible endoscope having a second image sensor and positioned such that the first surgical instrument is not within a field of view of the second image sensor;
a controller configured to, with the second surgical instrument being in the body cavity and not being within the field of view of the first image sensor and with the first surgical instrument being in the body cavity and not being within the field of view of the second image sensor, receive images gathered by each of the first and second image sensors, determine a first location of the first surgical instrument and a second location of the second surgical instrument relative to one another, and cause synchronized surgical actions between the first and second surgical instruments at the first and second surgical treatment sites, respectively, wherein the synchronized surgical actions include the first surgical instrument at least one of moving relative to the first surgical treatment site and delivering treatment to the first surgical treatment site and the second surgical instrument at least one of moving relative to the second surgical treatment site and delivering treatment to the second surgical treatment site;

a first portion of a surgical implant configured to be releasably attached to the first surgical instrument and delivered into the body cavity while releasably attached to the first surgical instrument; and a second portion of the surgical implant configured to be releasably attached to the second surgical instrument and delivered into the body cavity while releasably attached to the second surgical instrument;

wherein the controller causing the synchronized surgical actions includes actuating deployment of the first and second portions of the surgical implant simultaneously;

the first portion of the surgical implant includes a first electromagnetic tracker configured to provide data regarding the first portion of the surgical implant to the controller;

the second portion of the surgical implant includes a second electromagnetic tracker configured to provide data regarding the second portion of the surgical implant to the controller; and the deployment of the first and second portions of the surgical implant by the controller is based on the received data regarding the first and second portions of the surgical implant.

2. The system of claim 1, wherein the body cavity comprises a jejunum, and the surgical implant comprises an anastomosis device.

3. The system of claim 1, further comprising a third surgical instrument configured to be introduced into a third portion of the body cavity, and configured to assist the controller to cause the synchronized surgical actions of the first and second surgical instruments.

4. The system of claim 3, wherein the first surgical instrument is configured to be introduced into the patient through a first natural orifice of the patient, the second surgical instrument is configured to be introduced into the patient through a second, different natural orifice of the patient, and the third surgical instrument is configured to be introduced into the patient from a laparoscopic approach.

5. The system of claim 1, wherein the synchronized surgical actions between the first and second surgical instruments include simultaneous synchronized surgical actions at the first and second surgical treatment sites.

6. The system of claim 1, wherein the controller is configured to cause the synchronized actions between the first and second surgical instruments when tissue obstructs the second surgical instrument from the field of view of the first image sensor and when tissue obstructs the first surgical instrument from the field of view of the second image sensor.

7. The method of claim 1, wherein the synchronized surgical actions are such that tissue within the body cavity is rotated.

8. The method of claim 1, wherein the synchronized surgical actions maintain a proper anatomical orientation between the first and second surgical treatment sites.

9. The method of claim 1, wherein the synchronized surgical actions include the first surgical instrument and the second surgical instrument moving such that first and second implant portions align with each other.

10. A system, comprising:
a data processor; and
a memory storing instructions configured to cause the processor to perform operations comprising:
receiving, with a second surgical instrument being outside of a field of view of a first endoscope, from a first image sensor of the first endoscope, first image data characterizing a first portion of a body cavity of a patient;
receiving, with a first surgical instrument being outside of a field of view of a second endoscope, from a second image sensor of the second endoscope, second image data characterizing a second portion of the body cavity;
determining based on the first image data and with the first surgical instrument being in the body cavity outside of the field of view of the second endoscope, a first location of the first surgical instrument, which is configured to operate on tissue at a first surgical treatment site in the first portion of the body cavity;
determining based on the second image data and with the second surgical instrument being in the body cavity outside of the field of view of the first endoscope, a second location of the second surgical instrument relative to the first location of the first surgical instrument, the second surgical instrument being configured to operate on tissue at a second surgical treatment site; and
causing, with the first surgical instrument being outside of the field of view of the second endoscope and with the second surgical instrument being outside of the field of view of the first endoscope, synchronized surgical actions between the first and second surgical instruments at the first and second surgical treatment sites, respectively;
wherein the synchronized surgical actions include the first surgical instrument at least one of moving relative to the first surgical treatment site and delivering treatment to the first surgical treatment site and the second surgical instrument at least one of moving relative to the second surgical treatment site and delivering treatment to the second surgical treatment site;
causing the synchronized surgical actions includes actuating deployment of first and second portions of a surgical implant simultaneously; and
the deployment of the first and second portions of the surgical implant is based on electromagnetic tracking data regarding the first and second portions of the surgical implant.

11. The system of claim 10, wherein the deployment of the first and second portions of the surgical implant includes releasing the first portion of the surgical implant from the first surgical instrument and releasing the second portion of the surgical implant from the second surgical instrument.

12. The system of claim 10, wherein the body cavity comprises a jejunum, and the surgical implant comprises a two-part magnetic anastomosis device.

13. The system of claim 10, wherein the operations further comprise receiving, from a third image sensor of a third endoscope, third image data characterizing a third portion of the body cavity of the patient.

14. The system of claim 10, wherein the synchronized surgical actions include avoiding penetrating any tissue by the first and second surgical instruments.

15. The system of claim 10, wherein the electromagnetic tracking data includes first data regarding the first portion of the surgical implant and second data regarding the second portion of the surgical implant; and the operations further comprise receiving the first data from a first electromagnetic tracker of the first portion of the surgical implant; and receiving the second data from a second electromagnetic tracker of the second portion of the surgical implant.

16. A method, comprising:

receiving, with a second surgical instrument being in a body cavity of a patient outside of a field of view of a first image sensor of a first endoscopic system, from the first image sensor first image data characterizing a first portion of the body cavity of the patient;

receiving, with a first surgical instrument being in the body cavity outside of a field of view of a second image sensor of a second endoscopic system, from the second image sensor second image data characterizing a second portion of the body cavity;

determining, by a controller, based on the first image data and with the first surgical instrument being in the body cavity outside of the field of view of the second image sensor, a first location of the first surgical instrument manipulating tissue at a first surgical treatment site disposed within the first portion of the body cavity of the patient;

determining, by the controller, based on the second image data and with the second surgical instrument being in the body cavity outside of the field of view of the first image sensor, a second location of the second surgical instrument relative to the first surgical instrument, the second surgical instrument manipulating tissue at a second surgical treatment site disposed within the second portion of the body cavity; and causing, by the controller, with the first surgical instrument being in the body cavity outside of the field of view of the second endoscopic system and with the second surgical instrument being in the body cavity outside of the field of view of the first endoscopic system, synchronized surgical actions between the first and second surgical instruments at the first and second surgical treatment sites, respectively;

wherein the synchronized surgical actions include the first surgical instrument at least one of moving relative to the first surgical treatment site and delivering treatment to the first surgical treatment site and the second surgical instrument at least one of moving relative to the second surgical treatment site and delivering treatment to the second surgical treatment site;

causing the synchronized surgical actions includes actuating deployment of first and second portions of a surgical implant simultaneously; and the deployment of the first and second portions of the surgical implant is based on electromagnetic tracking data regarding the first and second portions of the surgical implant.

17. The method of claim 16, wherein the first portion of the surgical implant is delivered into the body cavity while releasably attached to the first surgical instrument;

the second portion of the surgical implant is delivered into the body cavity while releasably attached to the second surgical instrument; and the deployment of the first and second portions of the surgical implant includes releasing the first portion of the surgical implant from the first surgical instrument and releasing the second portion of the surgical implant from the second surgical instrument.

18. The method of claim 16, wherein the body cavity comprises a jejunum, and the surgical implant comprises a two-part magnetic anastomosis device.

19. The method of claim 16, further comprising receiving, from a third image sensor of a third endoscope, third image data characterizing a third portion of the body cavity of the patient.

20. The method of claim 16, wherein the electromagnetic tracking data includes first data regarding the first portion of the surgical implant and second data regarding the second portion of the surgical implant; and the method further comprises receiving, by the controller, the first data from a first electromagnetic tracker of the first portion of the surgical implant; and receiving, by the controller, the second data from a second electromagnetic tracker of the second portion of the surgical implant.

* * * * *